US012703116B2

(12) United States Patent
Cher et al.

(10) Patent No.: US 12,703,116 B2
(45) Date of Patent: Aug. 11, 2026

(54) UNIFIED PNEUMATIC AND ELECTRICAL CONNECTOR SYSTEM AND METHOD

(71) Applicant: ROAM ROBOTICS INC., San Francisco, CA (US)

(72) Inventors: Eitan Cher, Minneapolis, MN (US); Ashley Swartz, Daly City, CA (US); Zack Stephanchick, San Francisco, CA (US); Ronald Lam, Berkeley, CA (US); Phillip Dao Pham, San Francisco, CA (US); Kevin Conrad Kemper, San Francisco, CA (US); Timothy Alan Swift, Walnut Creek, CA (US)

(73) Assignee: ROAM ROBOTICS INC., San Francisco, CA (US)

( * ) Notice: Subject to any disclaimer, the term of this patent is extended or adjusted under 35 U.S.C. 154(b) by 809 days.

(21) Appl. No.: 17/889,589

(22) Filed: Aug. 17, 2022

(65) Prior Publication Data

US 2023/0054745 A1 Feb. 23, 2023

Related U.S. Application Data

(60) Provisional application No. 63/233,976, filed on Aug. 17, 2021, provisional application No. 63/233,988, filed on Aug. 17, 2021.

(51) Int. Cl.
*B25J 9/00* (2006.01)
*B25J 9/14* (2006.01)
(Continued)

(52) U.S. Cl.
CPC ......... *B25J 19/0025* (2013.01); *B25J 9/0006* (2013.01); *B25J 9/142* (2013.01);
(Continued)

(58) Field of Classification Search
CPC ...... B25J 19/0029; F16L 37/004; F16L 37/56; F16L 37/086; A61M 39/10; A61M 39/00; A61M 2039/1027
See application file for complete search history.

(56) References Cited

U.S. PATENT DOCUMENTS 3,503,634 A * 3/1970 Cadiou .............. F16L 19/0212 277/609
3,823,711 A 7/1974 Hatton
(Continued)

FOREIGN PATENT DOCUMENTS

CN 1693036 A 11/2005
CN 101151071 A 3/2008
(Continued)

OTHER PUBLICATIONS

Branham, "3 Advantages of Using an Oval Bore Compact Cylinder," W.C. Branham Blog—Solutions in Motion TM. Retrieved Feb. 9, 2023, from https://blog.wcbranham.com/oval-bore-compact-cylinder, Jan. 12, 2018, 7 pages.
(Continued)

*Primary Examiner* — Brandy S Lee
*Assistant Examiner* — Rohan Patel
(74) *Attorney, Agent, or Firm* — Davis Wright Tremaine LLP

(57) ABSTRACT

An exoskeleton system including one or more unitary cables comprising at least a first unitary cable configured to extend from an exoskeleton device to a first actuator unit, the first unitary cable comprising: one or more power lines, one or more fluid lines, one or more communication lines, and a cable connector that includes a first connector side and a second connector side.

20 Claims, 27 Drawing Sheets

(51) Int. Cl.

| | |
|---|---|
| ***B25J 19/00*** | (2006.01) |
| *A61M 39/00* | (2006.01) |
| *A61M 39/10* | (2006.01) |
| *F16L 37/00* | (2006.01) |
| *F16L 37/56* | (2006.01) |

(52) U.S. Cl.

CPC .......... *B25J 19/0029* (2013.01); *A61M 39/00* (2013.01); *A61M 2039/1027* (2013.01); *F16L 37/004* (2013.01); *F16L 37/56* (2013.01)

(56) References Cited

U.S. PATENT DOCUMENTS

| | | | |
|---|---|---|---|
| 3,868,952 | A | 3/1975 | Hatton |
| 3,982,531 | A | 9/1976 | Shaffer |
| 3,993,056 | A | 11/1976 | Rabischong et al. |
| 4,080,877 | A | 3/1978 | deFries |
| 4,274,399 | A | 6/1981 | Mummert |
| 4,408,600 | A | 10/1983 | Davis |
| 4,523,582 | A | 6/1985 | Barber |
| 4,623,158 | A | 11/1986 | Monreal |
| 4,671,258 | A | 6/1987 | Barthlome |
| 4,720,923 | A | 1/1988 | Quinton et al. |
| 4,944,755 | A | 7/1990 | Hennequin et al. |
| 4,953,856 | A | 9/1990 | Fox, III |
| 5,033,457 | A | 7/1991 | Bonutti |
| 5,067,302 | A | 11/1991 | Boeckmann |
| 5,169,169 | A | 12/1992 | Crawford |
| 5,295,704 | A | 3/1994 | Flock |
| 5,483,838 | A | 1/1996 | Holden |
| 5,704,945 | A | 1/1998 | Wagner et al. |
| 5,780,123 | A | 7/1998 | Kamiyama et al. |
| 5,951,048 | A | 9/1999 | Slaughter |
| 6,117,507 | A | 9/2000 | Smith |
| 6,248,463 | B1 | 6/2001 | Dopp et al. |
| 6,612,340 | B1 | 9/2003 | Lause |
| 6,776,769 | B2 | 8/2004 | Smith |
| 7,086,322 | B2 | 8/2006 | Schulz |
| 7,479,121 | B2 | 1/2009 | Branch |
| 7,628,766 | B1 | 12/2009 | Kazerooni et al. |
| 8,171,570 | B2 | 5/2012 | Adarraga |
| 8,784,350 | B2 | 7/2014 | Cohen |
| 9,205,560 | B1 | 12/2015 | Edsinger et al. |
| 9,474,632 | B2 | 10/2016 | Bosscher et al. |
| 9,480,618 | B2 | 11/2016 | Hsiao-Wecksler et al. |
| 9,709,206 | B2 | 7/2017 | Duttenhoefer et al. |
| 9,821,475 | B1 | 11/2017 | Lynn et al. |
| 9,827,667 | B2 | 11/2017 | Griffith et al. |
| 9,995,321 | B2 | 6/2018 | Lynn et al. |
| 10,012,229 | B2 | 7/2018 | Lynn et al. |
| 10,245,204 | B2 | 4/2019 | Sandler et al. |
| 10,322,015 | B2 | 6/2019 | Lee et al. |
| 10,385,644 | B2 | 8/2019 | Guidry et al. |
| 10,543,110 | B2 | 1/2020 | Piercy et al. |
| 10,548,800 | B1 | 2/2020 | Barnes |
| 10,562,180 | B2 | 2/2020 | Telleria et al. |
| 10,605,365 | B1 | 3/2020 | Griffith et al. |
| 10,611,020 | B2 | 4/2020 | Griffith et al. |
| 10,619,633 | B2 | 4/2020 | Lynn et al. |
| 10,702,742 | B2 | 7/2020 | Sharma et al. |
| 10,780,011 | B2 | 9/2020 | Yang et al. |
| 10,780,012 | B2 | 9/2020 | Lamb et al. |
| 10,966,895 | B2 | 4/2021 | Lamb et al. |
| 11,033,450 | B2 | 6/2021 | Lamb et al. |
| 11,191,653 | B2 | 12/2021 | Grandmaison et al. |
| 11,213,417 | B2 | 1/2022 | Piercy et al. |
| 11,234,888 | B2 | 2/2022 | Mooney et al. |
| 11,254,002 | B1 | 2/2022 | Ebrahimi Afrouzi et al. |
| 11,259,979 | B2 | 3/2022 | Swift et al. |
| 11,351,083 | B2 | 6/2022 | Swift et al. |
| 11,498,203 | B2 | 11/2022 | Ding et al. |
| 11,780,186 | B1 | 10/2023 | Swierkocki et al. |
| 11,801,153 | B2 | 10/2023 | Bulea et al. |
| 2001/0029343 | A1 | 10/2001 | Seto et al. |
| 2002/0026794 | A1 | 3/2002 | Shahinpoor et al. |
| 2004/0010720 | A1 | 1/2004 | Singh et al. |
| 2004/0102723 | A1 | 5/2004 | Horst |
| 2004/0158175 | A1 | 8/2004 | Ikeuchi et al. |
| 2004/0176715 | A1 | 9/2004 | Nelson |
| 2005/0066810 | A1 | 3/2005 | Schulz |
| 2005/0102863 | A1 | 5/2005 | Hannon et al. |
| 2005/0107726 | A1 | 5/2005 | Oyen et al. |
| 2005/0124924 | A1 | 6/2005 | Slautterback et al. |
| 2005/0177082 | A1 | 8/2005 | Bledsoe |
| 2006/0069336 | A1 | 3/2006 | Krebs et al. |
| 2006/0128538 | A1 | 6/2006 | Sato et al. |
| 2006/0161220 | A1 | 7/2006 | Kobayashi et al. |
| 2006/0173552 | A1 | 8/2006 | Roy |
| 2006/0174760 | A1 | 8/2006 | Rentz |
| 2006/0178030 | A1 * | 8/2006 | Lund ..................... H01B 9/003 439/287 |
| 2006/0184280 | A1 | 8/2006 | Oddsson et al. |
| 2006/0207726 | A1 | 9/2006 | Driver et al. |
| 2006/0211956 | A1 | 9/2006 | Sankai |
| 2007/0042710 | A1 | 2/2007 | Mahini et al. |
| 2007/0061107 | A1 | 3/2007 | Vock et al. |
| 2007/0075543 | A1 | 4/2007 | Marx et al. |
| 2007/0239087 | A1 | 10/2007 | Kivisto |
| 2008/0009771 | A1 | 1/2008 | Perry et al. |
| 2008/0161937 | A1 | 7/2008 | Sankai |
| 2008/0195005 | A1 | 8/2008 | Horst et al. |
| 2008/0234608 | A1 | 9/2008 | Sankai |
| 2008/0287850 | A1 | 11/2008 | Adarraga |
| 2009/0024061 | A1 | 1/2009 | Ueda et al. |
| 2009/0118656 | A1 | 5/2009 | Ingimundarson et al. |
| 2009/0179112 | A1 | 7/2009 | Gu |
| 2009/0198164 | A1 | 8/2009 | Krause |
| 2009/0276058 | A1 | 11/2009 | Ueda et al. |
| 2010/0040936 | A1 | 2/2010 | Pozin et al. |
| 2010/0094188 | A1 | 4/2010 | Goffer et al. |
| 2010/0106065 | A1 | 4/2010 | Ward |
| 2010/0114329 | A1 | 5/2010 | Casler et al. |
| 2010/0204627 | A1 | 8/2010 | Kazerooni et al. |
| 2010/0217169 | A1 | 8/2010 | Ingimundarson |
| 2010/0249675 | A1 | 9/2010 | Fujimoto et al. |
| 2010/0270771 | A1 | 10/2010 | Kobayashi et al. |
| 2010/0280424 | A1 | 11/2010 | Kawakami et al. |
| 2010/0292556 | A1 | 11/2010 | Golden |
| 2011/0059355 | A1 | 3/2011 | Zhang et al. |
| 2011/0066088 | A1 | 3/2011 | Little et al. |
| 2011/0071417 | A1 | 3/2011 | Liu et al. |
| 2011/0099026 | A1 | 4/2011 | Oakley et al. |
| 2011/0105966 | A1 | 5/2011 | Kazerooni et al. |
| 2011/0105969 | A1 | 5/2011 | Nace |
| 2011/0112447 | A1 | 5/2011 | Hsiao-Wecksler et al. |
| 2011/0118635 | A1 | 5/2011 | Yamamoto |
| 2011/0186208 | A1 | 8/2011 | Cartabbia et al. |
| 2011/0290798 | A1 | 12/2011 | Corbett et al. |
| 2012/0041348 | A1 | 2/2012 | Maekita |
| 2012/0059291 | A1 | 3/2012 | Nguyen |
| 2012/0259429 | A1 | 10/2012 | Han et al. |
| 2012/0259431 | A1 | 10/2012 | Han et al. |
| 2012/0271211 | A1 | 10/2012 | Bledsoe |
| 2012/0289870 | A1 | 11/2012 | Hsiao-Wecksler et al. |
| 2012/0316477 | A1 | 12/2012 | Hamaya et al. |
| 2012/0328824 | A1 | 12/2012 | Cartabbia et al. |
| 2013/0053736 | A1 | 2/2013 | Konishi |
| 2013/0150980 | A1 | 6/2013 | Swift et al. |
| 2013/0158445 | A1 | 6/2013 | Kazerooni et al. |
| 2013/0172797 | A1 | 7/2013 | Merkley et al. |
| 2013/0197408 | A1 | 8/2013 | Goldfarb et al. |
| 2013/0226048 | A1 | 8/2013 | Unluhisarcikli et al. |
| 2013/0245512 | A1 | 9/2013 | Goffer et al. |
| 2013/0289452 | A1 | 10/2013 | Smith et al. |
| 2013/0296746 | A1 | 11/2013 | Herr et al. |
| 2013/0296758 | A1 | 11/2013 | Castillo |
| 2013/0333368 | A1 | 12/2013 | Durfee et al. |
| 2014/0109560 | A1 | 4/2014 | Ilievski et al. |
| 2014/0124557 | A1 | 5/2014 | Velarde |
| 2014/0148745 | A1 | 5/2014 | Castillo |
| 2014/0148747 | A1 | 5/2014 | Fleming |
| 2014/0171838 | A1 | 6/2014 | Aleksov et al. |
| 2014/0206251 | A1 | 7/2014 | Stokes |
| 2014/0207037 | A1 | 7/2014 | Horst |

(56) References Cited

U.S. PATENT DOCUMENTS

2014/0212243 A1 7/2014 Yagi et al.
2014/0276262 A1 9/2014 Kare et al.
2014/0276264 A1 9/2014 Caires et al.
2014/0277739 A1 9/2014 Kombluh et al.
2014/0318118 A1 10/2014 Mazzeo et al.
2014/0358290 A1 12/2014 Kazerooni et al.
2015/0005685 A1 1/2015 Chetlapalli et al.
2015/0068636 A1 3/2015 Duttenhoefer et al.
2015/0088043 A1 3/2015 Goldfield et al.
2015/0108191 A1 4/2015 Velarde
2015/0126911 A1 5/2015 Abramowicz et al.
2015/0134080 A1 5/2015 Roh
2015/0157525 A1 6/2015 Choi et al.
2015/0173927 A1 6/2015 Castillo
2015/0173993 A1 6/2015 Walsh et al.
2015/0196449 A1 7/2015 Ahn et al.
2015/0197008 A1 7/2015 Yoon et al.
2015/0209214 A1 7/2015 Herr et al.
2015/0219262 A1* 8/2015 Schuessler .............. F16L 41/08 285/317
2015/0285238 A1 10/2015 Lynn et al.
2015/0290794 A1 10/2015 Griffith et al.
2015/0302162 A1 10/2015 Hughes et al.
2015/0323135 A1 11/2015 Smith et al.
2015/0351991 A1 12/2015 Amundson et al.
2015/0351995 A1 12/2015 Zoss et al.
2015/0366696 A1 12/2015 Ingimundarson et al.
2016/0008157 A1 1/2016 Brookover et al.
2016/0045386 A1 2/2016 Sandler et al.
2016/0051389 A1 2/2016 Seligman
2016/0058647 A1 3/2016 Maddry
2016/0074272 A1 3/2016 Ahn et al.
2016/0082319 A1 3/2016 Macri et al.
2016/0089591 A1 3/2016 Williamson
2016/0107309 A1 4/2016 Walsh et al.
2016/0120683 A1 5/2016 Romo et al.
2016/0143800 A1 5/2016 Hyung et al.
2016/0158087 A1 6/2016 Huang et al.
2016/0184166 A1 6/2016 Takenaka et al.
2016/0213548 A1 7/2016 John et al.
2016/0235616 A1 8/2016 Goffer et al.
2016/0242986 A1 8/2016 Nagata et al.
2016/0242987 A1 8/2016 Nagata et al.
2016/0252110 A1 9/2016 Galloway et al.
2016/0261224 A1 9/2016 Madrone et al.
2016/0278948 A1 9/2016 Piercy et al.
2016/0297504 A1 10/2016 Saindon et al.
2016/0300156 A1 10/2016 Bowers et al.
2016/0302955 A1 10/2016 Siddiqui et al.
2016/0331557 A1 11/2016 Tong et al.
2016/0331560 A1 11/2016 Tong et al.
2016/0331624 A1 11/2016 Sankai et al.
2016/0346156 A1 12/2016 Walsh et al.
2017/0018761 A1 1/2017 Ogino
2017/0049587 A1 2/2017 Herr et al.
2017/0071812 A1 3/2017 Sandler et al.
2017/0202724 A1 7/2017 De Rossi et al.
2017/0202725 A1 7/2017 Robertson et al.
2017/0246068 A1 8/2017 Schultz et al.
2017/0252255 A1 9/2017 Asano et al.
2017/0259157 A1 9/2017 Stewart et al.
2017/0279126 A1 9/2017 Dreher
2017/0282360 A1 10/2017 Telleria et al.
2017/0356201 A1 12/2017 Campbell
2018/0028806 A1 2/2018 Hardt et al.
2018/0042803 A1 2/2018 Amundson
2018/0056104 A1 3/2018 Cromie et al.
2018/0071129 A1 3/2018 Ozsecen et al.
2018/0079071 A1 3/2018 Griffith et al.
2018/0085280 A1 3/2018 Shimada et al.
2018/0086178 A1 3/2018 Stanek et al.
2018/0090961 A1 3/2018 Namolovan et al.
2018/0092536 A1 4/2018 Sandler et al.
2018/0116852 A1 5/2018 Petursson et al.
2018/0125152 A1 5/2018 Bruel
2018/0153722 A1 6/2018 Cromie et al.
2018/0200878 A1 7/2018 Tsai et al.
2018/0221237 A1 8/2018 Swift et al.
2018/0235830 A1 8/2018 Rokosz et al.
2018/0243546 A1* 8/2018 Leuthardt .......... A61M 39/1011
2018/0264642 A1 9/2018 Harding et al.
2018/0283414 A1 10/2018 Lynn et al.
2018/0290009 A1 10/2018 Avila
2018/0296424 A1 10/2018 Parra et al.
2018/0296425 A1 10/2018 Lamb et al.
2018/0325765 A1 11/2018 Wilmington
2018/0330817 A1 11/2018 Avni et al.
2019/0015233 A1 1/2019 Galloway et al.
2019/0029918 A1 1/2019 Inada et al.
2019/0060156 A1 2/2019 Swift et al.
2019/0060157 A1* 2/2019 Lamb ....................... A61H 3/00
2019/0083002 A1 3/2019 Jang et al.
2019/0090744 A1 3/2019 Mahfouz
2019/0099877 A1 4/2019 Goehlich et al.
2019/0105189 A1 4/2019 Petursson et al.
2019/0105215 A1 4/2019 Dalley et al.
2019/0159954 A1 5/2019 Ozsecen et al.
2019/0168398 A1 6/2019 Lessing et al.
2019/0224922 A1 7/2019 Brensinger
2019/0240103 A1 8/2019 Hepler et al.
2019/0280266 A1 9/2019 Zhang et al.
2019/0283235 A1 9/2019 Nam et al.
2019/0290464 A1 9/2019 Fleming
2019/0290465 A1 9/2019 Fleming
2019/0293223 A1 9/2019 Free et al.
2019/0307583 A1 10/2019 Herr et al.
2019/0328604 A1 10/2019 Contreras-Vidal et al.
2019/0336315 A1 11/2019 Polygerinos et al.
2019/0344433 A1 11/2019 Lerner
2019/0344434 A1 11/2019 Lerner
2019/0350735 A1 11/2019 Ingimundarson et al.
2019/0358808 A1 11/2019 Yoshimi et al.
2019/0383313 A1 12/2019 Fowler et al.
2020/0069441 A1 3/2020 Larose et al.
2020/0100978 A1 4/2020 Moody
2020/0114588 A1 4/2020 Wang et al.
2020/0197209 A1 6/2020 Bejarano et al.
2020/0206899 A1 7/2020 Storz et al.
2020/0223071 A1 7/2020 Mahoney et al.
2020/0253808 A1 8/2020 Swift et al.
2020/0253822 A1 8/2020 Sibue et al.
2020/0306070 A1 10/2020 Hsu et al.
2020/0386354 A1* 12/2020 Zoe ......................... F16G 11/10
2020/0397641 A1 12/2020 Teng et al.
2020/0410892 A1 12/2020 Otsuki et al.
2021/0121729 A1 4/2021 Kim et al.
2021/0162262 A1 6/2021 Lee
2021/0251518 A1 8/2021 Huizenga
2021/0386611 A1 12/2021 Dalley et al.
2022/0004167 A1 1/2022 Zealand et al.
2022/0015490 A1 1/2022 Drasler
2022/0047444 A1 2/2022 Walsh et al.
2022/0087833 A1 3/2022 Farris
2022/0347847 A1 11/2022 Duburcq et al.
2022/0407129 A1 12/2022 Phares
2023/0055998 A1 2/2023 Park et al.
2023/0057294 A1 2/2023 Park et al.
2023/0058389 A1 2/2023 Kaveny et al.

FOREIGN PATENT DOCUMENTS

CN 101960441 A 1/2011
CN 103412003 A 11/2013
CN 104582668 A 4/2015
CN 105205436 A 12/2015
CN 204814712 U 12/2015
CN 105264255 A 1/2016
CN 105590409 A 5/2016
CN 105816301 A 8/2016
CN 105992554 A 10/2016
CN 106029039 A 10/2016
CN 106137489 A 11/2016
CN 106413998 A 2/2017
CN 106420279 A 2/2017

(56) References Cited

FOREIGN PATENT DOCUMENTS

| | | | | |
|---|---|---|---|---|
| CN | 106650224 | A | | 5/2017 |
| CN | 207253461 | U | * | 4/2018 |
| CN | 110545777 | A | | 12/2019 |
| CN | 110603021 | A | | 12/2019 |
| CN | 110868964 | A | | 3/2020 |
| CN | 111135031 | A | | 5/2020 |
| CN | 111278398 | A | | 6/2020 |
| DE | 102011107580 | A1 | | 1/2013 |
| EP | 2827809 | A1 | | 1/2015 |
| EP | 3173191 | A2 | | 5/2017 |
| EP | 3539528 | A1 | | 9/2019 |
| EP | 3576707 | A4 | | 3/2021 |
| FR | 1463850 | A | | 7/1966 |
| JP | S601405 | A | | 1/1985 |
| JP | 862501723 | A | | 7/1987 |
| JP | 1987501723 | A | | 7/1987 |
| JP | 863199965 | A | | 8/1988 |
| JP | 1988199965 | A | | 8/1988 |
| JP | H07163607 | A | | 6/1995 |
| JP | 2000051289 | A | | 2/2000 |
| JP | 2005118959 | A | | 5/2005 |
| JP | 2005296103 | A | | 10/2005 |
| JP | 2006000347 | A | | 1/2006 |
| JP | 2007282991 | A | | 11/2007 |
| JP | 2010263934 | A | | 11/2010 |
| JP | 2011058564 | A | | 3/2011 |
| JP | 2012501739 | A | | 1/2012 |
| JP | 3179088 | U | | 10/2012 |
| JP | 2012532001 | | | 12/2012 |
| JP | 2012532001 | A | | 12/2012 |
| JP | 2014023773 | A | | 2/2014 |
| JP | 2015008938 | A | | 1/2015 |
| JP | 2015089386 | A | | 5/2015 |
| JP | 2015139665 | A | | 8/2015 |
| JP | 2016521212 | A | | 7/2016 |
| JP | 2016137146 | | | 8/2016 |
| JP | 2017086296 | A | | 5/2017 |
| JP | 2017154210 | A | | 9/2017 |
| JP | 2018019899 | A | | 2/2018 |
| JP | 2018184266 | A | | 11/2018 |
| JP | 2019500928 | A | | 1/2019 |
| JP | 2019077037 | A | | 5/2019 |
| JP | 2019093464 | A | | 6/2019 |
| JP | 2019111635 | A | | 7/2019 |
| JP | 2020506030 | A | | 2/2020 |
| JP | 2020518295 | A | | 6/2020 |
| KR | 10-2008-0048450 | A | | 6/2008 |
| KR | 10-2012-0025571 | A | | 3/2012 |
| KR | 20160020780 | A | | 2/2016 |
| KR | 101812603 | B1 | | 12/2017 |
| KR | 10-2020-0052323 | A | | 5/2020 |
| SU | 251758 | | | 11/1970 |
| WO | 8603816 | A1 | | 7/1986 |
| WO | 9722782 | A1 | | 6/1997 |
| WO | 0004852 | A1 | | 2/2000 |
| WO | 2008129096 | A1 | | 10/2008 |
| WO | 2009081710 | A1 | | 7/2009 |
| WO | 2010124172 | A2 | | 10/2010 |
| WO | 2011007569 | A1 | | 1/2011 |
| WO | 2011043095 | A1 | | 4/2011 |
| WO | 2012044621 | A1 | | 4/2012 |
| WO | 2012086202 | A1 | | 6/2012 |
| WO | 2012124853 | A1 | | 9/2012 |
| WO | 2013142777 | A1 | | 9/2013 |
| WO | 2013152929 | A1 | | 10/2013 |
| WO | 2014109799 | A1 | | 7/2014 |
| WO | 2014194257 | A1 | | 12/2014 |
| WO | 2015080596 | A1 | | 6/2015 |
| WO | 2015104832 | A1 | | 7/2015 |
| WO | 2016147195 | A1 | | 9/2016 |
| WO | 2016166442 | A1 | | 10/2016 |
| WO | 2016166588 | A1 | | 10/2016 |
| WO | 2016171548 | A1 | | 10/2016 |
| WO | 2016207855 | A1 | | 12/2016 |
| WO | 2017110453 | A1 | | 6/2017 |
| WO | 2017218661 | A1 | | 12/2017 |
| WO | 2018144937 | A1 | | 8/2018 |
| WO | 2018191710 | A1 | | 10/2018 |
| WO | 2018218336 | A1 | | 12/2018 |
| WO | 2018222930 | A1 | | 12/2018 |
| WO | 2018236225 | A1 | | 12/2018 |
| WO | 2019046488 | A1 | | 3/2019 |
| WO | 2019046489 | A1 | | 3/2019 |
| WO | 2019109178 | A1 | | 6/2019 |
| WO | 2019122364 | A1 | | 6/2019 |
| WO | 2019131386 | A1 | | 7/2019 |
| WO | 2019183397 | A1 | | 9/2019 |
| WO | 2019187030 | A1 | | 10/2019 |
| WO | 2021119512 | A1 | | 6/2021 |
| WO | 2021242742 | A1 | | 12/2021 |

OTHER PUBLICATIONS

Canadian IPO Office Action and Examination Search Report dated Mar. 21, 2023, Patent Application No. 3,051,105, 7 pages.

Chinese Patent Office Decision on Rejection dated Nov. 25, 2022; Application No. 201880024597; 11 pages.

Chinese Patent Office Fourth Office Action dated Mar. 31, 2023, Application No. 201880023218.5; 7 pages.

Israel Notice of Acceptance for Patent Application No. 268306 dated Feb. 1, 2023, 3 pages.

Israel Notice of Acceptance for Patent Application No. 272621 dated Dec. 22, 2022, 4 pages.

Israel Notice of Deficiencies for Patent Application 269860 dated Jul. 25, 2022, 5 pages.

Israel Notice of Deficiencies for Patent Application No. 272623 dated Dec. 7, 2022, 4 pages.

Israel Notice of Deficiencies for Patent Application No. 282165 dated Dec. 18, 2022, 4 pages.

Japan Decision to Grant Application No. 2020-512042 dated Jan. 13, 2023, 2 pages.

Japan First Office Action, Application No. 2022-072995 dated Mar. 8, 2023, 2 pages.

Lamb, WO 2018191710 A1 Oct. 18, 2018 (full text). [online] [retrieved on Feb. 9, 2023]. Retrieved from Clarivate Analytics, 2018, 15 pages.

USPTO Office Action in U.S. Appl. No. 16/827,484 dated Mar. 15, 2023, 13 pages.

USPTO Office Action in U.S. Appl. No. 16/838,347 dated Jun. 8, 2023, 5 pages.

USPTO Office Action in U.S. Appl. No. 16/862,400 dated Mar. 22, 2023, 13 pages.

USPTO Office Action in U.S. Appl. No. 17/119,825 dated May 23, 2023, 19 pages.

USPTO Office Action in U.S. Appl. No. 17/119,830 dated Mar. 15, 2023, 23 pages.

USPTO Office Action in U.S. Appl. No. 17/558,481 dated Mar. 23, 2023, 49 pages.

Chinese Patent Office Decision of Rejection dated Oct. 10, 2022; Application No. 201880024597; 11 pages.

Chinese Patent Office Notification to Grant Patent Right for Invention dated Nov. 4, 2022; Application No. 201880056518.3; 2 pages.

Chinese Patent Office Second Office Action and Supplementary Search Report dated Apr. 25, 2022; Application No. 201880023218.5; 15 pages.

Chinese Patent Office Second Office Action and Supplementary Search Report dated Mar. 30, 2022; Application No. 201880024598; 15 pages.

Chinese Patent Office Second Office Action dated Jul. 13, 2022; Application No. 201880056518.3; 6 pages.

Chinese Patent Office Supplemental Search Report dated Jul. 4, 2022, Application No. 201880056518.3, 4 pages.

Chinese Patent Office Third Office Action dated Oct. 20, 2022; Application No. 201880023218.5; 8 pages.

European Patent Office Communication under Rule 71(3) EPC dated Apr. 19, 2022, Application No. 18 850 236.3, 46 pages.

European Patent Office Communication under Rule 71(3) EPC dated Nov. 29, 2022, Application No. 18 783 814.9, 46 pages.

(56) References Cited

OTHER PUBLICATIONS

European Patent Office Communication Under Rule 71(3) EPC, Application No. 18 783 814.9 dated Aug. 11, 2022, 44 pages.
European Patent Office Extended Search Report dated Oct. 18, 2022, Patent Application No. 22181044.3-1122, 7 pages.
European Patent Office Notice of Intention to Grant, Application No. 18783814.9, Nov. 29, 2022, 8. pages.
Huang et al., "Interactive learning for sensitivity factors of a human-powered augmentation lower exoskeleton," 2015 IEEE/RSJ International Conference on Intelligent Robots and Systems (IROS), Sep. 28, 2015, 7 pages.
International Search Report and Written Opinion mailed Apr. 26, 2018, International Patent Application No. PCT/US2018/016729, filed Feb. 2, 2018, 7 pages.
International Search Report and Written Opinion mailed Aug. 26, 2021, Patent Application No. PCT/US2021/034444, 7 pages.
International Search Report and Written Opinion mailed Aug. 26, 2021, Patent Application No. PCT/US2021/034447, 7 pages.
International Search Report and Written Opinion mailed Aug. 26, 2021, Patent Application No. PCT/US2021/034593, 10 pages.
International Search Report and Written Opinion mailed Dec. 1, 2022, Patent Application No. PCT/US2022/075098, 12 pages.
International Search Report and Written Opinion mailed Dec. 1, 2022, Patent Application No. PCT/US2022/075099, 12 pages.
International Search Report and Written Opinion mailed Dec. 5, 2022, Patent Application No. PCT/US2022/075097, 11 pages.
International Search Report and Written Opinion mailed Dec. 6, 2018, International Patent Application No. PCT/US2018/048638, filed Aug. 29, 2018, 8 pages.
International Search Report and Written Opinion mailed Dec. 6, 2018, Patent Application No. PCT/US2018/048639, 7 pages.
International Search Report and Written Opinion mailed Dec. 6, 2022, Patent Application No. PCT/US2022/075095, 10 pages.
International Search Report and Written Opinion mailed Jul. 18, 2016, International Patent Application No. PCT/US2016/024366, filed Mar. 25, 2016, 7 pages.
International Search Report and Written Opinion mailed Jul. 19, 2018, International Patent Application No. PCT/US2018/027643, filed Apr. 13, 2018, 7 pages.
International Search Report and Written Opinion mailed Jun. 3, 2021, Patent Application No. PCT/US2021/019711, 12 pages.
International Search Report and Written Opinion mailed Mar. 30, 2021, Patent Application No. PCT/US2020/064647, 10 pages.
International Search Report and Written Opinion mailed Nov. 29, 2022, International Patent Application No. PCT/US2022/075094, filed Aug. 17, 2022, 11 pages.
International Search Report and Written Opinion mailed Nov. 29, 2022, International Patent Application No. PCT/US2022/075096, filed Aug. 17, 2022, 11 pages.
International Search Report and Written Opinion mailed Sep. 2, 2021, Patent Application No. PCT/US2021/034030, 9 pages.
International Search Report and Written Opinion mailed Sep. 2, 2021, Patent Application No. PCT/US2021/034450, 9 pages.
International Search Report and Written Opinion mailed Sep. 9, 2021, Patent Application No. PCT/US2021/034443, 8 pages.
International Search Report and Written Opinion mailed Sep. 9, 2021, Patent Application No. PCT/US2021/034579, 8 pages.
International Search Report and Writtent Opinion mailed Aug. 26, 2021, Patent Application No. PCT/US2021/034468, 8 pages.
Israel Notice of Deficiencies for Patent Application No. 269860 dated Jul. 25, 2022, 5 pages.
Japan Final Office Action and Decision to Reject Amendment of Application No. 2019-554877 dated Nov. 7, 2022, 4 pages.
Japan Final Rejection of Application No. 2019-563328 dated Jul. 6, 2022, 2 pages.
Japan Patent Office, "Final Rejection" in Applicaiton No. 2019-563328, Sep. 9, 2022, 4 pages.
Japanese IPO Final Rejection of Application No. 2019-563328, Aug. 9, 2022, 2 pages.
Japanese IPO Notification of Reason for Rejection of Application No. 2020-512042, Jun. 27, 2022, 2 pages.
National Intellectual Property Administration, P. R. China, "2nd Office Action" in Application No. 201880023218.5, Apr. 25, 2022, 15 pages.
Notification of Grant of Chinese Patent Application No. 201880056709 dated May 18, 2022, 2 pages.
Tamez-Duque et al., "Real-time strap pressure sensor system for powered exoskeletons," Sensors 15(2):4550-4563, Feb. 2015.
Taniguchi, "Flexible Artificial Muscle Actuator Using Coiled Shape Memory Alloy Wires," APCBEE Procedia 7:54-59, Jan. 1, 2013.
Chinese Patent Office First Office Action dated Jun. 16, 2023; Application No. 202111540872.3; 14 pages.
Chinese Patent Office Notification to Grant Patent Right for Invention dated Jul. 10, 2023; Application No. 201880024597.X; 2 pages.
Chinese Patent Office Notification to Grant Patent Right for Invention dated Sep. 6, 2023; Application No. 201880023218.5; 2 pages.
European Patent Office Notice of Intention to Grant, Application No. 18748599.0, Aug. 16, 2023, 52 pages.
Israel Notice before Acceptance for Patent Application No. 282165 dated May 24, 2023, 3 pages.
Israel Notice Notice before Acceptance for Patent Application No. 282165 dated Apr. 18, 2023, 3 pages.
Japan PTO Rejection of Application No. 2019-563328 dated Jul. 13, 2023, 3 pages.
USPTO Non-Final Office Action in U.S. Appl. No. 17/327,121 dated Aug. 29, 2023, 8 pages.
USPTO Notice of Allowance of U.S. Appl. No. 17/729,934 dated Aug. 23, 2023, 22 pages.
USPTO Office Action in U.S. Appl. No. 16/838,347 dated Jan. 24, 2023, 7 pages.
USPTO Office Action in U.S. Appl. No. 17/327,121 dated Aug. 29, 2023, 8 pages.
USPTO Office Action in U.S. Appl. No. 17/332,172 dated Oct. 25, 2023, 39 pages.
USPTO Office Action in U.S. Appl. No. 17/332,507 dated Nov. 8, 2023, 23 pages.
USPTO Office Action in U.S. Appl. No. 17/332,818 dated Nov. 13, 2023, 29 pages.
European Patent Office Extended Search Report dated Jan. 29, 2024, Application No. 23196713.4, 7 pages.
European Patent Office Extended Search Report, Application No. 21813358.5 dated Jan. 24, 2024, 9 pages.
European Patent Office Supplementary Search Report dated Jan. 30, 2024, Application No. 21814414.5, 12 pages.
European Patent Office Supplementary Search Report, Application No. 21814414.5, 12 pages.
Israel Notice of Deficiencies for Patent Application 269860 dated Jan. 10, 2024, 4 pages.
Israel Notice of Deficiencies for Patent Application 269860 dated Nov. 14, 2023, 4 pages.
Japan IPO Office Action dated Feb. 13, 2024, Application No. 2022-573515, 5 pages.
Japan Office Action, Application No. 2022-573514 dated Dec. 27, 2023, 3 pages.
Japan Office Action, Application No. 2022-573520 dated Jan. 4, 2024, 4 pages.
Japan Office Action, Application No. 2023-034202 dated Jan. 9, 2024, 4 pages.
Japan PTO Rejection of Application No. 2022-573509 dated Dec. 4, 2023, 5 pages.
Japan PTO Rejection of Application No. 2022-573517 dated Jan. 9, 2024, 2 pages.
Japan PTO Rejection of Application No. 2022-573519 dated Jan. 9, 2024, 2 pages.
Japanese IPO Notification of Reason for Rejection of Application No. 2022-573516, Jan. 15, 2024, 3 pages.
USPTO Office Action in U.S. Appl. No. 16/827,484 dated Dec. 4, 2023, 18 pages.
Canadian Intellectual Property Office Office Action dated Dec. 6, 2024, Application No. 3,072,504, 6 pages.
Canadian IPO Notice of Allowance dated Mar. 19, 2024, Patent Application No. 3,051,105, 1 page.

(56) References Cited

OTHER PUBLICATIONS

Canadian IPO Office Action dated Dec. 5, 2024, Patent Application No. 3,072,622, 7 pages.
Canadian IPO Office Action dated Jun. 27, 2024 in Application No. 3,055,435, 5 pages.
Chinese Patent Office First Office Action dated Aug. 28, 2025; Application No. 202311193851.8; 7 pages.
Chinese Patent Office First Office Action dated Feb. 19, 2025; Application No. 202210922312.2; 43 pages.
Chinese Patent Office First Office Action dated Jan. 15, 2025; Application No. 202180040509.7; 3 pages.
Chinese Patent Office First Office Action dated Jan. 17, 2025, Application No. 202180045080.0; 10 pages.
Chinese Patent Office First Office Action dated Jan. 17, 2025; Application No. 202180045078.3; 13 pages.
Chinese Patent Office First Office Action dated Jan. 17, 2025; Application No. 202180045079.8; 10 pages.
Chinese Patent Office First Office Action dated Jan. 17, 2025; Application No. 202189945078.3; 13 pages.
Chinese Patent Office First Office Action dated Mar. 1, 2025; Application No. 202180045052.9; 74 pages.
Chinese Patent Office First Office Action dated Mar. 5, 2025; Application No. 2021180043414.0; 61 pages.
Chinese Patent Office Notification of Grant of Application No. 20211150872.3, Nov. 19, 2024, 2 pages.
Chinese Patent Office Notification of Grant of Application No. 202111540872.3, Nov. 19, 2024, 2 pages.
Chinese Patent Office Notification to Grant Patent Right for Invention dated Jul. 4, 2024; Application No. 2022-573514; 1 page.
Chinese Patent Office Second Office Action dated Aug. 9, 2025; Application No. 202080091082.0; 6 pages.
Chinese Patent Office Second Office Action dated Sep. 1, 2025; Application No. 202180040509.7; 11 pages.
Chu, "Human-Expsystem Adaptation," MIT School of Engineering, Oct. 2018 [retrieved Apr. 25, 2024 from https://engineering.mit.edu/engage/engineering-in-action/human-exosystem-adaptation/,] 9 pages.
Dephy, "Build Faster a Safe Robotics Platform that Actually Works?" Retrieved Apr. 25, 2024 from https://web.archive.org/web/20221226232116/https://dephy.com/faster/, 11 pages.
Dephy, "Getting Started," retrieved May 28, 2024 from https://dephy.com/start/, 23 pages.
European Patent Office Communication under Rule 71(3) EPC dated Jun. 20, 2025, Application No. 22 181 044.3, 42 pages.
European Patent Office Exam Report dated Jan. 14, 2025, Application No. 22181044.3, 4 pages.
European Patent Office Exam Report dated May 14, 2025, Application No. 21 814 414.5, 5 pages.
European Patent Office Extended Search Report dated Apr. 4, 2025 for Application No. 22859359.6, 10 pages.
European Patent Office Extended Search Report dated Apr. 8, 2024, Application No. 20899495.4, 10 pages.
European Patent Office Extended Search Report dated Jun. 12, 2024, Application No. 21812817.1, 12 pages.
European Patent Office Extended Search Report dated Jun. 17, 2024, Application No. 21814117.4, 7 pages.
European Patent Office Extended Search Report dated Jun. 21, 2024, Patent Application No. 21812103.6, 12 pages.
European Patent Office Extended Search Report dated Mar. 27, 2025, Application No. 22859360.4, 11 pages.
European Patent Office Extended Search Report dated May 28, 2024, Application No. 21814414.5, 11 pages.
European Patent Office Extended Search Report, Application No. 21812695.1 dated Jun. 18, 2024, 10 pages.
European Patent Office Extended Search Report, Application No. 21812810.6 dated Jan. 18, 2024, 8 pages.
European Patent Office Extended Search Report, Application No. 21812992.2 dated Jun. 21, 2024, 11 pages.
European Patent Office Extended Search Report, Application No. 22859361.2 dated Mar. 27, 2025, 11 pages.
European Patent Office Notice of Intention to Grant dated Mar. 27, 2025, Application No. 20899495.4, 71 pages.
European Patent Office Notice of Intention to Grant, Application No. 18851608.2, Mar. 25, 2025, 56 pages.
European Patent Office Notice of Intention to Grant, Application No. 20899495.4, dated Feb. 27, 2025, 73 pages.
European Patent Office Notice of Intention to Grant, Application No. 21814117.4, May 26, 2025, 123 pages.
European Patent Office, "Intention to Grant" in application No. 21 814 117.4-1002, May 26, 2025, 123 pages.
Israel Notice of Acceptance dated Apr. 1, 2024, Patent Application No. 272623, 3 pages.
Israel Notice of Deficiencies for Patent Application 293829 dated Dec. 9, 2024, 5 pages.
Israel Notice of Deficiencies for Patent Application 298446 dated May 27, 2025, 5 pages.
Israel Notice of Deficiencies for Patent Application 298455 dated May 29, 2025, 3 pages.
Israel Notice of Deficiencies for Patent Application No. 295817 dated Jul. 24, 2023, 4 pages.
Israel Notice of Deficiencies for Patent Application No. 298452 dated May 5, 2025, 4 pages.
Israel Notice of Deficiencies for Patent Application No. 298465 dated May 22, 2025, 4 pages.
Isreal Patent Office, "Office Action" in Application No. 298446, May 27, 2025, 5 pages.
Isreal Patent Office, "Office Action" in Application No. 298455, May 29, 2025, 3 pages.
Isreal Patent Office, "Office Action" in Application No. 298465, May 22, 2025, 4 pages.
Japan Decision to Grant Application No. 2022-176048 dated Nov. 14, 2024, 2 pages.
Japan Decision to Grant Application No. 2022-573509 dated Aug. 22, 2024, 2 pages.
Japan First Office Action, Application No. 2022-573518 dated Apr. 22, 2024, 2 pages.
Japan IPO Office Action dated Aug. 13, 2024, Application No. 2022-176048, 2 pages.
Japan IPO Trial Decision Allowing Application No. 2019-554877 dated Apr. 1, 2024, 2 pages.
Japan Notice of Patent Grant, Application No. 2022-573519 dated Aug. 8, 2024, 1 page.
Japan Office Action dated Feb. 3, 2025, Application No. 2023-017338, 2 pages.
Japan Office Action, Application No. 2023-017338 dated Aug. 26, 2024, 3 pages.
Japan Office Action, Application No. 2023-017338 dated Nov. 9, 2023, 4 pages.
Japan Patent Office Notification to Grant Patent Right for Invention dated Jul. 4, 2024; Application No. 2022-573514; 1 page.
Japan Patent Office, "Decision to Grant" in application No. 2022-573515, Sep. 30, 2024, 1page.
Japan Patent Office, "Decision to Grant" in application No. 2022-573516, Sep. 19, 2024, 1page.
Japan Trial Decision Notice of Patentability of Application No. 2019-563328 dated Aug. 13, 2024, 2 pages.
Japanese IPO Notice of Decision to Grant Application No. 2023-017338, Aug. 4, 2025, 1 page.
Khalili, et al., "Studies on Practical Applications of Safe-Fall Control Strategies for Lower Limb Exoskeletons*," 2019 IEEE 16th INternational Conference on Rehabilitation Robotics, Jan. 24-28, 2019, 6 pages.
MIT School of Engineering, "Human-exosystem Adaptation," https://www.youtube.com/watch?v=GXGHi_n1uR0, Oct. 4, 2018, 2 pages.
University of Michigan, "Understanding Exoskeletons Use Motivation," 2020 [retrieved Apr. 25, 2024 from https://neurobionics.robotics.umich.edu/research/biomechanical-science/dephy-ankle-exoskeletons/,] 4 pages.
USPTO Final Office Action dated Apr. 9, 2025, U.S. Appl. No. 17/329,632, 25 pages.
USPTO Final Office Action dated Aug. 14, 2024, U.S. Appl. No. 17/332,507, 29 pages.

(56) References Cited

OTHER PUBLICATIONS

USPTO Final Office Action dated Nov. 7, 2025, U.S. Appl. No. 16/838,347, 7 pages.
USPTO Final Office Action dated Sep. 25, 2024, U.S. Appl. No. 17/119,825, 24 pages.
USPTO Non-Final Office Action dated Jul. 25, 2025, U.S. Appl. No. 17/889,603, 20 pages.
USPTO Notice of Allowance dated May 23, 2025, U.S. Appl. No. 17/890,070, 5 pages.
USPTO Notice of Allowance in U.S. Appl. No. 17/119,825 dated Feb. 10, 2025, 8 pages.
USPTO Notice of Allowance in U.S. Appl. No. 17/332,172 dated Aug. 25, 2025, 21 pages.
USPTO Notice of Allowance in U.S. Appl. No. 17/890,070 dated Jul. 10, 2025, 18 pages.
USPTO Notice of Allowance in U.S. Appl. No. 17/890,070 dated May 23, 2025, 55 pages.
USPTO Notice of Allowance of U.S. Appl. No. 17/331,956 dated Jun. 25, 2025, 5 pages.
USPTO Notice of Allowance of U.S. Appl. No. 17/889,750 dated Jun. 11, 2024, 9 pages.
USPTO Office Action dated Apr. 4, 2024, U.S. Appl. No. 16/838,347, 7 pages.
USPTO Office Action dated Aug. 14, 2024, U.S. Appl. No. 17/332,818, 35 pages.
USPTO Office Action dated Aug. 26, 2025, U.S. Appl. No. 17/332,203, 23 pages.
USPTO Office Action Dated Aug. 28, 2024, U.S. Appl. No. 17/331,956, 21 pages.
USPTO Office Action dated Jan. 23, 2025, U.S. Appl. No. 17/331,961, 25 pages.
USPTO Office Action dated Jul. 31, 2024, U.S. Appl. No. 17/331,961, 20 pages.
USPTO Office Action dated Jun. 14, 2024, U.S. Appl. No. 17/558,481, 15 pages.
USPTO Office Action dated Mar. 7, 2024, U.S. Appl. No. 17/119,825, 18 pages.
USPTO Office Action in U.S. Appl. No. 16/862,400 dated My 22, 2024, 20 pages.
USPTO Office Action in U.S. Appl. No. 17/185,754 dated Jun. 10, 2025, 21 pages.
USPTO Office Action in U.S. Appl. No. 17/327,121 dated Feb. 11, 2025, 8 pages.
USPTO Office Action in U.S. Appl. No. 17/329,632 dated Aug. 19, 2024, 20 pages.
USPTO Office Action in U.S. Appl. No. 17/332,172 dated Dec. 17, 2024, 39 pages.
USPTO Office Action in U.S. Appl. No. 17/332,507 dated Feb. 11, 2025, 26 pages.
USPTO Office Action in U.S. Appl. No. 17/332,818 dated Feb. 14, 2025, 28 pages.
USPTO Office Action in U.S. Appl. No. 17/558,481 dated Dec. 20, 2024, 12 pages.
USPTO Office Action in U.S. Appl. No. 17/889,570 dated Sep. 30, 2025, 81 pages.
USPTO Office Action in U.S. Appl. No. 17/889,589 dated Aug. 12, 2025, 17 pages.
USPTO Notice of Allowance of U.S. Appl. No. 17/889,570 dated Apr. 10, 2026, 13 pages.
USPTO Office Action in U.S. Appl. No. 17/889,603 dated May 18, 2026, 24 pages.

* cited by examiner 600
620
145
630
622
1710
620
600
1740
PUSH
622
1705
RELEASE
110

622
620
600
630
1710
DISENGAGE
1730
1720
110

145
620
600
ROAM
110

145
620

110
130
145
620
600
ROAM

Fig.21a
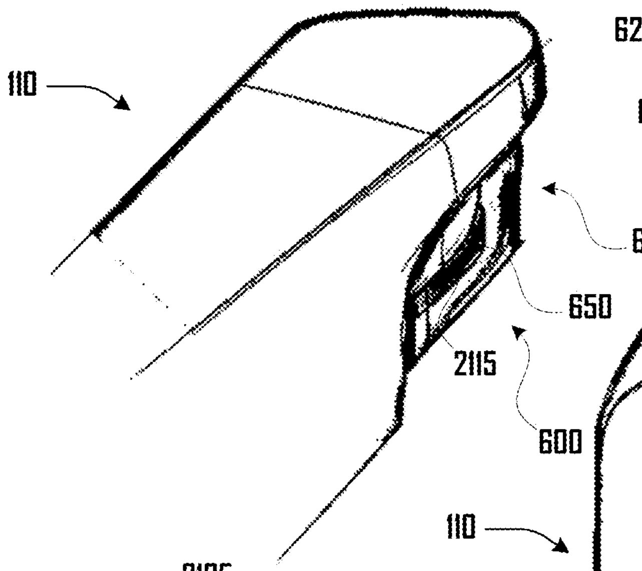
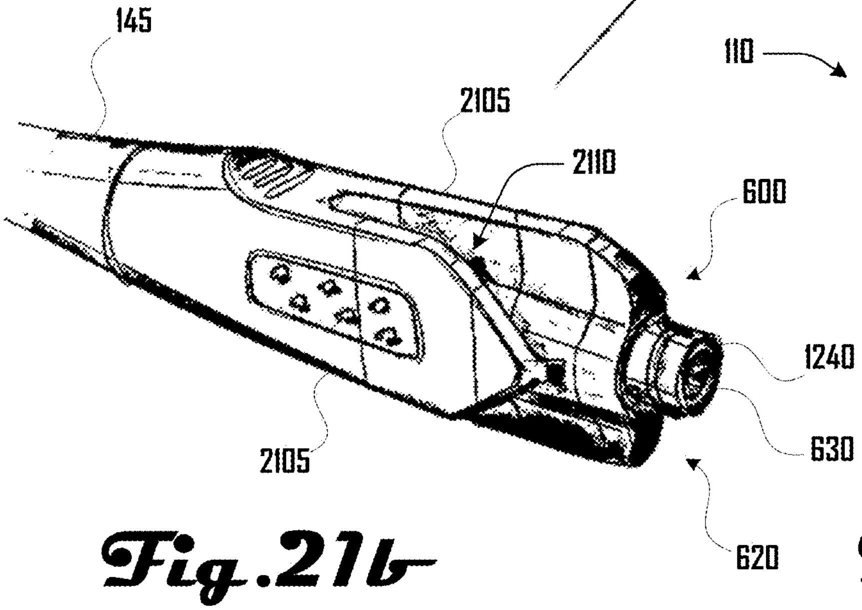
Fig.21b
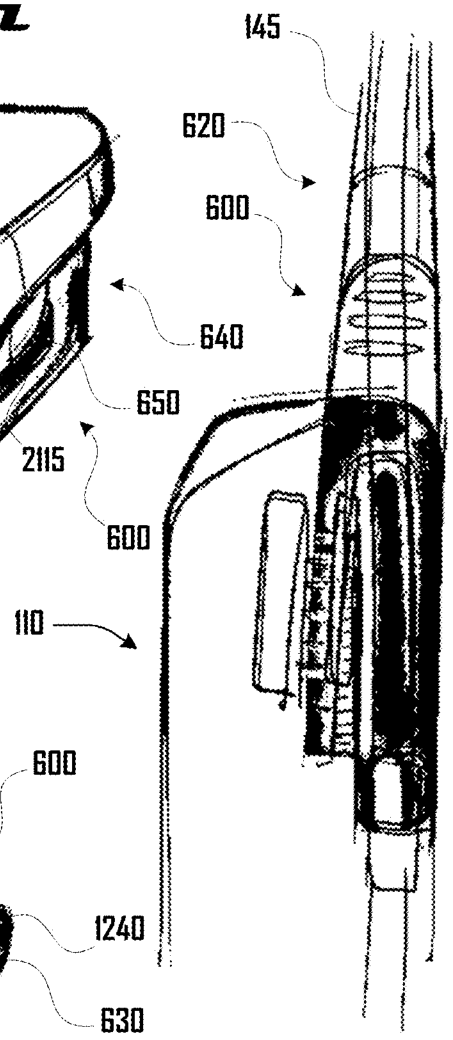
Fig.21c

UNIFIED PNEUMATIC AND ELECTRICAL CONNECTOR SYSTEM AND METHOD

CROSS-REFERENCE TO RELATED APPLICATIONS

This application is a non-provisional of and claims the benefit of U.S. Provisional Application No. 63/233,988, filed Aug. 17, 2021, entitled "UNIFIED PNEUMATIC AND ELECTRICAL CONNECTOR SYSTEM AND METHOD, ". This application is hereby incorporated herein by reference in its entirety and for all purposes.

This application is also a non-provisional of and claims the benefit of U.S. Provisional Application No. 63/233,976, filed Aug. 17, 2021, entitled "CABLE MANAGEMENT METHODS FOR A WEARABLE MOBILE ROBOT,". This application is hereby incorporated herein by reference in its entirety and for all purposes.

This application is also related to U.S. patent application Ser. No. 17/329,632, filed May 25, 2021, entitled "DIRECT DRIVE PNEUMATIC TRANSMISSION FOR A MOBILE ROBOT"; and is related to U.S. patent application Ser. No. 17/332,818, filed May 27, 2021, entitled "POWERED MEDICAL DEVICE AND METHODS FOR IMPROVED USER MOBILITY AND TREATMENT"; and is related to U.S. patent application Ser. No. 17/331,956, filed May 27, 2021, entitled "FIT AND SUSPENSION SYSTEMS AND METHODS FOR A MOBILE ROBOT"; and is related to U.S. patent application Ser. No. 17/331,961, filed May 27, 2021, entitled "BATTERY SYSTEMS AND METHODS FOR A MOBILE ROBOT,"; and is related to U.S. patent application Ser. No. 17/332,203, filed May 27, 2021, entitled "CONTROL SYSTEM AMD METHOD FOR A MOBILE ROBOT,"; and is related to U.S. patent application Ser. No. 17/332,172, filed May 27, 2021, entitled "USER INTERFACE AND FEEDBACK SYSTEMS AND METHODS FOR A MOBILE ROBOT,"; and is related to U.S. patent application Ser. No. 17/332,507, filed May 27, 2021, entitled "DATA LOGGING AND THIRD-PARTY ADMINISTRATION OF A MOBILE ROBOT,"; and is related to U.S. patent application Ser. No. 17/332,860, filed May 27, 2021, entitled "MODULAR EXOSKELETON SYSTEMS AND METHODS,", these applications are hereby incorporated herein by reference in their entirety for all purposes.

This application is also related to U.S. Non-Provisional application Ser. No. 17/889,570, filed contemporaneously herewith, entitled "ACTUATOR FEATURES TO IMPROVE FUNCTION OF A MOBILE ROBOT,"; is related to U.S. Non-Provisional application Ser. No. 17/889,575, filed contemporaneously herewith, entitled "CABLE MANAGEMENT SYSTEMS AND METHODS FOR A WEARABLE MOBILE,"; is related to U.S. Non-Provisional application Ser. No. 17/890,070, filed contemporaneously herewith, entitled "MOBILE POWER SOURCE FOR A MOBILE ROBOT,"; is related to U.S. Non-Provisional application Ser. No. 17/889,750, filed contemporaneously herewith, entitled "MARITIME APPLICATIONS FOR A MOBILE ROBOT,"; and is related to U.S. Non-Provisional application Ser. No. 17/889,603, filed contemporaneously herewith, entitled "DATA INFERENCES FROM A WEARABLE ROBOT,". These applications are hereby incorporated herein by reference in their entirety and for all purposes.

BRIEF DESCRIPTION OF THE DRAWINGS

FIGS. 21*a*, 21*b* and 21*c* illustrate another example of a cable connector with a first connector side that plugs directly into a second connector side of actuator unit.

Figure 1:
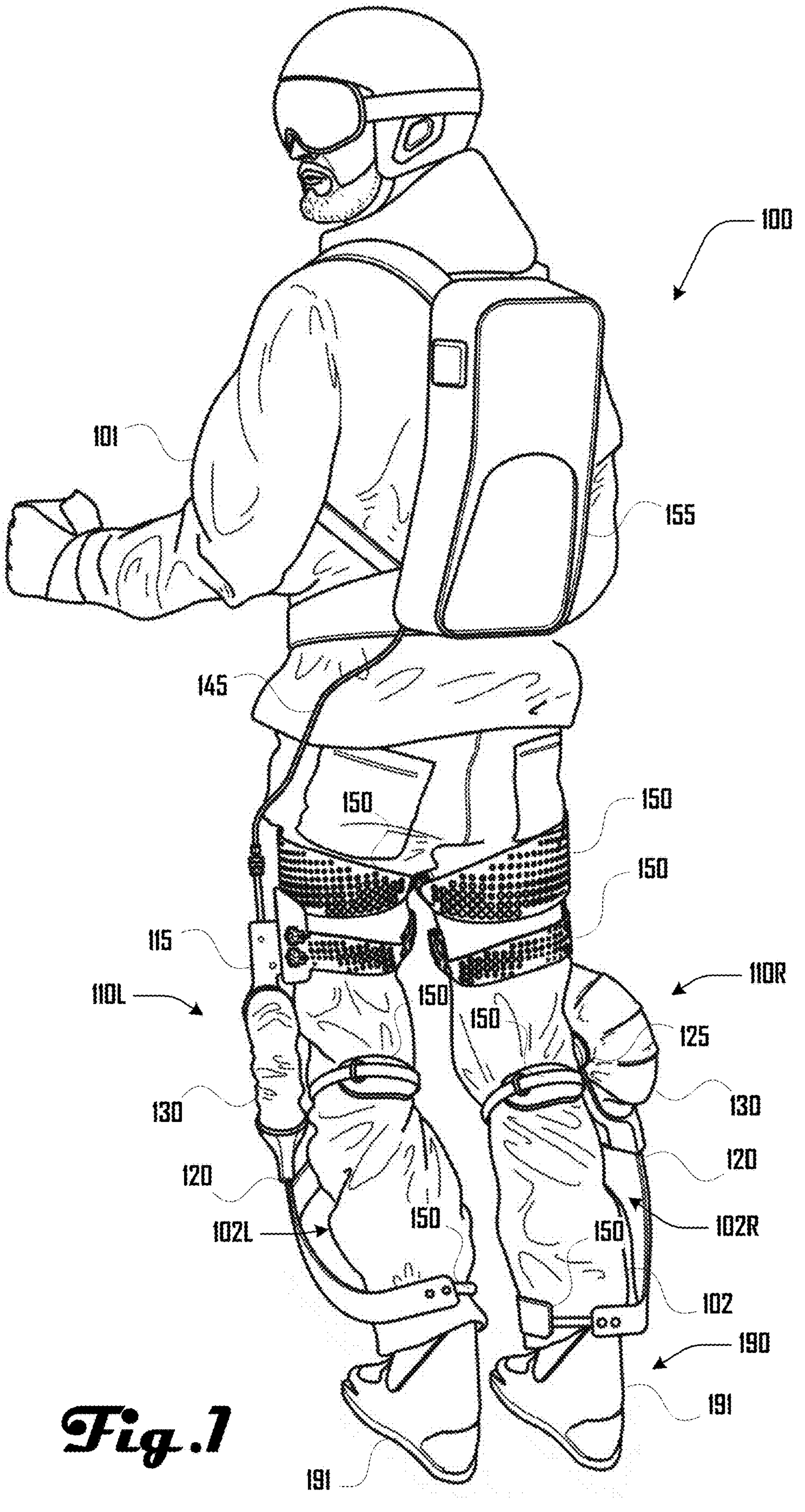
FIG. 1 is an example illustration of an embodiment of an exoskeleton system being worn by a user.

It should be noted that the figures are not drawn to scale and that elements of similar structures or functions are generally represented by like reference numerals for illustrative purposes throughout the figures. It also should be noted that the figures are only intended to facilitate the description of the preferred embodiments. The figures do not illustrate every aspect of the described embodiments and do not limit the scope of the present disclosure.

DETAILED DESCRIPTION OF THE PREFERRED EMBODIMENTS

The following disclosure also includes example embodiments of the design of novel exoskeleton devices. Various preferred embodiments include: a leg brace with integrated actuation, a mobile power source and a control unit that determines the output behavior of the device in real-time. In various embodiments, a brace uses a fluidic actuator to help the user move. In order to function, in some examples the brace needs a power and fluid supply and the ability to communicate to receive and send data. In one embodiment, the system can comprise, consist essentially of or consist of a power pack strapped onto the torso of the user and one or more braces worn around the knee(s) of the user. These two components can be connected together in various embodiments so that the brace may communicate with the power pack and/or receive power and fluid from the power pack. This is done in some examples through the use of power and fluidic cables on both components.

The connection between the cables of the two components can be an important part of the system in some embodiments. In various examples, the cables from each component end and meet at the connector end and come in contact at their connector faces. The connector faces can have the electrical and fluidic contacts so that the electrical power data and fluids may travel through this meeting. It can be desirable in various embodiments for the connection to be strong so it is not easily broken or disconnected unintentionally, but be simple to disconnect so that most or all users can easily do it themselves without excessive strength. In can be desirable in various embodiments for the connection to use specific components so it is prepared for scenarios when an accidental breakage occurs such as when a cable is snagged on an object.

In a preferred method, magnets are used to hold the connection. In such an embodiment, (e.g., circular) magnets that attract each other are placed on each of the connector faces. The magnetic forces attracting the magnets together can help make it easier to connect the electrical and fluidic contacts at the connector. The attractive magnetic forces can pull the connector faces together and keep them connected with little effort from the user in some examples. The amount of force from the magnet can be controlled in various embodiments by the size of each magnet and the distance between them. Magnets may be used on both faces, or only one connector face may use a magnet or multiple magnets which are attracted to a metal on the other face.

In embodiments with connector retention elements such as magnets or latches, it can be desirable for such elements to not only hold the connector ends together, but to also have the ability to break away when unintentional forces are applied. The electrical contact options on the connector face can include spring-loaded pins, concentric rings, or pin and sockets, and in various examples it can be desirable for such elements to come apart with ease when separated. In full intentional and uninterrupted operation, in various embodiments it can be desirable for the connector to function properly with ease with little damage through daily handling and movement by the user. Size, shape, flexibility and the like can be considerations made to optimize user experience. In addition to the components, there are many possible layouts of the components on the connector face, and it can be desirable in various embodiments for such a layout of components to facilitate the ease of connection and disconnection. In the following disclosure, various example embodiments are described that can include a connector to connect a power pack and brace, which may be configured in a variety of suitable ways.

In various embodiments, it can be desirable for the connection to be easily released when the user wants to separate the components. It can be desirable for the release method to provide a mechanical advantage by requiring little force to activate, but releasing the larger force holding the connection.

In some embodiments, the user presses a button to separate the connection. In a preferred embodiment, the button may be a cam which pushes the mated connectors apart. In such an embodiment, the connector faces can be held together with magnets and the cam can separate the connector faces enough to release the magnetic hold.

In another embodiment, the connector may be locked together by a latch and pressing the button may release the latch and separate the connector parts. In such an embodiment, a small force is required to press the button, which can release the higher force holding the connector. In another embodiment, the release can be achieved by twisting the two parts apart such as a turn latch or screw connection. In another embodiment, the connector has finger loops for the user to place their fingers in and the release can be achieved by pulling the connector apart. In such an embodiment, the force required to separate the connector can be equal to the force holding it together, which means there may be no mechanical advantage achieved with this embodiment. Various other release methods may be used, including but not limited to twist action, wedge action, transverse sliding action, or thumbscrew. The release method can be configured to fit the application and the intended user.

In one example scenario, a user is able to operate the connector with just one hand. Various features can be implemented in various examples to help make one-handed operation easier. As mentioned above, the mechanical advantages of a release button in some examples can require little force to press, and can help the user detach it with less force. In one embodiment, the cables are semi-stiff to make the connector portion more easily accessible. Another helpful feature for one-handed operation in some embodiments can be where the mating surfaces are highly asymmetrical. This can allow the user to confidently mate the plugs, without looking, and without using their second hand. Further, the connector may have magnets in some examples, which can help pull the connector faces together with little effort from the user. Other features that can enhance one-handed operation in some embodiments can include ergonomic grips, over-molded grips, or distinct surface shapes. Various embodiments can use the options listed above or combinations and variants thereof, but are in no way limited to the explicitly stated combinations of methods and items.

In some scenarios, it can be desirable for the connector to be configured to disconnect without action from the user (e.g., in order to avoid damage). One scenario may be when a cable gets caught on an object without the user knowing, and the user continues moving, creating tension on the cable, and pulling on the connector. This can result in damage to the cables or electronics, and even personal injury if the user trips or falls. An easy breakaway feature of the connector in some example can not only reduce product damage, but can also increase user safety by preventing trips or falls. In a preferred embodiment, the connector is held together by magnets. In one example, when a tension force on the cables exceeds the magnet strength, the connector ends will separate without the need to overcome any physical block, such as a hook or latch, and reduce the likelihood of damage to components. In another embodiment, weakened snap hooks are used to hold the connector together. The snap hooks in some examples can be disengaged with a sufficiently forceful pull, without damage to the hooks. Other breakaway features that can help reduce damage in various embodiments can include weakened latches, weakened snap hooks, a spring-loaded latch, hook and loop tape (e.g., Velcro), disposable and replaceable breaking components, or detents.

In addition to being able to break away with no damage, it can be desirable in some embodiments for the fluidic valve be shut when the connector is disconnected. If there is no shutoff for the fluidic valve, on various examples it may continue to release fluid, causing more issues. In a preferred embodiment, the fluidic connection has a spring-loaded valve, which only allows fluid to flow through the connector and cables when the spring is compressed. When the fluidic connection is no longer connected, the spring can be released and the passageway for the fluid is closed. Various other methods, not mentioned above, for automatically shutting off the fluidic valve can be used, such as a discrete shutoff valve elsewhere in the system. In such an embodiment, the electrical contacts can separate before the fluidic contact, and the system can detect that the connector has been unmated, and can send a signal to shut off the valve. The shutoff valve can be located in various locations, such as inside the power pack, in the middle of the cable, or in the connector itself.

A component of an exoskeleton system that is present in various embodiments is a body-worn, lower-extremity brace that incorporates the ability to introduce torque to the user. One preferred embodiment of this component is a leg brace that is configured to support the knee of the user and includes actuation across the knee joint to provide assistance torques in the extension direction. This embodiment can connect to the user through a series of attachments including one on the boot, below the knee, and along the user's thigh. This preferred embodiment can include this type of leg brace on both legs of the user.

The present disclosure teaches example embodiments of a fluidic exoskeleton system that includes one or more adjustable fluidic actuators. Some preferred embodiments include a fluidic actuator that can be operated at various pressure levels with a large stroke length in a configuration that can be oriented with a joint on a human body.

Figure 2:
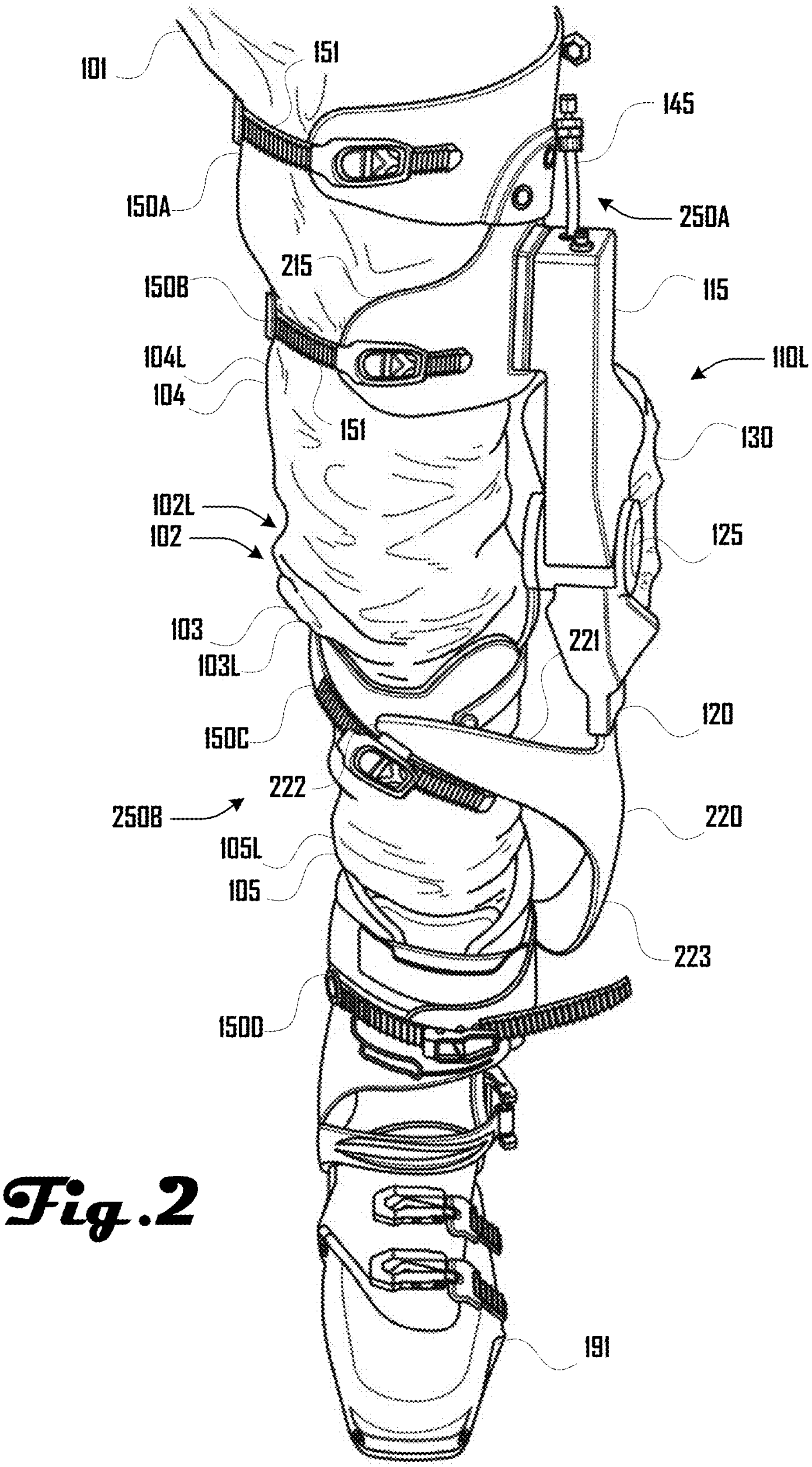
FIG. 2 is a front view of an embodiment of a leg actuation unit coupled to one leg of a user.
Figure 3:
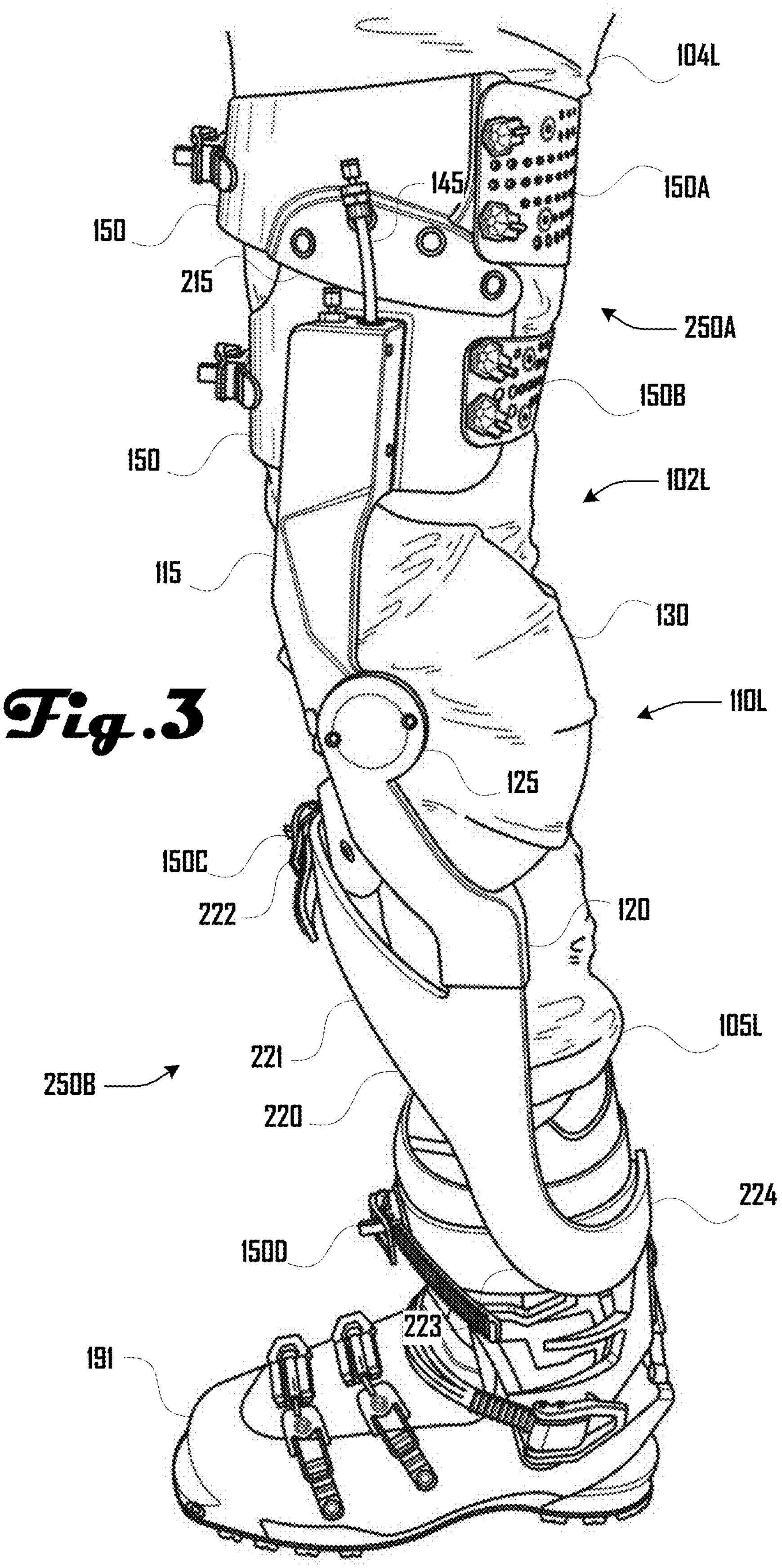
FIG. 3 is a side view of the leg actuation unit of FIG. 3 coupled to the leg of the user.
Figure 4:
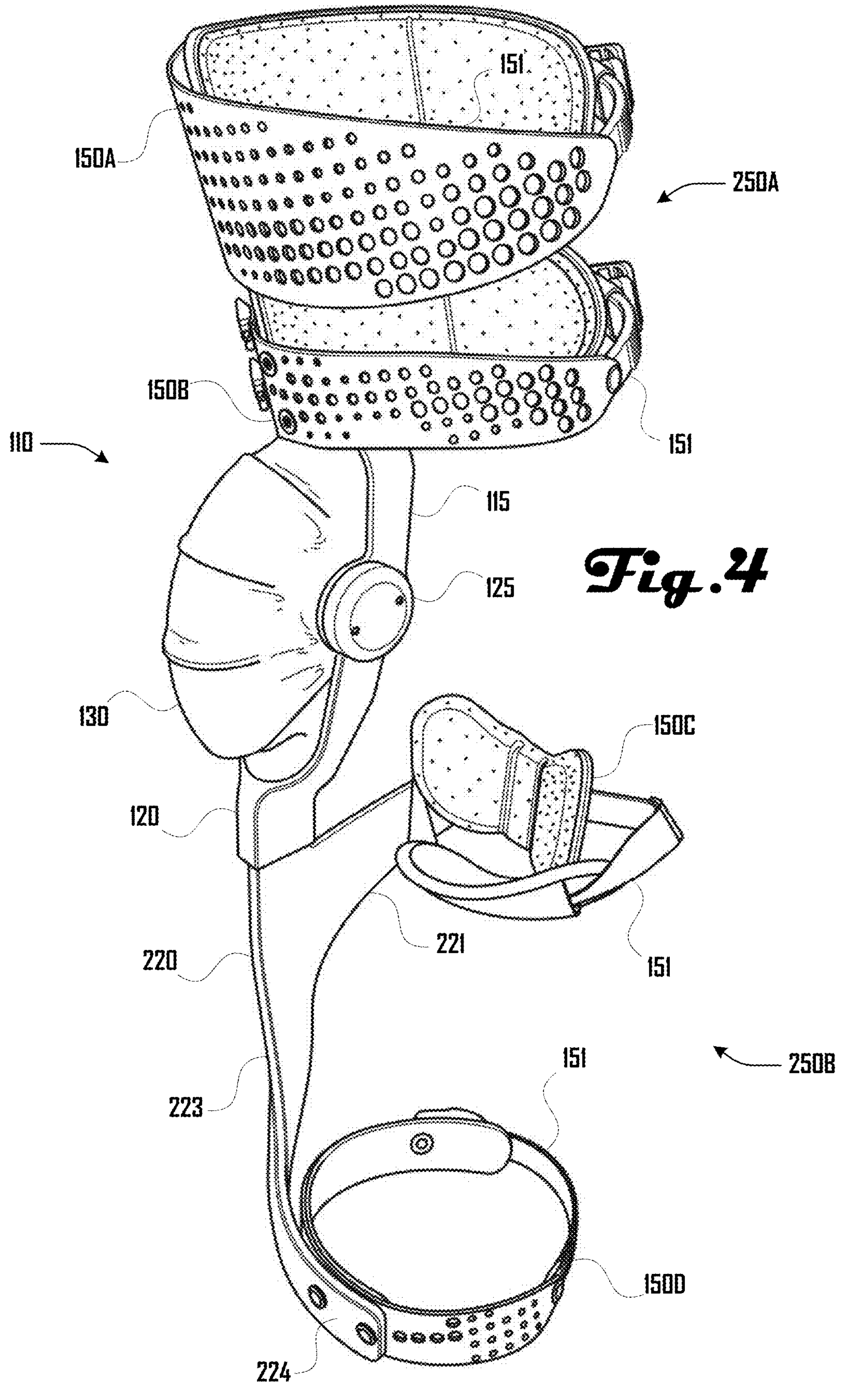
FIG. 4 is a perspective view of the leg actuation unit of FIGS. 3 and 4.

As discussed herein, an exoskeleton system 100 can be configured for various suitable uses. For example, FIGS. 1-3 illustrate an exoskeleton system 100 being used by a user. As shown in FIG. 1 the user 101 can wear the exoskeleton system 100 on both legs 102. FIGS. 2 and 3 illustrate a front and side view of an actuator unit 110 coupled to a leg 102 of a user 101 and FIG. 4 illustrates a side view of an actuator unit 110 not being worn by a user 101.

As shown in the example of FIG. 1, the exoskeleton system 100 can comprise a left and right leg actuator unit 110L, 110R that are respectively coupled to a left and right leg 102L, 102R of the user. In various embodiments, the left and right leg actuator units 110L, 110R can be substantially mirror images of each other.

As shown in FIGS. 1-4, leg actuator units 110 can include an upper arm 115 and a lower arm 120 that are rotatably coupled via a joint 125. A bellows actuator 130 extends between the upper arm 115 and lower arm 120. One or more sets of cables 145 can be coupled to the bellows actuator 130 to introduce and/or remove fluid from the bellows actuator 130 to cause the bellows actuator 130 to expand and contract and to stiffen and soften, as discussed herein. As discussed herein, in various embodiments, such cables 145 can transmit power, communication signals, and the like to and/or from one or more bellows actuators 130. A backpack 155 can be worn by the user 101 and can hold various components of the exoskeleton system 100 such as a fluid source, control system, a power source, pneumatic system, and the like (see e.g., FIG. 5).

As shown in FIGS. 1-3, the leg actuator units 110L, 110R can be respectively coupled about the legs 102L, 102R of the user 101 with the joints 125 positioned at the knees 103L, 103R of the user 101 with the upper arms 115 of the leg actuator units 110L, 110R being coupled about the upper leg portions 104L, 104R of the user 101 via one or more couplers 150 (e.g., straps that surround the legs 102). The lower arms 120 of the leg actuator units 110L, 110R can be coupled about the lower leg portions 105L, 105R of the user 101 via one or more couplers 150.

The upper and lower arms 115, 120 of a leg actuator unit 110 can be coupled about the leg 102 of a user 101 in various suitable ways. For example, FIGS. 1-3 illustrate an example where the upper and lower arms 115, 120 and joint 125 of the leg actuator unit 110 are coupled along lateral faces (sides) of the top and bottom portions 104, 105 of the leg 102. As shown in the example of FIGS. 1-3, the upper arm 115 can be coupled to the upper leg portion 104 of a leg 102 above the knee 103 via two couplers 150 and the lower arm 120 can be coupled to the lower leg portion 105 of a leg 102 below the knee 103 via two couplers 150.

Specifically, the upper arm 115 can be coupled to the upper leg portion 104 of the leg 102 above the knee 103 via a first set of couplers 250A that includes a first and second coupler 150A, 150B. The first and second couplers 150A, 150B can be joined by a rigid plate assembly 215 disposed on a lateral side of the upper leg portion 104 of the leg 102, with straps 151 of the first and second couplers 150A, 150B extending around the upper leg portion 104 of the leg 102. The upper arm 115 can be coupled to the plate assembly 215 on a lateral side of the upper leg portion 104 of the leg 102, which can transfer force generated by the upper arm 115 to the upper leg portion 104 of the leg 102.

The lower arm 120 can be coupled to the lower leg portion 105 of a leg 102 below the knee 103 via a second set of couplers 250B that includes a third and fourth coupler 150C, 150D. A coupling branch unit 220 can extend from a distal end of, or be defined by a distal end of the lower arm 120. The coupling branch unit 220 can comprise a first branch 221 that extends from a lateral position on the lower leg portion 105 of the leg 102, curving upward and toward the anterior (front) of the lower leg portion 105 to a first attachment 222 on the anterior of the lower leg portion 105 below the knee 103, with the first attachment 222 joining the third coupler 150C and the first branch 221 of the coupling branch unit 220. The coupling branch unit 220 can comprise a second branch 223 that extends from a lateral position on the lower leg portion 105 of the leg 102, curving downward and toward the posterior (back) of the lower leg portion 105 to a second attachment 224 on the posterior of the lower leg portion 105 below the knee 103, with the second attachment 224 joining the fourth coupler 150D and the second branch 223 of the coupling branch unit 220.

As shown in the example of FIGS. 1-3, the fourth coupler 150D can be configured to surround and engage the boot 191 of a user. For example, the strap 151 of the fourth coupler 150D can be of a size that allows the fourth coupler 150D to surround the larger diameter of a boot 191 compared to the lower portion 105 of the leg 102 alone. Also, the length of the lower arm 120 and/or coupling branch unit 220 can be of a length sufficient for the fourth coupler 150D to be positioned over a boot 191 instead of being of a shorter length such that the fourth coupler 150D would surround a section of the lower portion 105 of the leg 102 above the boot 191 when the leg actuator unit 110 is worn by a user.

Attaching to the boot 191 can vary across various embodiments. In one embodiment, this attachment can be accomplished through a flexible strap that wraps around the circumference of boot 191 to affix the leg actuator unit 110 to the boot 191 with the desired amount of relative motion between the leg actuator unit 110 and the strap. Other embodiments can work to restrict various degrees of freedom while allowing the desired amount of relative motion between the leg actuator unit 110 and the boot 191 in other degrees of freedom. One such embodiment can include the use of a mechanical clip that connects to the back of the boot 191 that can provide a specific mechanical connection between the device and the boot 191. Various embodiments can include but are not limited to the designs listed previously, a mechanical bolted connection, a rigid strap, a magnetic connection, an electro-magnetic connection, an electromechanical connection, an insert into the user's boot, a rigid or flexible cable, or a connection directly to a boot.

Another aspect of the exoskeleton system 100 can be fit components used to secure the exoskeleton system 100 to the user 101. Since the function of the exoskeleton system 100 in various embodiments can rely heavily on the fit of the exoskeleton system 100 efficiently transmitting forces between the user 101 and the exoskeleton system 100 without the exoskeleton system 100 significantly drifting on the body 101 or creating discomfort, improving the fit of the exoskeleton system 100 and monitoring the fit of the exoskeleton system 100 to the user over time can be desirable for the overall function of the exoskeleton system 100 in some embodiments.

In various examples, different couplers 150 can be configured for different purposes, with some couplers 150 being primarily for the transmission of forces, with others being configured for secure attachment of the exoskeleton system 100 to the body 101. In one preferred embodiment for a single knee system, a coupler 150 that sits on the lower leg 105 of the user 101 (e.g., one or both of couplers 150C, 150D) can be intended to target body fit, and as a result, can remain flexible and compliant to conform to the body of the user 101. Alternatively, in this embodiment a coupler 150 that affixes to the front of the user's thigh on an upper portion 104 of the leg 102 (e.g., one or both of couplers 150A, 150B) can be intended to target power transmission needs and can have a stiffer attachment to the body than other couplers 150 (e.g., one or both of couplers 150C, 150D). Various embodiments can employ a variety of strapping or coupling configurations, and these embodiments can extend to include any variety of suitable straps, couplings, or the like, where two parallel sets of coupling configurations are meant to fill these different needs.

In some cases, the design of the joint 125 can improve the fit of the exoskeleton system 100 on the user. In one embodiment, the joint 125 of a single knee leg actuator unit 110 can be designed to use a single pivot joint that has some deviations with the physiology of the knee joint. Another embodiment uses a polycentric knee joint to better fit the motion of the human knee joint, which in some examples can be desirably paired with a very well fit leg actuator unit 110. Various embodiments of a joint 125 can include but are not limited to the example elements listed above, a ball and socket joint, a four-bar linkage, and the like.

Some embodiments can include fit adjustments for anatomical variations in *varus* or valgus angles in the lower leg 105. One preferred embodiment includes an adjustment incorporated into a leg actuator unit 110 in the form of a cross strap that spans the joint of the knee 103 of the user 101, which can be tightened to provide a moment across the knee joint in the frontal plane which varies the nominal resting angle. Various embodiments can include but are not limited to the following: a strap that spans the joint 125 to vary the operating angle of the joint 125; a mechanical assembly including a screw that can be adjusted to vary the angle of the joint 125; mechanical inserts that can be added to the leg actuator unit 110 to discreetly change the default angle of the joint 125 for the user 101, and the like.

In various embodiments, the leg actuator unit 110 can be configured to remain suspended vertically on the leg 102 and remain appropriately positioned with the joint of the knee 103. In one embodiment, a coupler 150 associated with a boot 191 (e.g., coupler 150D) can provide a vertical retention force for a leg actuator unit 110. Another embodiment uses a coupler 150 positioned on the lower leg 105 of the user 101 (e.g., one or both of couplers 150C, 150D) that exerts a vertical force on the leg actuator unit 110 by reacting on the calf of the user 101. Various embodiments can include but are not limited to the following: suspension forces transmitted through a coupler 150 on the boot (e.g., coupler 150D) or another embodiment of the boot attachment discussed previously; suspension forces transmitted through an electronic and/or fluidic cable assembly; suspension forces transmitted through a connection to a waist belt; suspension forces transmitted through a mechanical connection to a backpack 155 or other housing for the exoskeleton device 510 and/or pneumatic system 520 (see FIG. 5); suspension forces transmitted through straps or a harness to the shoulders of the user 101, and the like.

In various embodiments, a leg actuator unit 110 can be spaced apart from the leg 102 of the user with a limited number of attachments to the leg 102. For example, in some embodiments, the leg actuator unit 110 can consist or consist essentially of three attachments to the leg 102 of the user 101, namely via the first and second attachments 222, 224 and 215. In various embodiments, the couplings of the leg actuator unit 110 to the lower leg portion 105 can consist or consist essentially of a first and second attachment on the anterior and posterior of the lower leg portion 105. In various embodiments, the coupling of the leg actuator unit 110 to the upper leg portion 104 can consist or consist essentially of a single lateral coupling, which can be associated with one or more couplers 150 (e.g., two couplers 150A, 150B as shown in FIGS. 1-4). In various embodiments, such a configuration can be desirable based on the specific force-transfer for use during a subject activity. Accordingly, the number and positions of attachments or coupling to the leg 102 of the user 101 in various embodiments is not a simple design choice and can be specifically selected for one or more selected target user activities.

While specific embodiments of couplers 150 are illustrated herein, in further embodiments, such components discussed herein can be operably replaced by an alternative structure to produce the same functionality. For example, while straps, buckles, padding and the like are shown in various examples, further embodiments can include couplers 150 of various suitable types and with various suitable elements. For example, some embodiments can include Velcro hook-and-loop straps, or the like.

FIGS. 1-3 illustrate an example of an exoskeleton system 100 where the joint 125 is disposed laterally and adjacent to the knee 103 with a rotational axis of the joint 125 being disposed parallel to a rotational axis of the knee 103. In some embodiments, the rotational axis of the joint 125 can be coincident with the rotational axis of the knee 103. In some embodiments, a joint can be disposed on the anterior of the knee 103, posterior of the knee 103, inside of the knee 103, or the like.

In various embodiments, the joint structure 125 can constrain the bellows actuator 130 such that force created by actuator fluid pressure within the bellows actuator 130 can be directed about an instantaneous center (which may or may not be fixed in space). In some cases of a revolute or rotary joint, or a body sliding on a curved surface, this instantaneous center can coincide with the instantaneous center of rotation of the joint 125 or a curved surface. Forces created by a leg actuator unit 110 about a rotary joint 125 can be used to apply a moment about an instantaneous center as well as still be used to apply a directed force. In some cases of a prismatic or linear joint (e.g., a slide on a rail, or the like), the instantaneous center can be kinematically considered to be located at infinity, in which case the force directed about this infinite instantaneous center can be considered as a force directed along the axis of motion of the prismatic joint. In various embodiments, it can be sufficient for a rotary joint 125 to be constructed from a mechanical pivot mechanism. In such an embodiment, the joint 125 can have a fixed center of rotation that can be easy to define, and the bellows actuator 130 can move relative to the joint 125. In a further embodiment, it can be beneficial for the joint 125 to comprise a complex linkage that does not have a single fixed center of rotation. In yet another embodiment, the joint 125 can comprise a flexure design that does not have a fixed joint pivot. In still further embodiments, the joint 125 can comprise a structure, such as a human joint, robotic joint, or the like.

In various embodiments, leg actuator unit 110 (e.g., comprising bellows actuator 130, joint structure 125, and the like) can be integrated into a system to use the generated directed force of the leg actuator unit 110 to accomplish various tasks. In some examples, a leg actuator unit 110 can have one or more unique benefits when the leg actuator unit 110 is configured to assist the human body or is included into a powered exoskeleton system 100. In an example embodiment, the leg actuator unit 110 can be configured to assist the motion of a human user about the user's knee joint 103. To do so, in some examples, the instantaneous center of the leg actuator unit 110 can be designed to coincide or nearly coincide with the instantaneous center of rotation of the knee 103 of a user 101. In one example configuration, the leg actuator unit 110 can be positioned lateral to the knee joint 103 as shown in FIGS. 1-3. In various examples, the human knee joint 103 can function as (e.g., in addition to or in place of) the joint 125 of the leg actuator unit 110.

For clarity, example embodiments discussed herein should not be viewed as a limitation of the potential applications of the leg actuator unit 110 described within this disclosure. The leg actuator unit 110 can be used on other joints of the body including but not limited to one or more elbow, one or more hip, one or more finger, one or more ankle, spine, or neck. In some embodiments, the leg actuator unit 110 can be used in applications that are not on the human body such as in robotics, for general purpose actuation, animal exoskeletons, or the like.

Also, embodiments can be used for or adapted for various suitable applications such as tactical, medical, or labor applications, and the like. Examples of such applications can be found in U.S. patent application Ser. No. 15/823,523, filed Nov. 27, 2017, entitled "PNEUMATIC EXOMUSCLE SYSTEM AND METHOD," and U.S. patent application Ser. No. 15/953,296, filed Apr. 13, 2018, entitled "LEG EXOSKELETON SYSTEM AND METHOD", which are incorporated herein by reference.

Some embodiments can apply a configuration of a leg actuator unit 110 as described herein for linear actuation applications. In an example embodiment, the bellows actuator 130 can comprise a two-layer impermeable/inextensible construction, and one end of one or more constraining ribs can be fixed to the bellows actuator 130 at predetermined positions. The joint structure 125 in various embodiments can be configured as a series of slides on a pair of linear guide rails, where the remaining end of one or more constraining ribs is connected to a slide. The motion and force of the fluidic actuator can therefore be constrained and directed along the linear rail.

Figure 5:
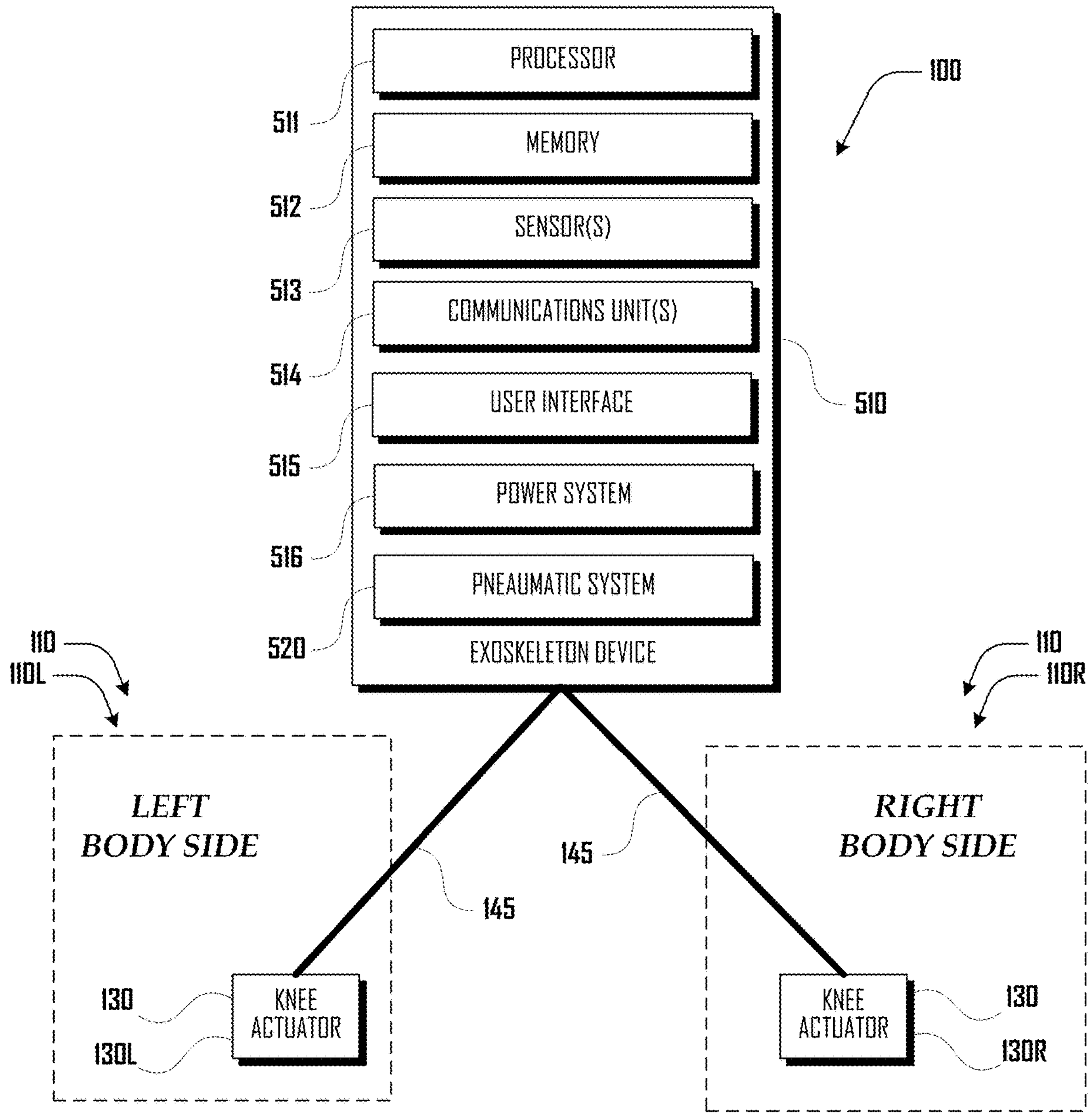
FIG. 5 is a block diagram illustrating an example embodiment of an exoskeleton system.

FIG. 5 is a block diagram of an example embodiment of an exoskeleton system 100 that includes an exoskeleton device 510. While a pneumatic system 520 is used in the example of FIG. 5, further embodiments can include any suitable fluidic system or a pneumatic system 520 can be absent in some embodiments, such as where an exoskeleton system 100 is actuated by electric motors, or the like.

The exoskeleton device 510 in this example comprises a processor 511, a memory 512, one or more sensors 513 a communication unit 514, a user interface 515, a power source 516 and a pneumatic system 520. In various embodiments, fluid (e.g., air), electrical power, communication signals, and the like can be communicated to and/or from the actuator units 110 via respective cables 145. For example, the cables 145 can be configured to convey air from a fluid source (e.g., of the pneumatic system 520) to the actuators 130, which can cause actuation of the actuators 130 as discussed herein. In various embodiments, the cables 145 can be configured to provide air to the actuators 130 separately such that the actuators 130 can be selectively controlled separately.

Additionally, in various embodiments, the lines can be configured to transmit electrical power from the power system 516 (e.g., from a battery) to the actuator units 110, which can be used at the actuator units 110 to power elements of the actuator units 110 such as pneumatic valves, sensors, an embedded system, an interface, a computing system, and the like. In various embodiments, the actuator units 110 and exoskeleton device 510 can be configured to communicate via the cables 145. For example, in various embodiments, the exoskeleton device 510 can communicate control signals (e.g., via the communication unit(s) 514) to the actuator units 110, which can be configured to control actuation of the actuator units 110, output of an interface, or the like. In further embodiments, any suitable communications or data can be sent to the actuator units 110 and/or actuators 130 via the cables 145, which can be via any suitable communication protocol. Also, in various embodiments, communications or data can be sent to the exoskeleton device 510 from the actuator units 110 and/or actuators 130 via the cables 145. For example, sensor data, status data, configuration data, pneumatic data, or the like, can be sent to the exoskeleton device 510 from the actuator units 110 and/or actuators 130 via the cables 145.

In accordance with some embodiments, communication to or from or between the exoskeleton device 510 and the actuator units 110 and/or actuators 130 can comprise wireless communication in addition to or alternative to communication via the cables 145. However, in some embodiments, communications to or from or between the exoskeleton device 510 and the actuator units 110 and/or actuators 130 can be exclusively via the cables 145, with the system being incapable of wireless communications to or from or between the exoskeleton device 510 and the actuator units 110 and/or actuators 130.

Also, as discussed in more detail herein, in various embodiments, the cables 145 can be configured as a unitary structure capable of transmitting electrical power, fluid (e.g., air), and/or communications to, from or between the exoskeleton device 510 and the actuator units 110 and/or actuators 130. In other words, various embodiments can have, consist of or consist essentially of only a single unitary cable 145 for transmitting electrical power, fluid (e.g., air), and/or communications to, from or between the exoskeleton device 510 and respective actuator units 110 and/or respective actuators 130 via one or more electrical power lines (e.g., wires), one or more fluid lines (e.g., tubes), one or more communication lines (e.g., wires, fiberoptic, etc.), and the like.

It can be desirable in some examples for the cable(s) 145 to be strong to hold up against unintentional strain. In a preferred embodiment one or more electrical power lines, one or more fluid lines, and/or one or more communication lines are unified into one cable 145. In such an embodiment the one or more electrical power lines, one or more fluid lines, and/or one or more communication lines can run in parallel and can be encased in a sheath individually and/or collectively (e.g., with a medical grade material). For example, encasing such lines to define a cable 145 can include various insulation, inner/outer sheaths, and the like. Encasing the one or more electrical power lines, one or more fluid lines, and/or one or more communication lines together with a strong material in some embodiments can help protect them from environmental factors, such as water, snow, or sand. In another embodiment, the one or more electrical power lines, one or more fluid lines, and/or one or more communication lines may run in parallel together and are attached together in various suitable ways (e.g., by zip ties, tape or adhesives). Whether the one or more electrical power lines, one or more fluid lines, and/or one or more communication lines are one component or more, by attaching them together in various embodiments, weaker electronic wires may no longer need to hold the high strain that stronger fluidic tubes can withstand.

It can also be desirable to reduce the length of cables 145 hanging outside of the pack, which can snag onto other objects. One preferred set of embodiments includes retractable cables 145. In at least some of such embodiments, it can be preferable for the retractable cables 145 to be accomplished inside a backpack 155 where the cables are configured to have a small mechanical retention force to maintain cables 145 that are pulled tight against the user with reduced slack remaining in the cable(s) 145. This can be done in some embodiments with a linear spring attached to the cables or a rotating spool with a rotational spring, both of which may pull the cable back into the power pack (e.g., backpack 155) in various examples. Further embodiments can be used to organize or route the cables 145 so that they do not snag, such as integrating them into the user's clothing, or clipping onto other sections of the power pack with hooks, straps, buttons or magnets.

Another aspect of the cable(s) 145 can be mounting to the backpack 155, actuator unit 110 and/or actuator 130. In a preferred embodiment, pigtail type connections are used. In various pigtail type connections, the cable 145 extends through a rigid housing of a given device and a portion of the cable connector 600 is at the end of the cable 145. Specifically, these connections in some examples can utilize inline connections as opposed to panel-mount connections. This can reduce the shear stress on the internal electronics and mechanical connection, if, for example a cable 145 is accidentally snagged by an object. Various other types of line mounts can be used including, but not limited to, panel-mounted connections.

The plurality of actuators 130 include a pair of knee-actuators 130L and 130R that are positioned on the right and left side of a body 100. For example, as discussed above, the example exoskeleton system 100 shown in FIG. 5 can comprise a left and right leg actuator unit 110L, 110R on respective sides of the body 101 as shown in FIGS. 1 and 2 with one or both of the exoskeleton device 510 and pneumatic system 520, or one or more components thereof, stored within or about a backpack 155 (see FIG. 1) or otherwise mounted, worn or held by a user 101.

Accordingly, in various embodiments, the exoskeleton system 100 can be a completely mobile and self-contained system that is configured to be powered and operated for an extended period of time without an external power source during various user activities. The size, weight and configuration of the actuator unit(s) 110, exoskeleton device 510 and pneumatic system 520 can therefore be configured in various embodiments for such mobile and self-contained operation.

In various embodiments, the example system 100 can be configured to move and/or enhance movement of the user 101 wearing the exoskeleton system 100. For example, the exoskeleton device 510 can provide instructions to the pneumatic system 520, actuator units 110 and/or actuators 130, which can selectively inflate and/or deflate the bellows actuators 130 via the cables 145. For example, fluid can be sent to the actuator units 110 and/or actuators 130 via the cables 145 with control of such fluid being via fluid valves or other suitable elements at the exoskeleton device 510, actuator units 110 and/or actuators 130. Such selective inflation and/or deflation of the bellows actuators 130 can move and/or support one or both legs 102 to generate and/or augment body motions such as walking, running, jumping, climbing, lifting, throwing, squatting, skiing or the like.

In some cases, the exoskeleton system 100 can be designed to support multiple configurations in a modular configuration. For example, one embodiment is a modular configuration that is designed to operate in either a single knee configuration or in a double knee configuration as a function of how many of the actuator units 110 are donned by the user 101. For example, the exoskeleton device 510 can determine how many actuator units 110 are coupled to the pneumatic system 520 and/or exoskeleton device 510 (e.g., one or two actuator units 110) and the exoskeleton device 510 can change operating capabilities based on the number of actuator units 110 detected.

In further embodiments, the pneumatic system 520 can be manually controlled, configured to apply a constant pressure, or operated in any other suitable manner. In some embodiments, such movements can be controlled and/or programmed by the user 101 that is wearing the exoskeleton system 100 or by another person. In some embodiments, the exoskeleton system 100 can be controlled by movement of the user 101. For example, the exoskeleton device 510 can sense that the user is walking and carrying a load and can provide a powered assist to the user via the actuators 130 to reduce the exertion associated with the load and walking. Similarly, where a user 101 wears the exoskeleton system 100, the exoskeleton system 100 can sense movements of the user 101 and can provide a powered assist to the user via the actuators 130 to enhance or provide an assist to the user while skiing.

Accordingly, in various embodiments, the exoskeleton system 130 can react automatically without direct user interaction. In further embodiments, movements can be controlled in real-time by user interface 515 such as a controller, joystick, voice control or thought control. Additionally, some movements can be pre-preprogrammed and selectively triggered (e.g., walk forward, sit, crouch) instead of being completely controlled. In some embodiments, movements can be controlled by generalized instructions (e.g., walk from point A to point B, pick up box from shelf A and move to shelf B).

The user interface 515 can allow the user 101 to control various aspects of the exoskeleton system 100 including powering the exoskeleton system 100 on and off; controlling movements of the exoskeleton system 100; configuring settings of the exoskeleton system 100, and the like. The user interface 515 can include various suitable input elements such as a touch screen, one or more buttons, audio input, and the like. The user interface 515 can be located in various suitable locations about the exoskeleton system 100. For example, in one embodiment, the user interface 515 can be disposed on a strap of a backpack 155, or the like. In some embodiments, the user interface can be defined by a user device such as smartphone, smart-watch, wearable device, or the like.

In various embodiments, the power source 516 can be a mobile power source that provides the operational power for the exoskeleton system 100. In one preferred embodiment, the power pack unit contains some or all of the pneumatic system 520 (e.g., a compressor) and/or power source (e.g., batteries) required for the continued operation of pneumatic actuation of the leg actuator units 110. The contents of such a power pack unit can be correlated to the specific actuation approach configured to be used in the specific embodiment. In some embodiments, the power pack unit will only contain batteries which can be the case in an electromechanically actuated system or a system where the pneumatic system 520 and power source 516 are separate. Various embodiments of a power pack unit can include but are not limited to a combination of one or more of the following items: pneumatic compressor, batteries, stored high-pressure pneumatic chamber, hydraulic pump, pneumatic safety components, electric motor, electric motor drivers, microprocessor, and the like. Accordingly, various embodiments of a power pack unit can include one or more of elements of the exoskeleton device 510 and/or pneumatic system 520.

Such components can be configured on the body of a user 101 in a variety of suitable ways. One preferred embodiment is the inclusion of a power pack unit in a torso-worn pack that is not operably coupled to the leg actuator units 110 in any manner that transmits substantial mechanical forces to the leg actuator units 110. Another embodiment includes the integration of the power pack unit, or components thereof, into the leg actuator units 110 themselves. Various embodiments can include but are not limited to the following configurations: torso-mounted in a backpack, torso-mounted in a messenger bag, hip-mounted bag, mounted to the leg, integrated into the brace component, and the like. Further embodiments can separate the components of the power pack unit and disperse them into various configurations on the user 101. Such an embodiment may configure a pneumatic compressor on the torso of the user 101 and then integrate the batteries into the leg actuator units 110 of the exoskeleton system 100.

One aspect of the power supply 516 in various embodiments is that it must be connected to the brace component in such a manner as to pass the operable system power to the brace for operation. One preferred embodiment is the use of electrical cables (e.g., as part of unified cable 145) to connect the power supply 516 and the leg actuator units 110. Other embodiments can use electrical cables separate from cables 145, wireless power transmission, and/or local batteries to deliver electrical power. Various embodiments can include but are not limited to any configuration of the following connections, which may or may not be part of a unified cable 145: pneumatic hosing, hydraulic hosing, electrical cables, wireless communication, wireless power transfer, and the like.

In some embodiments, it can be desirable to include secondary features that extend the capabilities of a cable connection (e.g., cables 145) between the leg actuator units 110 and elements of the exoskeleton device 510 such as the power supply 516 and/or pneumatic system 520. One preferred embodiment includes retractable cables that are configured to have a small mechanical retention force to maintain cables 145 that are pulled tight against the user with reduced slack remaining in the cables 145. Various embodiments can include but are not limited to a combination of the following secondary features: retractable cables, a single cable 145 including both fluidic and electrical power, magnetically connected electrical cables, mechanical quick releases, breakaway connections designed to release at a specified pull force, integration into mechanical retention features on the user's clothing, a unified singular cable 145 for power, air and/or communications, and the like. Yet another embodiment can include routing the cables 145 in such a way as to minimize geometric differences between the user 101 and lengths of the cables 145. One such embodiment in a dual knee configuration with a torso power supply can be routing the cables 145 along the user's lower torso to connect the right side of a power supply bag with the left knee of the user. Such a routing can allow the geometric differences in length throughout the user's normal range of motion.

One specific additional feature that can be a concern in some embodiments is the need for proper heat management of the exoskeleton system 100. As a result, there are a variety of features that can be integrated specifically for the benefit of controlling heat. One preferred embodiment integrates exposed heat sinks to the environment that allow elements of the exoskeleton device 510 and/or pneumatic system 520 to dispel heat directly to the environment through unforced cooling using ambient airflow. Another embodiment directs the ambient air through internal air channels in a backpack 155 or other housing to allow for internal cooling. Yet another embodiment can extend upon this capability by introducing scoops on a backpack 155 or other housing in an effort to allow air flow through the internal channels. Various embodiments can include but are not limited to the following: exposed heat sinks that are directly connected to a high heat component; a water-cooled or fluid-cooled heat management system; forced air cooling through the introduction of a powered fan or blower; external shielded heat sinks to protect them from direct contact by a user, and the like.

In some cases, it may be beneficial to integrate additional features into the structure of the backpack 155 or other housing to provide additional features to the exoskeleton system 100. One preferred embodiment is the integration of mechanical attachments to support storage of the leg actuator units 110 along with the exoskeleton device 510 and/or pneumatic system 520 in a small package. Such an embodiment can include a deployable pouch that can secure the leg actuator units 110 against the backpack 155 along with mechanical clasps that hold the upper or lower arms 115, 120 of the actuator units 110 to the backpack 155. Another embodiment is the inclusion of storage capacity into the backpack 155 so the user 101 can hold additional items such as a water bottle, food, personal electronics, and other personal items. Various embodiments can include but are not limited to other additional features such as the following: a warming pocket which is heated by hot airflow from the exoskeleton device 510 and/or pneumatic system 520; air scoops to encourage additional airflow internal to the backpack 155; strapping to provide a closer fit of the backpack 155 on the user, waterproof storage, temperature-regulated storage, and the like.

In a modular configuration, it may be required in some embodiments that the exoskeleton device 510 and/or pneumatic system 520 can be configured to support the electrical power, fluidic power, sensing and control requirements and capabilities of various potential configurations of the exoskeleton system. One preferred embodiment can include an exoskeleton device 510 and/or pneumatic system 520 that can be tasked with powering a dual knee configuration or a single knee configuration (i.e., with one or two leg actuator units 110 on the user 101). Such an exoskeleton system 100 can support the requirements of both configurations and then appropriately configure electrical power, fluidic power, sensing and control based on a determination or indication of a desired operating configuration. Various embodiments exist to support an array of potential modular system configurations, such as multiple batteries, and the like.

In various embodiments, the exoskeleton device 100 can be operable to perform methods or portions of methods described in more detail below or in related applications incorporated herein by reference. For example, the memory 512 can include non-transitory computer readable instructions (e.g., software), which if executed by the processor 511, can cause the exoskeleton system 100 to perform methods or portions of methods described herein or in related applications incorporated herein by reference.

This software can embody various methods that interpret signals from the sensors 513 or other sources to determine how to best operate the exoskeleton system 100 to provide the desired benefit to the user. The specific embodiments described below should not be used to imply a limit on the sensors 513 that can be applied to such an exoskeleton system 100 or the source of sensor data. While some example embodiments can require specific information to guide decisions, it does not create an explicit set of sensors 513 that an exoskeleton system 100 will require, and further embodiments can include various suitable sets of sensors 513. Additionally, sensors 513 can be located at various suitable locations on an exoskeleton system 100 including as part of an exoskeleton device 510, pneumatic system 520, one or more fluidic actuator 130, or the like. Accordingly, the example illustration of FIG. 5 should not be construed to imply that sensors 513 are exclusively disposed at or part of an exoskeleton device 510, and such an illustration is merely provided for purposes of simplicity and clarity.

One aspect of control software can be the operational control of leg actuator units 110, exoskeleton device 510 and pneumatic system 520 to provide the desired response. There can be various suitable responsibilities of the operational control software. For example, as discussed in more detail below, one can be low-level control which can be responsible for developing baseline feedback for operation of the leg actuator units 110, exoskeleton device 510 and pneumatic system 520. Another can be intent recognition which can be responsible for identifying the intended maneuvers of the user 101 based on data from the sensors 513 and causing the exoskeleton system 100 to operate based on one or more identified intended maneuvers. A further example can include reference generation, which can include selecting the desired torques the exoskeleton system 100 should generate to best assist the user 101. It should be noted that this example architecture for delineating the responsibilities of the operational control software is merely for descriptive purposes and in no way limits the wide variety of software approaches that can be deployed on further embodiments of an exoskeleton system 100.

One method implemented by control software can be for the low-level control and communication of the exoskeleton system 100. This can be accomplished via a variety of methods as required by the specific joint and need of the user. In a preferred embodiment, the operational control is configured to provide a desired torque by the leg actuator unit 110 at the user's joint. In such a case, the exoskeleton system 100 can create low-level feedback to achieve a desired joint torque by the leg actuator units 110 as a function of feedback from the sensors 513 of the exoskeleton system 100. For example, such a method can include obtaining sensor data from one or more sensors 513, determining whether a change in torque by the leg actuator unit 110 is necessary, and if so, causing the pneumatic system 520 to change the fluid state of the leg actuator unit 110 to achieve a target joint torque by the leg actuator unit 110. Various embodiments can include, but are not limited to, the following: current feedback; recorded behavior playback; position-based feedback; velocity-based feedback; feedforward responses; volume feedback which controls a fluidic system 520 to inject a desired volume of fluid into an actuator 130, and the like.

Another method implemented by operational control software can be for intent recognition of the user's intended behaviors. This portion of the operational control software, in some embodiments, can indicate any array of allowable behaviors that the system 100 is configured to account for. In one preferred embodiment, the operational control software is configured to identify two specific states: Walking, and Not Walking. In such an embodiment, to complete intent recognition, the exoskeleton system 100 can use user input and/or sensor readings to identify when it is safe, desirable or appropriate to provide assistive actions for walking. For example, in some embodiments, intent recognition can be based on input received via the user interface 515, which can include an input for Walking, and Not Walking. Accordingly, in some examples, the use interface can be configured for a binary input consisting of Walking, and Not Walking.

In some embodiments, a method of intent recognition can include the exoskeleton device 510 obtaining data from the sensors 513 and determining, based at least in part of the obtained data, whether the data corresponds to a user state of Walking, and Not Walking. Where a change in state has been identified, the exoskeleton system 100 can be re-configured to operate in the current state. For example, the exoskeleton device 510 can determine that the user 101 is in a Not Walking state such as sitting and can configure the exoskeleton system 100 to operate in a Not Walking configuration. For example, such a Not Walking configuration can, compared to a Walking configuration, provide for a wider range of motion; provide no torque or minimal torque to the leg actuation units 110; save power and fluid by minimizing processing and fluidic operations; cause the system to be alert for supporting a wider variety of non-skiing motion, and the like.

The exoskeleton device 510 can monitor the activity of the user 101 and can determine that the user is walking or is about to walk (e.g., based on sensor data and/or user input), and can then configure the exoskeleton system 100 to operate in a Walking configuration. For example, such a Walking configuration, compared to a Not Walking configuration, can allow for a more limited range of motion that would be present during skiing (as opposed to motions during non-walking); provide for high or maximum performance by increasing the processing and fluidic response of the exoskeleton system 100 to support skiing; and the like. When the user 101 finishes a walking session, is identified as resting, or the like, the exoskeleton system 100 can determine that the user is no longer walking (e.g., based on sensor data and/or user input) and can then configure the exoskeleton system 100 to operate in the Not Walking configuration.

In some embodiments, there can be a plurality of Walking states, or Walking sub-states that can be determined by the exoskeleton system 100, including hard walking, moderate walking, light walking, downhill, uphill, jumping, recreational, sport, running, and the like (e.g., based on sensor data and/or user input). Such states can be based on the difficulty of the walking, ability of the user, terrain, weather conditions, elevation, angle of the walking surface, desired performance level, power-saving, and the like. Accordingly, in various embodiments, the exoskeleton system 100 can adapt for various specific types of walking or movement based on a wide variety of factors.

Another method implemented by operational control software can be the development of desired referenced behaviors for the specific joints providing assistance. This portion of the control software can tie together identified maneuvers with the level control. For example, when the exoskeleton system 100 identifies an intended user maneuver, the software can generate reference behaviors that define the torques, or positions desired by the actuators 130 in the leg actuation units 110. In one embodiment, the operational control software generates references to make the leg actuation units 110 simulate a mechanical spring at the knee 103 via the configuration actuator 130. The operational control software can generate torque references at the knee joints that are a linear function of the knee joint angle. In another embodiment, the operational control software generates a volume reference to provide a constant standard volume of air into a pneumatic actuator 130. This can allow the pneumatic actuator 130 to operate like a mechanical spring by maintaining the constant volume of air in the actuator 130 regardless of the knee angle, which can be identified through feedback from one or more sensors 513.

In another embodiment, a method implemented by the operational control software can include evaluating the balance of the user 101 while walking, moving, standing, or running and directing torque in such a way to encourage the user 101 to remain balanced by directing knee assistance to the leg 102 that is on the outside of the user's current balance profile. Accordingly, a method of operating an exoskeleton system 100 can include the exoskeleton device 510 obtaining sensor data from the sensors 510 indicating a balance profile of a user 101 based on the configuration of left and right leg actuation units 110L, 110R and/or environmental sensors such as position sensors, accelerometers, and the like. The method can further include determining a balance profile based on the obtained data, including an outside and inside leg, and then increasing torque to the actuation unit 110 associated with the leg 102 identified as the outside leg.

Various embodiments can use but are not limited to kinematic estimates of posture, joint kinetic profile estimates, as well as observed estimates of body pose. Various other embodiments exist for methods of coordinating two legs 102 to generate torques including but not limited to guiding torque to the most bent leg; guiding torque based on the mean amount of knee angle across both legs; scaling the torque as a function of speed or acceleration; and the like. Yet another embodiment can include a combination of various individual reference generation methods in a variety of matters which include but are not limited to a linear combination, a maneuver specific combination, or a non-linear combination.

In another embodiment, an operational control method can blend two primary reference generation techniques: one reference focused on static assistance and one reference focused on leading the user 101 into their upcoming behavior. In some examples, the user 101 can select how much predictive assistance is desired while using the exoskeleton system 100. For example, by a user 101 indicating a large amount of predictive assistance, the exoskeleton system 100 can be configured to be very responsive and may be well configured for a skilled operator on a challenging terrain. The user 101 could also indicate a desire for a very low amount of predictive assistance, which can result in slower system performance, which may be better tailored towards a learning user or less challenging terrain.

Various embodiments can incorporate user intent in a variety of manners and the example embodiments presented above should not be interpreted as limiting in any way. For example, method of determining and operating an exoskeleton system 100 can include systems and method of U.S.

patent application Ser. No. 15/887,866, filed Feb. 2, 2018, entitled "SYSTEM AND METHOD FOR USER INTENT RECOGNITION,", which is incorporated herein by reference. Also, various embodiments can use user intent in a variety of manners including as a continuous unit, or as a discrete setting with only a few indicated values.

At times it can be beneficial for operational control software to manipulate its control to account for a secondary or additional objective in order to maximize device performance or user experience. In one embodiment, the exoskeleton system 100 can provide an elevation-aware control over a central compressor or other components of a pneumatic system 520 to account for the changing density of air at different elevations. For example, operational control software can identify that the system is operating at a higher elevation based on data from sensors 513, or the like, and provide more current to the compressor in order to maintain electrical power consumed by the compressor. Accordingly, a method of operating a pneumatic exoskeleton system 100 can include obtaining data indicating air density where the pneumatic exoskeleton system 100 is operating (e.g., elevation data), determining optimal operating parameters of the pneumatic system 520 based on the obtained data, and configuring operation based on the determined optimal operating parameters. In further embodiments, operation of a pneumatic exoskeleton system 100 such as operating volumes can be tuned based on environmental temperature, which may affect air volumes.

In another embodiment, the exoskeleton system 100 can monitor the ambient audible noise levels and vary the control behavior of the exoskeleton system 100 to reduce the noise profile of the system. For example, when a user 101 is in a quiet public place or quietly enjoying a location alone or with others, noise associated with actuation of the leg actuation units 110 can be undesirable (e.g., noise of running a compressor or inflating or deflating actuators 130). Accordingly, in some embodiments, the sensors 513 can include a microphone that detects ambient noise levels and can configure the exoskeleton system 100 to operate in a quiet mode when ambient noise volume is below a certain threshold. Such a quiet mode can configure elements of a pneumatic system 520 or actuators 130 to operate more quietly, or can delay or reduce frequency of noise made by such elements.

In the case of a modular system, it can be desirable in various embodiments for operational control software to operate differently based on the number of leg actuation units 110 operational within the exoskeleton system 100. For example, in some embodiments, a modular dual-knee exoskeleton system 100 (see e.g., FIGS. 1 and 2) can also operate in a single-knee configuration where only one of two leg actuation units 110 are being worn by a user 101 (see e.g., FIGS. 3 and 4) and the exoskeleton system 100 can generate references differently when in a two-leg configuration compared to a single-leg configuration. Such an embodiment can use a coordinated control approach to generate references where the exoskeleton system 100 is using inputs from both leg actuation units 110 to determine the desired operation. However, in a single-leg configuration, the available sensor information may have changed, so in various embodiments the exoskeleton system 100 can implement a different control method. In various embodiments this can be done to maximize the performance of the exoskeleton system 100 for the given configuration or account for differences in available sensor information based on there being one or two leg actuation units 110 operating in the exoskeleton system 100.

Accordingly, a method of operating an exoskeleton system 100 can include a startup sequence where a determination is made by the exoskeleton device 510 whether one or two leg actuation units 110 are operating in the exoskeleton system 100; determining a control method based on the number of actuation units 110 that are operating in the exoskeleton system 100; and implementing and operating the exoskeleton system 100 with the selected control method. A further method operating an exoskeleton system 100 can include monitoring by the exoskeleton device 510 of actuation units 110 that are operating in the exoskeleton system 100, determining a change in the number of actuation units 110 operating in the exoskeleton system 100, and then determining and changing the control method based on the new number of actuation units 110 that are operating in the exoskeleton system 100.

For example, the exoskeleton system 100 can be operating with two actuation units 110 and with a first control method. The user 101 can disengage one of the actuation units 110, and the exoskeleton device 510 can identify the loss of one of the actuation units 110, and the exoskeleton device 510 can determine and implement a new second control method to accommodate loss of one of the actuation units 110. In some examples, adapting to the number of active actuation units 110 can be beneficial where one of the actuation units 110 is damaged or disconnected during use and the exoskeleton system 100 is able to adapt automatically so the user 101 can still continue working or moving uninterrupted despite the exoskeleton system 100 only having a single active actuation unit 110.

In various embodiments, operational control software can adapt a control method where user needs are different between individual actuation units 110 or legs 102. In such an embodiment, it can be beneficial for the exoskeleton system 100 to change the torque references generated in each actuation unit 110 to tailor the experience for the user 101. One example is of a dual knee exoskeleton system 100 (see e.g., FIG. 1) where a user 101 has significant weakness issues in a single leg 102, but only minor weakness issues in the other leg 102. In this example, the exoskeleton system 100 can be configured to scale down the output torques on the less-affected limb compared to the more-affected limb to best meet the needs of the user 101.

Such a configuration based on differential limb strength can be done automatically by the exoskeleton system 100 and/or can be configured via a user interface 516, or the like. For example, in some embodiments, the user 101 can perform a calibration test while using the exoskeleton system 100, which can test relative strength or weakness in the legs 102 of the user 101 and configure the exoskeleton system 100 based on identified strength or weakness in the legs 102. Such a test can identify general strength or weakness of legs 102 or can identify strength or weakness of specific muscles or muscle groups such as the quadriceps, calves, hamstrings, gluteus, gastrocnemius; femoris, sartorius, soleus, and the like.

Another aspect of a method for operating an exoskeleton system 100 can include control software that monitors the exoskeleton system 100. A monitoring aspect of such software can, in some examples, focus on monitoring the state of the exoskeleton system 100 and the user 101 throughout normal operation in an effort to provide the exoskeleton system 100 with situational awareness and understanding of sensor information in order to drive user understanding and device performance. One aspect of such monitoring software can be to monitor the state of the exoskeleton system 100 in order to provide device understanding to achieve a desired performance capability. A portion of this can be the development of a system body pose estimate. In one embodiment, the exoskeleton device 510 uses the onboard sensors 513 to develop a real-time understanding of the user's pose. In other words, data from sensors 513 can be used to determine the configuration of the actuation units 110, which along with other sensor data can in turn be used to infer a user pose or body configuration estimate of the user 101 wearing the actuation units 110.

At times, and in some embodiments, it can be unrealistic or impossible for the exoskeleton system 100 to directly sense all important aspects of the system pose due to the sensing modalities not existing or their inability to be practically integrated into the hardware. As a result, the exoskeleton system 100 in some examples can rely on a fused understanding of the sensor information around an underlying model of the user's body and the exoskeleton system 100 the user is wearing. In one embodiment of a dual leg knee assistance exoskeleton system 100, the exoskeleton device 510 can use an underlying model of the user's lower extremity and torso body segments to enforce a relational constraint between the otherwise disconnected sensors 513. Such a model can allow the exoskeleton system 100 to understand the constrained motion of the two legs 102 in that they are mechanically connected through the user's kinematic chain created by the body. This approach can be used to ensure that the estimates for knee orientation are properly constrained and biomechanically valid. In various embodiments, the exoskeleton system 100 can include sensors 513 embedded in the exoskeleton device 510 and/or pneumatic system 520 to provide a fuller picture of the system posture. In yet another embodiment, the exoskeleton system 100 can include logical constraints that are unique to the application in an effort to provide additional constraints on the operation of the pose estimation. This can be desirable, in some embodiments, in conditions where ground truth information is unavailable such as highly dynamic actions, where the exoskeleton system 100 is denied an external GPS signal, or the earth's magnetic field is distorted.

In some embodiments, changes in configuration of the exoskeleton system 100 based on location and/or location attributes can be performed automatically and/or with input from the user 101. For example, in some embodiments, the exoskeleton system 100 can provide one or more suggestions for a change in configuration based on location and/or location attributes and the user 101 can choose to accept such suggestions. In further embodiments, some or all configurations of the exoskeleton system 100 based on location and/or location attributes can occur automatically without user interaction.

Various embodiments can include the collection and storage of data from the exoskeleton system 100 throughout operation. In one embodiment, this can include the live streaming of the data collected on the exoskeleton device 510 to a cloud storage location via the communication unit(s) 514 through an available wireless communication protocol or storage of such data on the memory 512 of the exoskeleton device 510, which may then be uploaded to another location via the communication unit(s) 514. For example, when the exoskeleton system 100 obtains a network connection, recorded data can be uploaded to the cloud at a communication rate that is supported by the available data connection. Various embodiments can include variations of this, but the use of monitoring software to collect and store data about the exoskeleton system 100 locally and/or remotely for retrieval at a later time for an exoskeleton system 100 such as this can be included in various embodiments.

In some embodiments, once such data has been recorded, it can be desirable to use the data for a variety of different applications. One such application can be the use of the data to develop further oversight functions on the exoskeleton system 100 in an effort to identify device system issues that are of note. One embodiment can be the use of the data to identify a specific exoskeleton system 100 or leg actuator unit 110 among a plurality, whose performance has varied significantly over a variety of uses. Another use of the data can be to provide it back to the user 101 to gain a better understanding of how they ski. One embodiment of this can be providing the data back to the user 101 through a mobile application that can allow the user 101 to review their use on a mobile device. Yet another use of such device data can be to synchronize playback of data with an external data stream to provide additional context. One embodiment is a system that incorporates the GPS data from a companion smartphone with the data stored natively on the device. Another embodiment can include the time synchronization of recorded video with the data stored that was obtained from the device 100. Various embodiments can use these methods for immediate use of data by the user to evaluate their own performance, for later retrieval by the user to understand behavior from the past, for users to compare with other users in-person or through an online profile, by developers to further the development of the system, and the like.

Another aspect of a method of operating an exoskeleton system 100 can include monitoring software configured for identifying user-specific traits. For example, the exoskeleton system 100 can provide an awareness of how a specific skier 101 operates in the exoskeleton system 100 and over time can develop a profile of the user's specific traits in an effort to maximize device performance for that user. One embodiment can include the exoskeleton system 100 identifying a user-specific use type in an effort to identify the use style or skill level of the specific user. Through an evaluation of the user form and stability during various actions (e.g., via analysis of data obtained from the sensors 513 or the like), the exoskeleton device 510 in some examples can identify if the user is highly skilled, novice, or beginner. This understanding of skill level or style can allow the exoskeleton system 100 to better tailor control references to the specific user.

In further embodiments, the exoskeleton system 100 can also use individualized information about a given user to build a profile of the user's biomechanic response to the exoskeleton system 100. One embodiment can include the exoskeleton system 100 collecting data regarding the user to develop an estimate of the individual user's knee strain in an effort to assist the user with understanding the burden the user has placed on his legs 102 throughout use. This can allow the exoskeleton system 100 to alert a user if the user has reached a historically significant amount of knee strain to alert the user that he may want to stop to spare himself potential pain or discomfort.

Another embodiment of individualized biomechanic response can be the system collecting data regarding the user to develop an individualized system model for the specific user. In such an embodiment the individualized model can be developed through a system ID (identification) method that evaluates the system performance with an underlying system model and can identify the best model parameters to fit the specific user. The system ID in such an embodiment can operate to estimate segment lengths and masses (e.g., of legs 102 or portions of the legs 102) to better define a dynamic user model. In another embodiment, these individualized model parameters can be used to deliver user specific control responses as a function of the user's specific masses and segment lengths. In some examples of a dynamic model, this can help significantly with the device's ability to account for dynamic forces during highly challenging activities.

In various embodiments, the exoskeleton system 100 can provide for various types of user interaction. For example, such interaction can include input from the user 101 as needed into the exoskeleton system 100 and the exoskeleton system 100 providing feedback to the user 101 to indicate changes in operation of the exoskeleton system 100, status of the exoskeleton system 100, and the like. As discussed herein, user input and/or output to the user can be provided via one or more user interface 515 of the exoskeleton device 510 or can include various other interfaces or devices such as a smartphone user device. Such one or more user interfaces 515 or devices can be located in various suitable locations such as on a backpack 155 (see e.g., FIG. 1), the pneumatic system 520, leg actuation units 110, or the like.

The exoskeleton system 100 can be configured to obtain intent from the user 101. For example, this can be accomplished through a variety of input devices that are either integrated directly with the other components of the exoskeleton system 100 (e.g., one or more user interface 515), or external and operably connected with the exoskeleton system 100 (e.g., a smartphone, wearable device, remote server, or the like). In one embodiment, a user interface 515 can comprise a button that is integrated directly into one or both of the leg actuation units 110 of the exoskeleton system 100. This single button can allow the user 101 to indicate a variety of inputs. In another embodiment, a user interface 515 can be configured to be provided through a torso-mounted lapel input device that is integrated with the exoskeleton device 510 and/or pneumatic system 520 of the exoskeleton system 100. In one example, such a user interface 515 can comprise a button that has a dedicated enable and disable functionality; a selection indicator dedicated to the user's desired power level (e.g., an amount or range of force applied by the leg actuator units 110); and a selector switch that can be dedicated to the amount of predictive intent to integrate into the control of the exoskeleton system 100. Such an embodiment of a user interface 515 can use a series of functionally locked buttons to provide the user 101 with a set of understood indicators that may be required for normal operation in some examples. Yet another embodiment can include a mobile device that is connected to the exoskeleton system 100 via a Bluetooth connection or other suitable wired or wireless connection. Use of a mobile device or smartphone as a user interface 515 can allow the user a far greater amount of input to the device due to the flexibility of the input method. Various embodiments can use the options listed above or combinations and variants thereof but are in no way limited to the explicitly stated combinations of input methods and items.

The one or more user interface 515 can provide information to the user 101 to allow the user to appropriately use and operate the exoskeleton system 100. Such feedback can be in a variety of visual, haptic and/or audio methods including, but not limited to, feedback mechanisms integrated directly on one or both of the actuation units 110; feedback through operation of the actuation units 110; feedback through external items not integrated with the exoskeleton system 100 (e.g., a mobile device); and the like. Some embodiments can include integration of feedback lights in the actuation units 110 of the exoskeleton system 100. In one such embodiment, five multi-color lights are integrated into the knee joint 125 or other suitable location such that the user 101 can see the lights. These lights can be used to provide feedback of system errors, device power, successful operation of the device, and the like. In another embodiment, the exoskeleton system 100 can provide controlled feedback to the user to indicate specific pieces of information. In such embodiments, the exoskeleton system 100 can pulse the joint torque on one or both of the leg actuation units 110 to the maximum allowed torque when the user changes the maximum allowable user-desired torque, which can provide a haptic indicator of the torque settings. Another embodiment can use an external device such as a mobile device where the exoskeleton system 100 can provide alert notifications for device information such as operational errors, setting status, power status, and the like. Types of feedback can include, but are not limited to, lights, sounds, vibrations, notifications, and operational forces integrated in a variety of locations that the user 101 may be expected to interact with including the actuation units 110, pneumatic system 520, backpack 155, mobile devices, or other suitable methods of interactions such as a web interface, SMS text or email.

The communication unit 514 can include hardware and/or software that allows the exoskeleton system 100 to communicate with other devices, including a user device, a classification server, other exoskeleton systems 100, or the like, directly or via a network. For example, the exoskeleton system 100 can be configured to connect with a user device, which can be used to control the exoskeleton system 100, receive performance data from the exoskeleton system 100, facilitate updates to the exoskeleton system, and the like. Such communication can be wired and/or wireless communication.

In some embodiments, the sensors 513 can include any suitable type of sensor, and the sensors 513 can be located at a central location or can be distributed about the exoskeleton system 100. For example, in some embodiments, the exoskeleton system 100 can comprise a plurality of accelerometers, force sensors, position sensors, and the like, at various suitable positions, including at the arms 115, 120, joint 125, actuators 130 or any other location. Accordingly, in some examples, sensor data can correspond to a physical state of one or more actuators 130, a physical state of a portion of the exoskeleton system 100, a physical state of the exoskeleton system 100 generally, and the like. In some embodiments, the exoskeleton system 100 can include a global positioning system (GPS), camera, range sensing system, environmental sensors, elevation sensor, microphone, thermometer, or the like. In some embodiments, the exoskeleton system 100 can obtain sensor data from a user device such as a smartphone, or the like.

In some cases, it can be beneficial for the exoskeleton system 100 to generate or augment an understanding of a user 101 wearing the exoskeleton device 100 of the environment and/or operation of the exoskeleton system 100 through integrating various suitable sensors 515 into the exoskeleton system 100. One embodiment can include sensors 515 to measure and track indicators to observe various suitable aspects of user 101. These indicators can include biological indicators such as body temperature, heart rate, respiratory rate, blood pressure, blood oxygenation saturation, expired $CO_2$, blood glucose level, sweat rate, muscle activation, EMG, EKG, muscle fatigue, joint rotational speeds and accelerations, and the like, and performance indicators such as balance, agility, gait speed, time to complete a physical task, time to complete a cognitive task and the like.

In some embodiments, the exoskeleton system 100 can take advantage of the relatively close and reliable connectivity of such sensors 515 to the body of the user 101 to record system vitals and store them in an accessible format (e.g., at the exoskeleton device, a remote device, a remote server, or the like). Another embodiment can include environmental sensors 515 that can continuously or periodically measure the environment around the exoskeleton system 100 for various environmental conditions such as temperature, humidity, light level, barometric pressure, radioactivity, sound level, toxins, contaminants, or the like. In some examples, various sensors 515 may not be required for operation of the exoskeleton system 100 or directly used by operational control software, but can be stored for reporting to the user 101 (e.g., via an interface 515) or sending to a remote device, a remote server, or the like.

The pneumatic system 520 can comprise any suitable device or system that is operable to inflate and/or deflate the actuators 130 individually or as a group. For example, in one embodiment, the pneumatic system can comprise a diaphragm compressor as disclosed in related patent application Ser. No. 14/577,817 filed Dec. 19, 2014, or a pneumatic power transmission as discussed herein.

Figure 6:
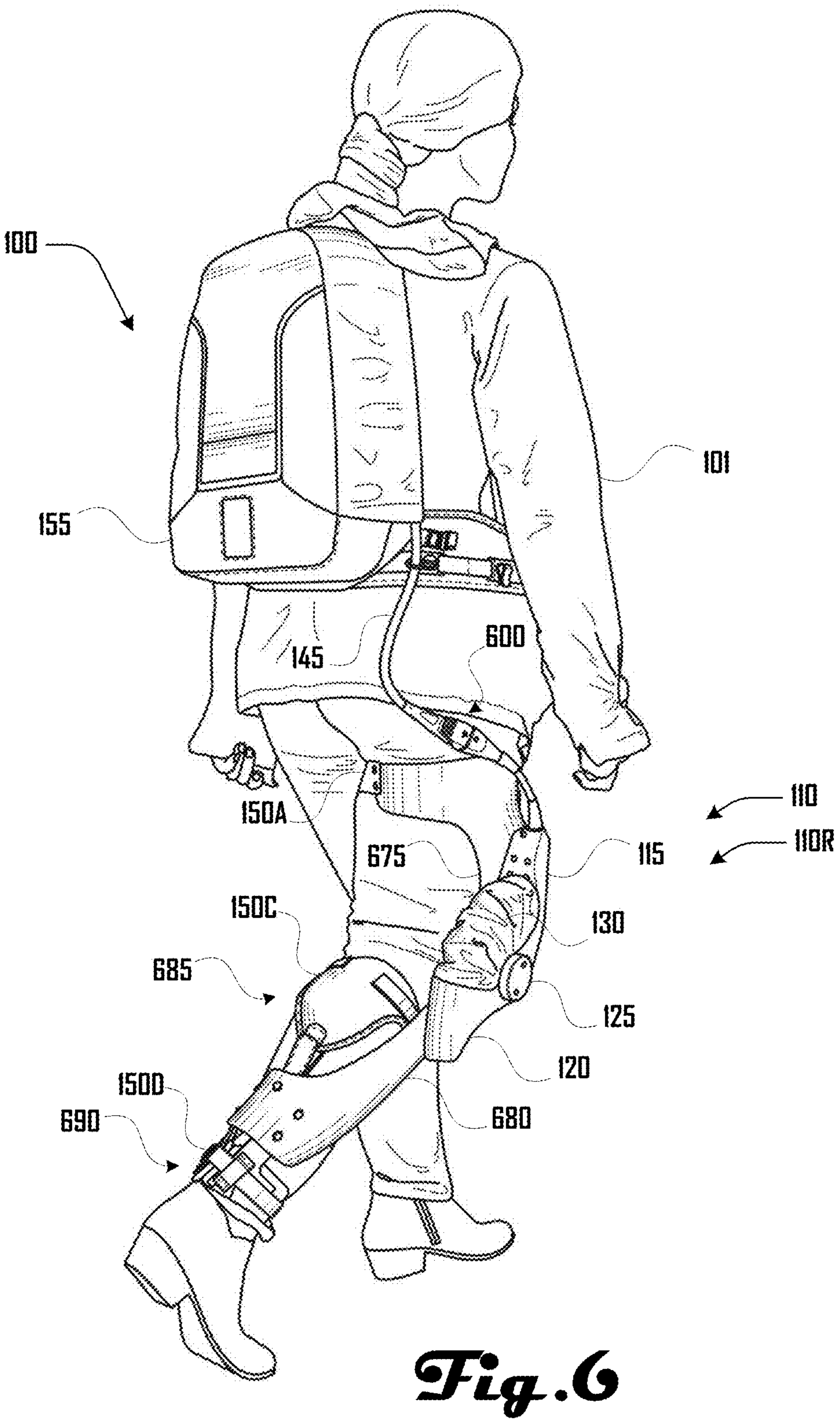
FIG. 6 is a rear view of another embodiment of an exoskeleton system including a leg actuator unit coupled to the right leg of a user.
Figure 7:
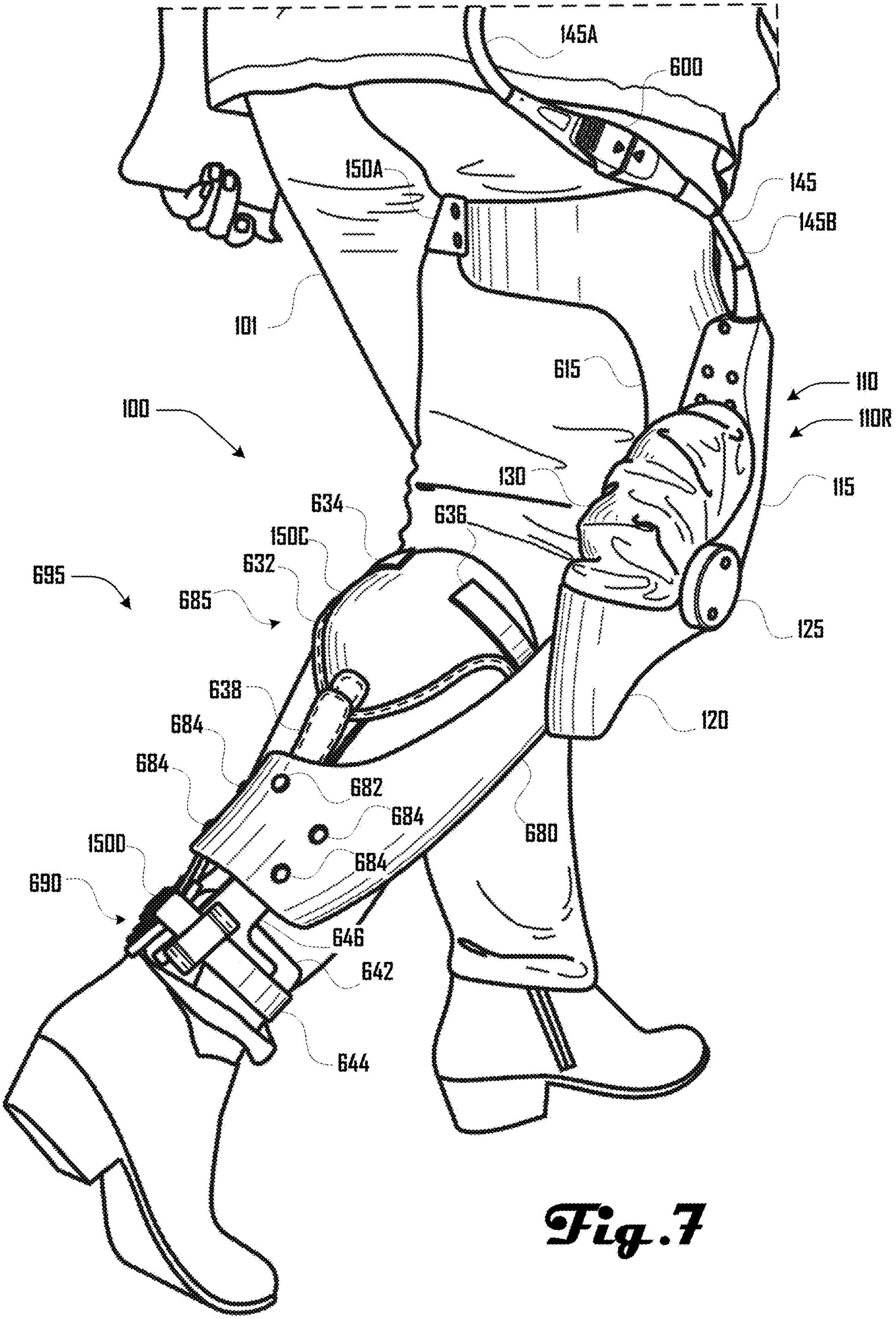
FIG. 7 is a close-up view of a portion of the illustration of FIG. 6.
Figure 8:
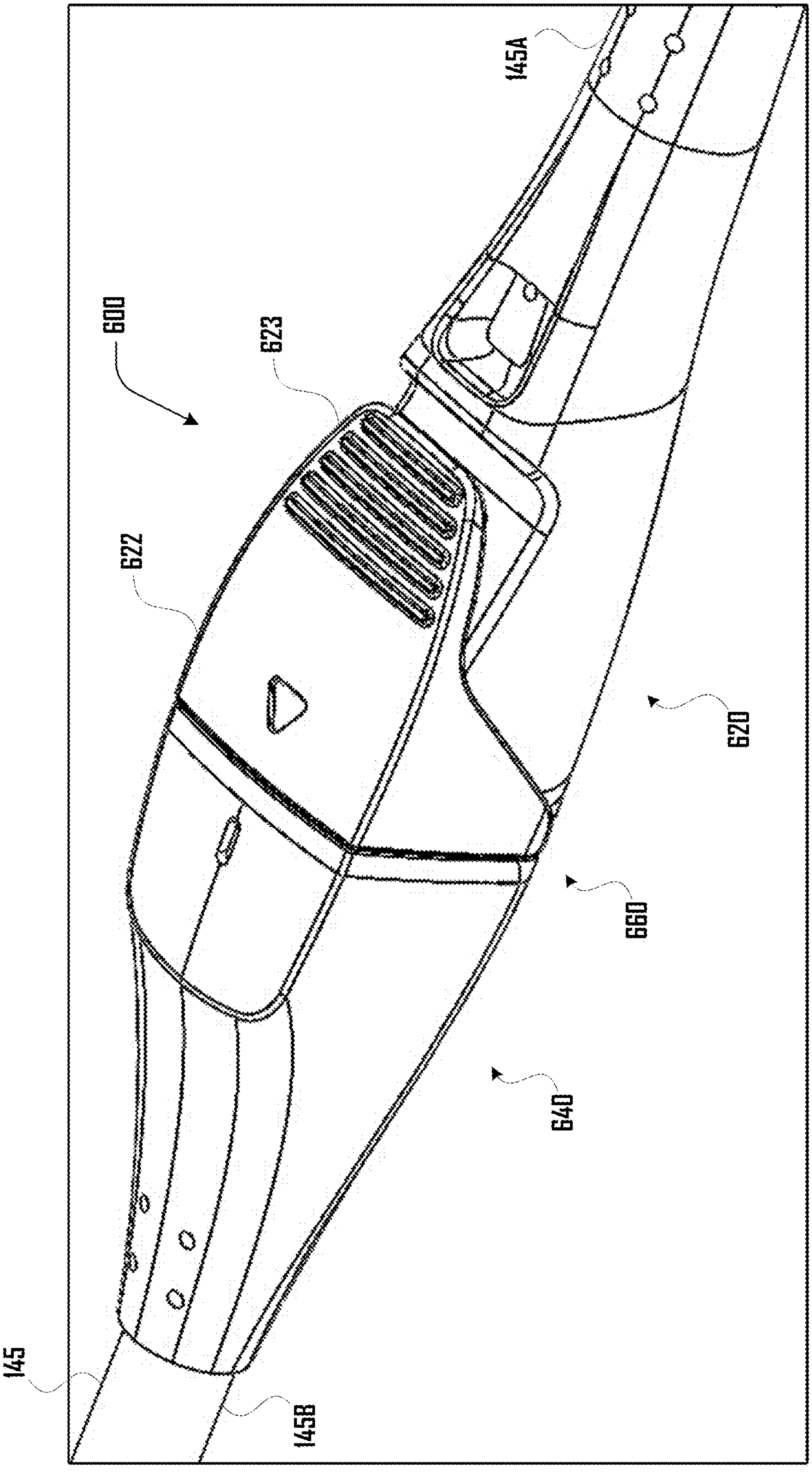
FIG. 8 illustrates a perspective view of a cable connector of one embodiment.
Figure 9:
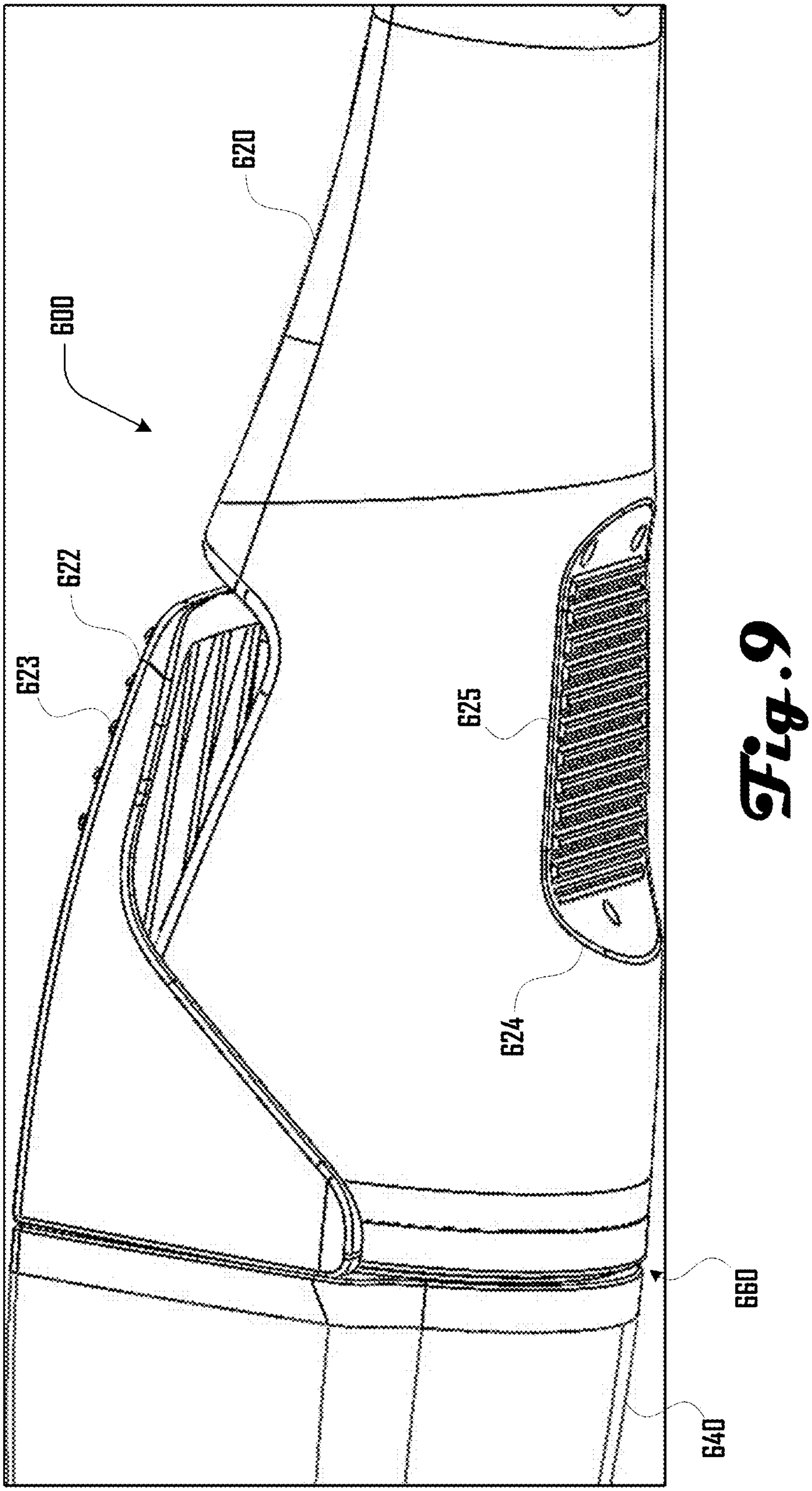
FIG. 9 illustrates another perspective view of the cable connector of the embodiment of FIG. 8.

Turning to FIGS. 6 and 7, another embodiment of an exoskeleton system 100 is illustrated. In this example embodiment, the exoskeleton system 100 includes a single right leg actuator unit 110; however, it should be clear that this example embodiment can be extended to an exoskeleton system 100 having both a left and right actuator unit 110L, 110R or only a left actuator unit 110L. Accordingly the example of FIGS. 6 and 7 should not be construed as limiting, and in further embodiments, any suitable elements can be present in a suitable plurality, absent, or interchanged with elements of other embodiments (e.g., FIGS. 1-4), or the like.

As shown in FIGS. 6 and 7, the leg actuator unit 110 can include an upper arm 115 and a lower arm 120 that are rotatably coupled via a joint 125. A bellows actuator 130 extends between the upper arm 115 and lower arm 120. A cable 145 can be coupled to the bellows actuator 130 to provide power, communication and/or introduce and/or remove fluid from the bellows actuator 130 to cause the bellows actuator 130 to expand and contract and to stiffen and soften, as discussed herein. As shown in the example of FIGS. 6 and 7, the cable 145 can comprise a cable connector 600 that can define a releasable coupling along a portion of the cable 145 with first and second cable portions 145A, 145B on opposing sides of the cable connector 600. As discussed in more detail herein, in various embodiments, the cable connector 600 can provide for a releasable coupling of a unified unitary cable 145 that comprises elements for fluid transfer, electrical power transfer and/or communications to, from or between the exoskeleton device 510 (e.g., disposed in the backpack 155) and an exoskeleton unit 110 and/or actuator 130 as discussed herein. In some embodiments, the cable connector 600 can couple directly with the exoskeleton device 510 (e.g., disposed in the backpack 155) or exoskeleton unit 110 and/or actuator 130 such that only a single cable portion 145A or 145B extends from the cable connector 600.

A backpack 155 can be worn by the user 101 (see FIG. 6) and can hold various components of the exoskeleton system 100 such as a fluid source, control system, a power source, exoskeleton device, pneumatic system, and the like as discussed herein. For example, in some embodiments, the backpack 155 can comprise or store one or more of the components of an exoskeleton device 510 (see e.g., FIG. 5).

As shown in FIGS. 6 and 7, the leg actuator unit 110 can be coupled about the right leg of the user 101 with the joint 125 positioned at the right knee 103R of the user 101 (see FIGS. 1-3 for labeling of body parts of the user 101), with the upper arm 115 of the leg actuator unit 110R being coupled about the right upper-leg portion 104R of the user 101 via one or more couplers 150 (e.g., straps that surround the legs 102). The lower arm 120 of the leg actuator unit 110 can be coupled about the right lower-leg portion 105R of the user 101 via one or more couplers 150.

The upper and lower arms 115, 120 of a leg actuator unit 110 can be coupled about the leg 102 of a user 101 in various suitable ways. For example, FIGS. 6 and 7 illustrate an example where the upper and lower arms 115, 120 and joint 125 of the leg actuator unit 110 are coupled along lateral faces (sides) of the top and bottom portions 104, 105 of the leg 102. As shown in the example of FIGS. 6-9, the upper arm 115 can be coupled to the upper-leg portion 104 of a leg 102 above the knee 103 via one coupler 150 and the lower arm 120 can be coupled to the lower-leg portion 105 of a leg 102 below the knee 103 via two couplers 150.

Specifically, the upper arm 115 can be coupled to the upper-leg portion 104 of the leg 102 above the knee 103 via a first upper-leg coupler 150A. The first upper-leg coupler 150A can be associated with a rigid upper-leg brace 675 disposed on and engaging a lateral side of the upper-leg portion 104 of the leg 102, with a strap of the first upper-leg coupler 150A extending around the upper-leg portion 104 of the leg 102. The upper arm 115 can be coupled to the rigid upper-leg brace 675 on a lateral side of the upper-leg portion 104 of the leg 102, which can transfer force generated by the actuator 130 through the upper arm 115 to the upper-leg portion 104 of the leg 102.

The lower arm 120 can be coupled to the lower-leg portion 105 of a leg 102 below the knee 103 via a second set of couplers 695 that includes first and second lower-leg couplers 150C, 150D. The first and second lower-leg couplers 150C, 150D can be associated with a rigid lower-leg brace 680 disposed on and engaging a lateral side of the lower-leg portion 105 of the leg 102. The lower arm 120 can be coupled to the rigid lower-leg brace 680 on a lateral side of the lower-leg portion 105 of the leg 102, which can transfer force generated by the actuator 130 through the lower arm 120 to the lower-leg portion 105 of the leg 102. The rigid lower-leg brace 680 can extend downward from a coupling with the lower arm 120 at a lateral position on the lower-leg portion 105 of the leg 102, with a portion of the rigid lower-leg brace 680 curving toward the posterior (back) of the lower-leg portion 105 to attachments 682, 684 that couple one or more portions of the first and second lower-leg couplers 150C, 150D to the rigid lower-leg brace 680.

The first lower-leg coupler 150C can include a calf-coupling assembly 685 that includes a calf brace 632 that is coupled to the rigid lower-leg brace 680 via a first, second and third calf strap 634, 636, 638. For example, as shown in the example of FIGS. 6 and 7, the first and second calf straps 634, 636 can extend horizontally from opposing lateral sides of an upper portion of the rigid lower-leg brace 680 from an internal face of the rigid lower-leg brace 680. The third calf strap 638 can extend vertically from a lower posterior portion of the rigid lower-leg brace 680 from an internal face of the rigid lower-leg brace 680 where the third calf strap 638 is coupled to the rigid lower-leg brace 680 via a first set of one or more attachments 682. In various embodiments, the calf brace 632 can be a rigid or flexible element and can comprise materials such as a fabric, plastic, carbon-fiber, or the like. These examples in no way limit the possible configurations of the calf strap, including the number of straps, which may vary from 1, 2, 3, 5, 6, 10 and the like; their extension direction from the upper portion and/or lower portion of the rigid lower-leg brace 680; and whether they extend from an internal or external face or edge of the rigid lower-leg brace 680.

The calf straps 634, 636, 638 can be configured in various suitable ways and can include various suitable mechanisms that allow the calf straps 634, 636, 638 to be tightened, loosened, extended, shortened, removed, or the like. For example, in some embodiments, the first and second calf straps 634, 636 comprise hook and loop tape (e.g., Velcro) that allows the second calf straps 634, 636 to be tightened, loosened, extended, shortened, or the like. In some embodiments, the third calf strap 638 can comprise a strap cinch, or the like, that allows the third calf strap 638 to be tightened, loosened, extended, shortened, or the like.

The second lower-leg coupler 150D can comprise an ankle-coupling assembly 690 that includes a cuff 642 that extends around and surrounds the lower-leg portion 105 in proximity to the ankle of the user 101, including on, above or below the ankle within 0 mm, 6 mm, 1 cm, 5 cm, 10 cm, and held via an ankle strap 644. The cuff 642 can be coupled to the rigid lower-leg brace 680 via one or more coupling tabs 646 that extend vertically from the cuff 642, with the one or more coupling tabs 646 coupled to the rigid lower-leg brace 680 via a second set of one or more attachments 64 on an internal face of the rigid lower-leg brace 680. In some embodiments, the coupling tab 646 is fixed relative to the rigid lower-leg brace 680, which in turn fixes the position of the ankle-coupling assembly 690 relative to the rigid lower-leg brace 680. In other embodiments, the coupling tab is semi-rigidly fixed to the rigid lower-leg brace 680, allowing for adjustment of the ankle-coupling assembly 690 position relative to the rigid lower-leg brace 680. In some embodiments of this, the adjustment is done manually, such as by loosening and tightening an adjustment screw, by the user, someone trained in the fitting of the device to the user, or another person and the like, or the adjustment is controlled by the exoskeleton system through such means as a rack and pinion gear driven by a motor and the like. In other embodiments, the coupling tab remains free to move relative to the rigid lower-leg brace 680, allowing for dynamic adjustment of the ankle-coupling assembly 690 position relative to the rigid lower-leg brace 680 which can accommodate the movements of the user. The ankle strap 644 can include various suitable elements that allow the ankle strap to be tightened, loosened, extended, shortened, removed or the like (e.g., hook and loop tape, strap cinch, or the like).

In various embodiments, the rigid upper-leg and lower-leg braces 675, 680 can be made of various suitable materials such as a plastic, carbon-fiber, metal, wood, or the like. As discussed herein, in some embodiments the upper-leg and/or lower-leg braces 675, 680 can be formed to match the contours of the legs 102 of the user 101, which can be desirable for increasing comfort for the user 101 maximizing surface area of the upper-leg and/or lower-leg braces 675, 680 engaging the legs 102 of the user 101, and the like. In some examples, the upper-leg and/or lower-leg braces 675, 680 can be formed specifically for a given user 101, which can include molding to user body parts, scanning the user's body and generating upper-leg and/or lower-leg braces 675, 680 from such scan data, and the like. In some examples, the upper-leg and/or lower-leg braces 675, 680 can be formed specifically for a given set of users 101, such as those with similar body morphologies such that they can be used to fit segments of the user population.

In some embodiments, alignment and suspension of one or more actuation units 110 on the leg 102 (or other body parts) of a user 101 can be achieved in some examples via a strap connected at the lower-leg 105 just above the ankle of the user 101. For example, such a strap can be firmly placed in a supra-malleolar location that is located above the malleolus (protruding bones at the ankle) and below the bulk of the calf muscle. Such a strap can be connected in a firm connection such that it lies in a narrowing diameter portion of the user's leg 102. For example, coupler 150D of FIGS. 1-4, 6 and 7 and/or ankle coupling assembly 690 of FIGS. 6 and 7 can be configured in such a way. Such a connection method can be beneficial in some examples by having no portion of the actuator unit 110 (or at least no substantive portion used for coupling) extending below the ankle of the user 101 to interface with the user's foot, user's footwear, the ground, or area below the malleolus. In some examples, where the user's footwear extends to a supra-malleolar location, it can be advantageous to interact with the footwear, the advantages including but not limited to improving comfort, reducing irritation, increasing friction and suspension of the actuation unit 110, reducing the accuracy needed in the location of the ankle coupling assembly 690 on the lower-leg 105, and the like.

While various embodiments discussed and illustrated herein can relate to exoskeleton systems 100 configured for users 101 having all conventional body parts, further embodiments can include exoskeleton systems configured to be worn by users 101 that are amputees or persons who otherwise do not have all conventional body parts (e.g., a person who is missing one or more toe, foot, lower leg, leg, knee joint, finger, hand, distal portion of an arm, elbow joint, arm, or the like).

Figures 10A, 10B:
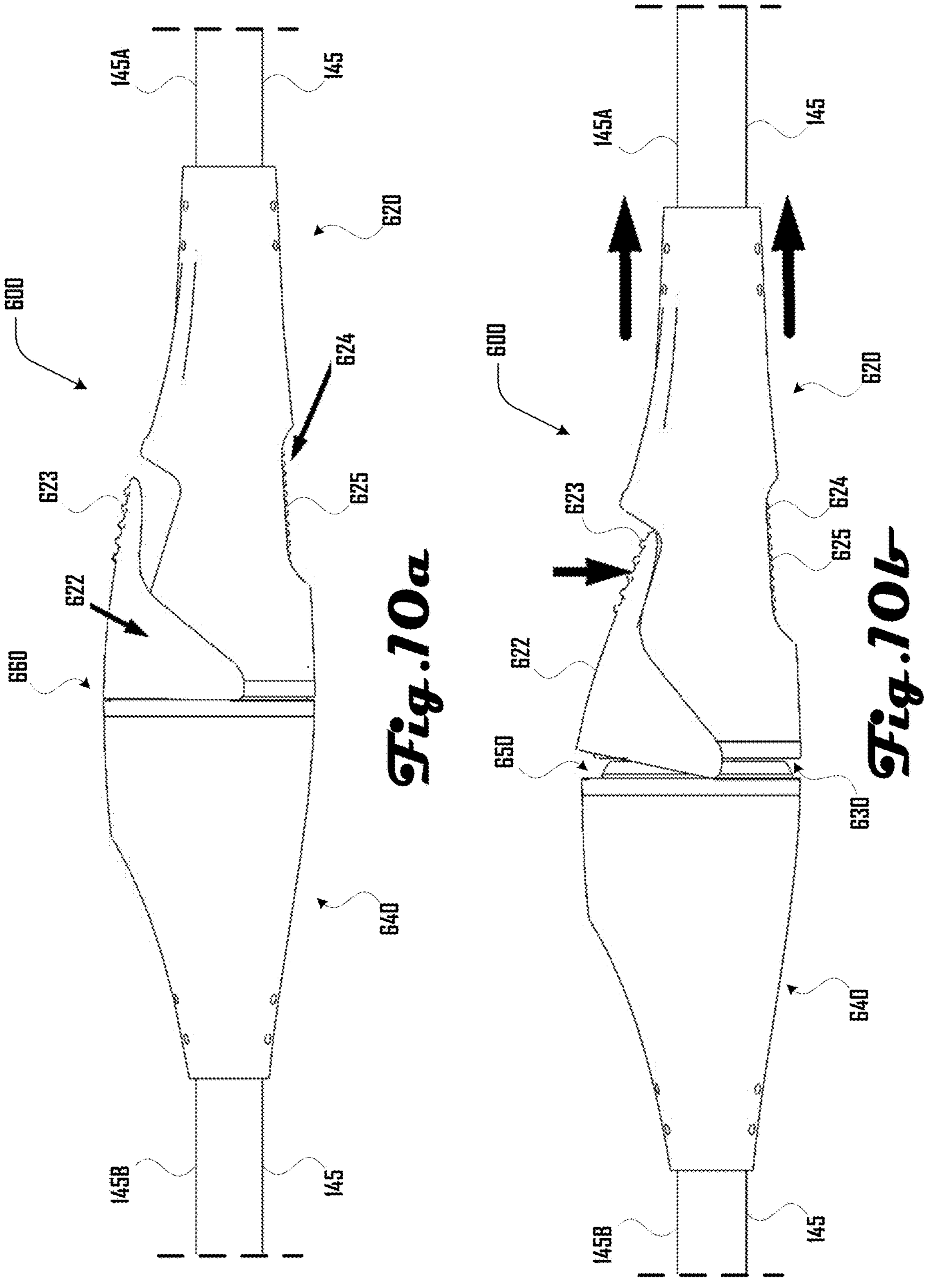
FIG. 10*a* illustrates a configuration of an embodiment of a cable connector where first and second connector sides are coupled.
FIG. 10*b* illustrates a configuration of the cable connector of FIG. 10*a* where a release button has been rotatably actuated to push coupling faces away from each other to disengage a coupling between the first and second connector sides.
Figure 11:
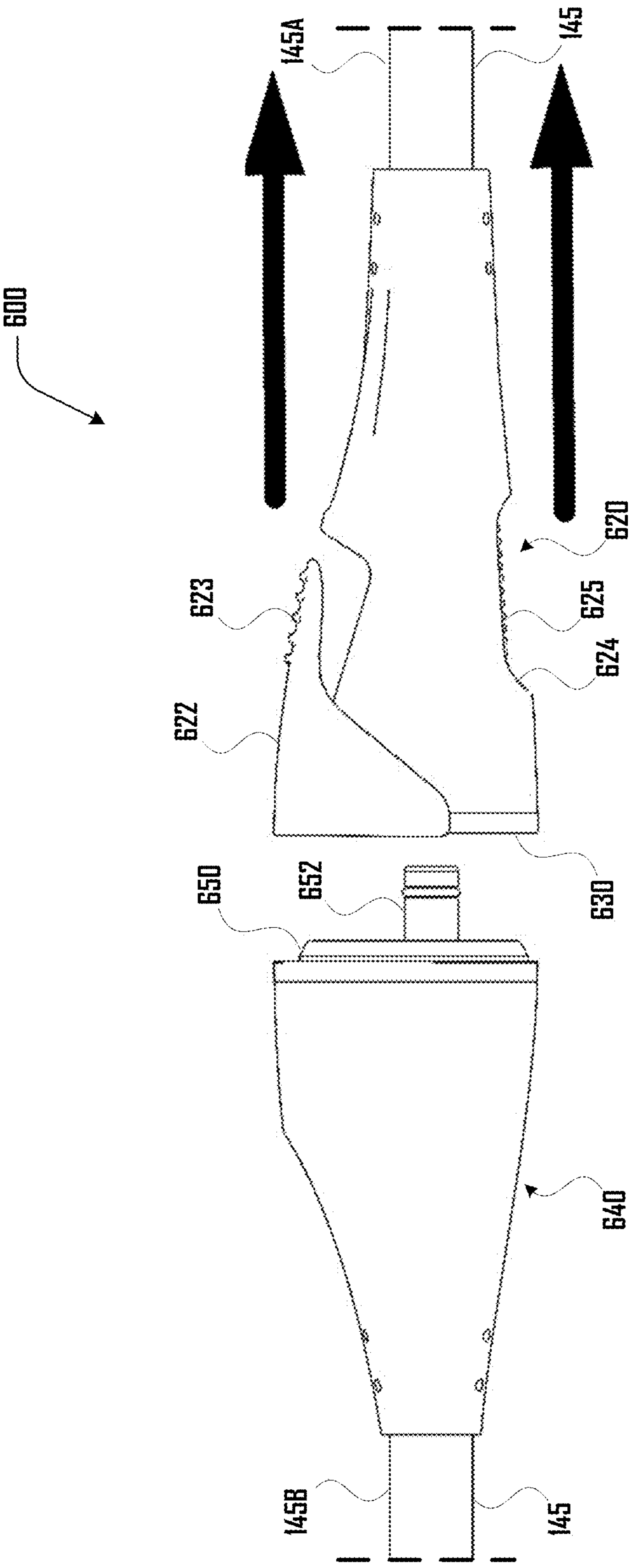
FIG. 11 illustrates an example configuration of the cable connector of FIGS. 10*a* and 10*b* where the coupling between the first and second connector sides becomes disengaged without the release button being pressed.

Turning to FIGS. 8, 9, 10*a*, 10*b* and 11, an example embodiment of a cable connector 600 is illustrated that comprises a first and second connector side 620, 640 that are configured to generate a coupling 660 of the first and second connector sides 620, 640 that operably couples the first and second cable portions 145A, 145B of the cable 145 and first and second coupling faces 630, 650 of the first and second connector sides 620, 640 respectively. As shown in FIG. 11, the second connector side 640 can comprise a fluid stem 652 extending from the second coupling face 650 that can be configured to couple with a fluid port of the first connector side 620 to generate an operable fluid coupling (e.g., gas or air coupling) between the first and second connector sides 620, 640.

In the example of FIGS. 8, 9, 10*a*, 10*b* and 11, the first connector side 620 comprises a release button 622 and an opposing grip 624. In various embodiments, the grip 624 can have a gripping face 625 that is generally parallel to a release arm 623 of the release button 622 on an opposing side of the first connector side 620. Such a configuration of the grip 624 and release button 622 can be desirable for allowing a user to grip the first connector side 620 and actuate the release button 622 via the release arm 623.

For example, FIG. 10*a* illustrates a configuration where the first and second connector sides 620, 640 are coupled. For example, as discussed in more detail herein, in some embodiments the first and second connector sides 620, 640 can be held together via a magnetic coupling between the first and second connector sides 620, 640 (e.g., complementary cylindrical magnets at the first and second connector sides 620, 640). In some embodiments, such a coupling can be only or substantially only via such a magnetic coupling, but further embodiments can comprise various suitable coupling elements such as a fiction fit, latch, hook and loop tape, or the like.

In one embodiment, a large flexible body is formed over the respective first and second connector sides 620, 640. Such a body can help with strain relief due to its flexible nature in some examples. In addition, such moldings may use an ergonomic grip shape to enhance user comfort in some examples. A large ergonomic grip can also make it easier to hold and perform connect and disconnect operations in some examples. Aesthetic addons are a design option for the over-molding, such as texturing, shaped grip feature, iconography, and alignment markers. Various other types of first and second connector sides 620, 640 can be used in further embodiments, including, but not limited to, field-assembled strain-reliefs, and the like.

Turning to FIG. 10*b*, a configuration of the first and second connector sides 620, 640 is shown where the release button 622 has been rotatably actuated (e.g., by pushing the release arm 623) such that the release button 622 pushes coupling faces 630, 650 away from each other to disengage the coupling 660 between the first and second connector sides 620, 640. For example, in various embodiments, the release button 622 can push against the second connector face 650 of the second connector side 640 with sufficient force to overcome a magnetic coupling between the first and second connector sides 620, 640 such that the coupling 660 between the first and second connector sides 620, 640 can be disengaged and the coupling 660 between the first and second connector sides 620, 640 can be separated.

In various embodiments, the coupling 660 between the first and second connector sides 620, 640 can be configured to un-mate when a sufficiently forceful tension is applied to the cable 145 and/or cable connector 600 and without pressing the release button 622. For example, FIG. 11 illustrates an example where the coupling 660 between the first and second connector sides 620, 640 becomes disengaged without the release button 622 being pressed.

In various embodiments pushing the release button 622 can allow the coupling 660 between the first and second connector sides 620, 640 to disengage with a first lower tension force than a second higher minimum tension force required to disengage the first and second connector sides 620, 640 without pressing the release button 622. Such an embodiment can be desirable by allowing a user to selectively and easily disconnect the cable connector 600 by pressing the release button 622 by hand while also providing a safety disconnect function that allows the cable connector 600 to disengage when the cable 145 and or cable connector 600 experiences a sufficient pulling force. This can allow the cable connector 600 to safely disengage at a desired amount of force to prevent damage to the cable 145, the cable connector 600 or connections to the backpack 155, exoskeleton device 510, leg actuator unit(s) 110, actuator(s) 130 or the like.

Figure 12:
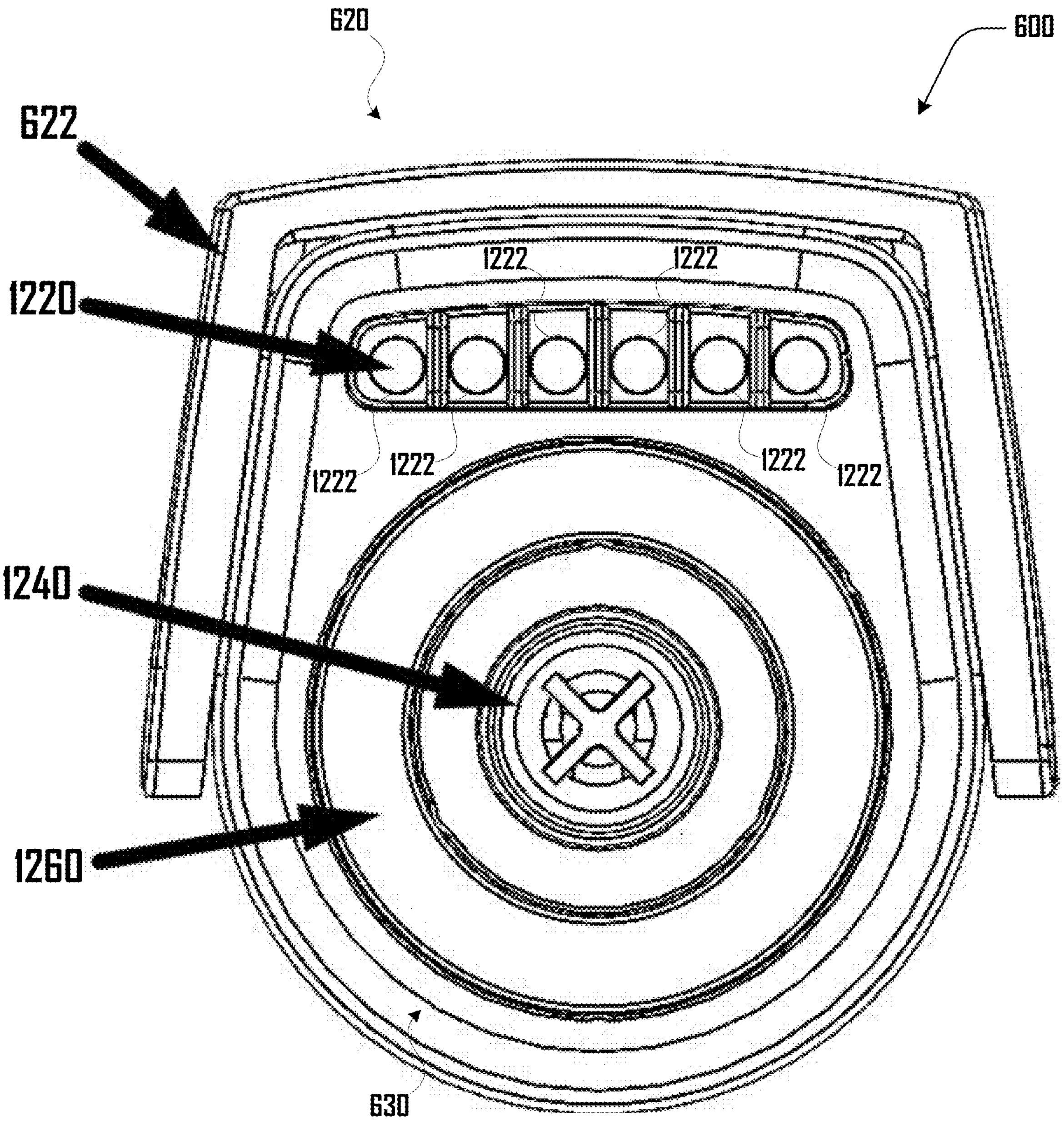
FIG. 12 illustrates an example embodiment of a first coupling face of a first connector side of a cable connector that comprises a pin array, a fluidic connector and a coupling magnet.
Figure 13:
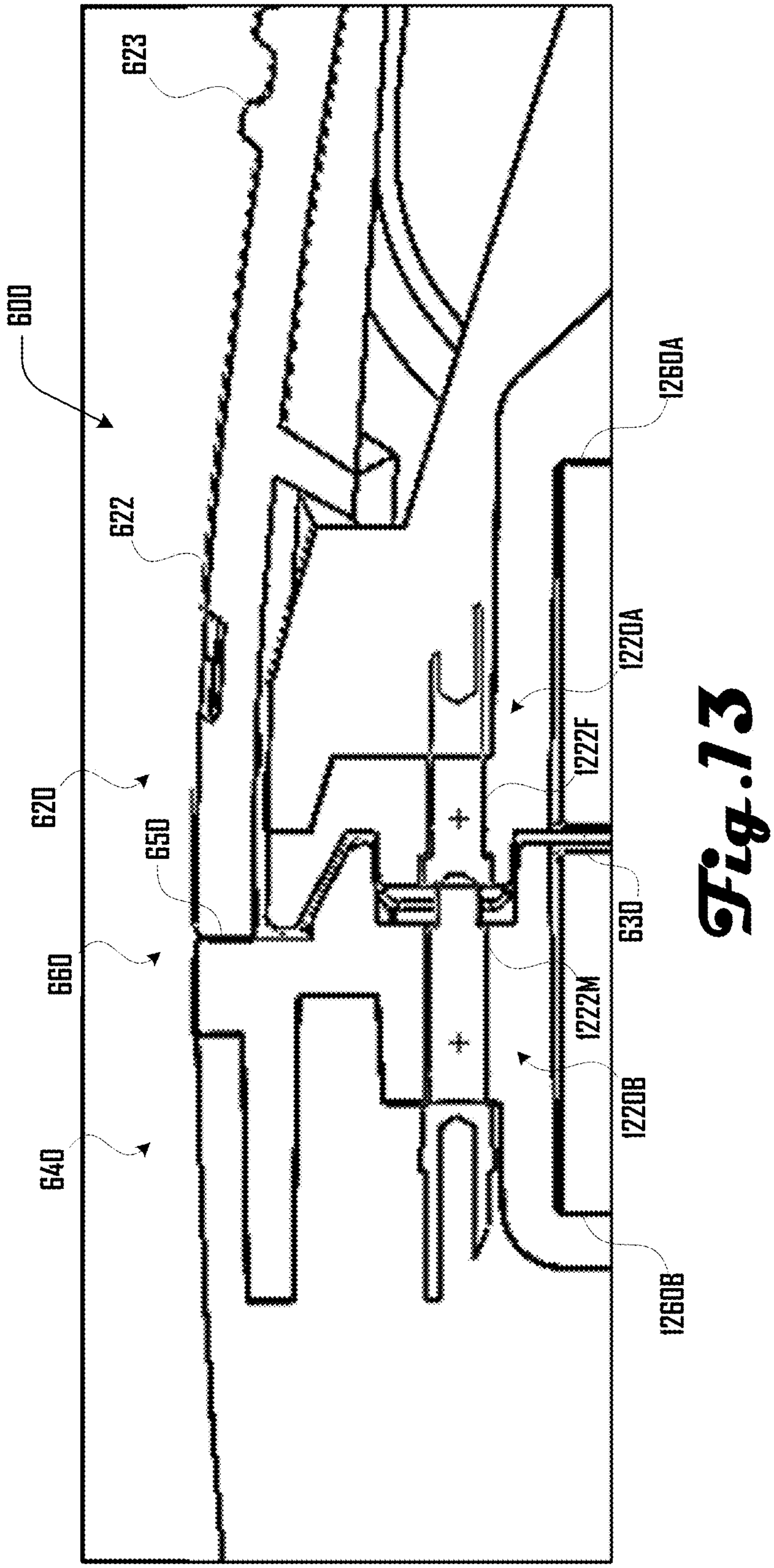
FIG. 13 illustrates first and second pin arrays of first and second connector sides with a male pin of the second connector side coupling with a female pin of the first connector side.

Turning to FIG. 12, an example embodiment of a first coupling face 630 of a first connector side 620 of a cable connector 600 is illustrated, which comprises a pin array 1220, a fluidic connector 1240 and a coupling magnet 1260. In various embodiments, the pin array can comprise a plurality of male and/or female pins 1222 that are configured to operably couple with complementary male and/or female pins 1222 on the second coupling face 650 of the second connector side 640. For example, FIG. 13 illustrates first and second pin arrays 1220A, 1220B of the first and second connector sides 620, 640 with a male pin 1222M of the second connector side 640 coupling with a female pin 1222F of the first connector side 620.

As discussed herein, the operable coupling of the male and/or female pins 1222 can be configured to communicate electrical power, communication signals, or the like, as discussed herein, which can include via one or more electrical power lines, one or more fluid lines, and/or one or more communication lines that can be unified within a cable 145. In some embodiments a given pin 1222 can be dedicated to a specific function, such as transmitting electrical power to a leg actuator unit 110 and/or actuator 130 from the exoskeleton device 510; transmit control signals from the exoskeleton device 510 to the leg actuator unit 110 and/or actuator 130; transmit sensor data from a sensor of the leg actuator unit 110 and/or actuator 130 to the exoskeleton device 510, and the like. In various embodiments, connectors can be configured to couple any suitable number of one or more electrical power lines, one or more fluid lines, and/or one or more communication lines that may be unified within a cable 145 (e.g., 1, 2, 3, 4, 5, 6, 7, 8, 9, 10, 15, 20, 25, 50, 100, or the like). For example, in some embodiments, the unified cable 145 can enclose within a sheath a single power line, five communication lines, and a single fluidic line.

It can be desirable in various examples for a connection between pins 1222 and/or a pin array 1220 to be able to hold an electrical connection to transfer power and data under mechanical shock and vibration, (e.g., because the user may constantly be moving during certain types of use). In a preferred embodiment, the electrical connection uses spring-loaded pins and/or target pins. Spring-loaded pins can have integrated springs which can help counteract movement by the user and can prevent intermittent disconnection in various embodiments. In one such embodiment, the cable from the power pack contains six spring-loaded pins 1222 in a pin array 1220 that come into contact with six target pins 1222 on the connection from the brace. To provide further protection to the pins, the spring-loaded pins can be recessed into the cable connector 600 in some embodiments. In various examples, due to the recessed spring-loaded pins, the target pins can be extruding from their connector. There are various options for such connections, including but not limited to blade contacts, barrel contacts, sliding concentric rings, leaf-spring contacts, USB connections, wireless connections, pin and socket connections, light connections, and the like.

While the example of FIG. 12 illustrates a pin array 1220 having a line of six pins 1222, it should be clear that further embodiments can comprise any suitable number of pins such as 1, 2, 3, 4, 5, 6, 7, 8, 9, 10, 15, 20, 25, 50, 100, or the like. Additionally, further embodiments can comprise any suitable structures or elements configured to be operably coupled and decoupled to communicate electrical power, communications, or the like. Accordingly, the example pin array 1220 of FIG. 12 should not be construed to be limiting.

As shown in the example of FIG. 12, the first coupling face 630 of a first connector side 620 of a cable connector 600 can comprise a fluidic connector 1240 that is surrounded by a coupling magnet 1260. As shown in the example of FIG. 12, the coupling magnet can be a continuously cylindrical magnet, which in some examples can be configured to magnetically couple with a complementary continuously cylindrical magnet of the second coupling face 650 of the second connector side 640. For example, FIG. 13 illustrates a first and second magnet 1260A, 1260B of the first and second connector sides 620, 640. Further embodiments can comprise any suitable plurality of coupling magnets 1260 in any suitable configuration, so the example of FIG. 12 should not be construed to be limiting.

Additionally, while one or more magnets 1260 can be used to couple the first and second connector sides 620, 640, one or more additional or alternative coupling methods can be used. In some examples, constant movement of a user could potentially cause the connector to pull apart, so it can be desirable in various embodiments for the connection to be strong enough to hold together when the user is moving.

In another embodiment, the connector ends are held together by spring latches. In such an embodiment, the user can push the connector ends together and a spring latch can automatically lock them together. The spring latch can be released in some examples by pressing down on one end. In another embodiment, over-center latches are used to hold the connector. In such an embodiment, the user can hold the two connector ends together and can manually flip a latch over both ends to lock the connector. In another embodiment, a traverse sliding collar may be used. In such an embodiment the connector faces can be put together and a collar can slide over the point of connection and tightly fit all around it. The fit in various examples can be tight enough so the connection will not come loose. There are various retention methods that may be used, including but not limited to snap-hook latches, multiple magnets on connector faces, multi-shaped magnets, over-center latches, partial-turn latches or friction latches.

The fluidic connector 1240 in various embodiments can be configured to operably couple with the fluid stem 652 of the second connector side 640 to generate a sealed connection therebetween and allow fluid (e.g., air) to be transmitted to the actuator unit 110 and/or actuator 130 from a fluid source, exoskeleton device 510, or the like as discussed herein. In various embodiments, the fluidic connector 1240 and/or fluid stem 652 can comprise an automatic shutoff valve such that when the cable connector 600 is disconnected and the fluidic connector 1240 and fluid stem 652 become disconnected, the shutoff valve closes to prevent fluid from escaping from the end of the fluidic connector 1240 and/or fluid stem 652. Similarly, in various embodiments, connecting the fluidic connector 1240 and fluid stem 652 can automatically make a fluidic coupling between the fluidic connector 1240 and fluid stem 652 operable.

Fluidic cables running from the exoskeleton device 510 to the actuator unit 110 and/or actuator 130 can be connected so fluid can travel to the actuator 130 and move the actuator unit 110. In a preferred embodiment, the cable connector 600 can include a single fluidic connection with a spring-loaded valve for fluid transfer. The cable connector 600 can have a leakproof fitting in some examples and may only allow fluid movement when the springs are activated. The connection, in some examples can use a barrel connection, which can move the fluid outlet valve into the grip portion of the cable connector 600 away from the point of connection 660 of the first and second connectors side 620, 640. In various embodiments, this can enhance the leakproof quality of the connection of the cable connector 600. It can be preferred that this connection is molded into the housing of the cable connector 600. Other embodiments can include a discrete fluid connection separate from the housing of the cable connector 600, or multiple separate fluidic connections within the cable connector 600 and/or cable 145.

In various embodiments, all contacts (e.g., electrical, fluidic, communication contact such as a pin array 1220 and/or fluidic connector 1240) are on a single face (e.g., one or both of coupling faces 630, 650) of the cable connector 600 at the end of a pigtail cable 145. In one embodiment, pins 1222 (e.g., respective spring-loaded pins and target pins) are lined up in a single row as a pin array 1220 adjacent to a fluidic contact end, which can be surrounded by a circular magnet 1260. In another embodiment, the fluidic contact is in the center and pins (e.g., spring-loaded pins) may be arranged in a line across the center of one connector end, so that there are equal numbers of pins 1222 on each side of the fluidic contact. On the other connector end in such an embodiment, there can be concentric ring-shaped contacts surrounding the fluidic contact for the spring pins to connect with to complete an electrical connection. The ring-shaped contacts can allow the connector sides 620, 640 to freely rotate and still maintain electrical connection. There are various other ways the contacts may be arranged on the faces 630, 650 of the connector sides 620, 640 including, but not limited to, spring-loaded pins surrounding the fluidic contact, pin and socket contacts around the fluidic contact, a single electrical contact and single fluidic contact beside each other, multiple fluidic contacts and electrical contacts parallel to each other, and the like.

In other embodiments, one or more electrical contact can be on a different face than the fluidic contact or a modular design can be used. In one such embodiment, the fluidic contact can be in line with the cable 145 and the spring-loaded pins are located on the side of the connector end perpendicular to the fluidic contact. Various other embodiments may arrange the electrical contacts on different faces than the fluidic contact, including, but not limited to, placing the electrical contacts on two sides perpendicular to the fluidic contact, or placing the electrical contacts on all sides perpendicular to the fluidic contact. In another embodiment, electrical and fluidic contacts are on two separate cables 145 and two separate connector faces. The two cables 145 can be held together in parallel at the end by a clamshell case with pathways and inlets and outlets for the cables 145.

The structure of the cable connector 600 can hold some or all components of the cable connector 600 together in various embodiments. There are a variety of options available for the structure. A preferred embodiment uses a rigid internal frame onto which electrical and fluidic contacts are installed. As mentioned above, there are many possible layouts that may be used, and the shape of the frame can depend on the one used. The contacts can be installed using adhesives, press-fits, snap hooks, or various other methods. The contacts can also be insert-molded into the rigid internal frame in some examples. After the wires and fluidic tube are assembled onto the contacts, in various embodiments the whole assembly is then over-molded with the flexible strain-relief and made into the desired size and shape, for example a large ergonomic shape. The magnet 1260 can be installed onto the rigid frame using adhesives, press-fits, or other methods. The release button 622 can also be attached to the rigid frame, in some cases by snapping it into place. It is noted that different retention methods or release mechanisms may be used, and as such, a different frame and build procedure can be used in further embodiments. For example, in one embodiment in which a lift latch is used, no magnets are used, a latch mechanism is installed and a finger space for lifting the latch is included in the molding. Other embodiments can include more than one rigid frame, a semi-rigid frame, or no internal frame at all.

While various embodiments can include a cable connector 600 that defines a releasable coupling along a portion of the cable 145 with first and second cable portions 145A, 145B on opposing sides of the cable connector 600 (see e.g., FIGS. 6 and 7), further embodiments can include a cable connector

Figure 14A:
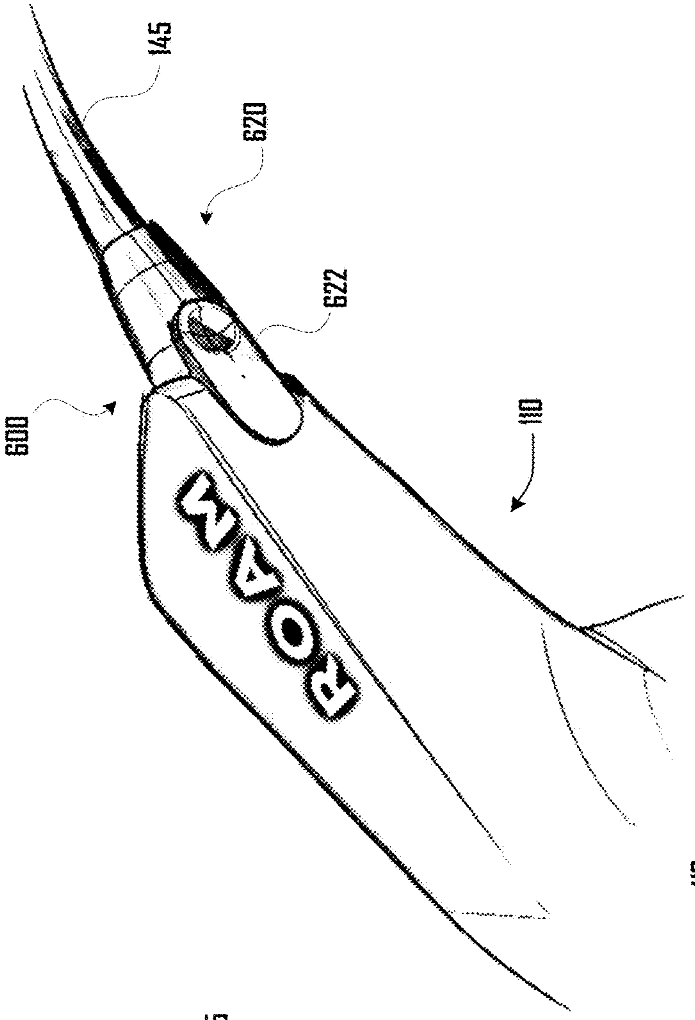
FIGS. 14*a* and 14*b* illustrate one example embodiment of a cable connector that plugs directly into the actuator unit and comprises a release button that allows the first connector side to be operably disengaged and/or operably engaged with the first connector side of the cable connector that plugs directly into the actuator unit.
Figure 14B:
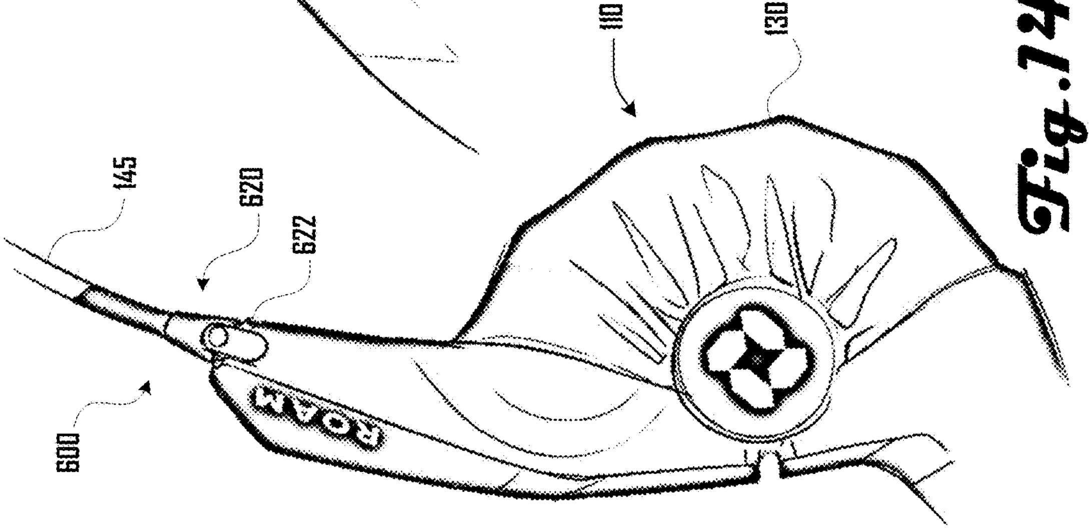

600 that defines a releasable coupling directly with an actuator unit 110 and/or actuator 130. For example, FIGS. 14*a* and 14*b* illustrate one example embodiment of a cable connector 600 that plugs directly into the actuator unit 110 and comprises a release button 622 that allows the first connector side 620 to be operably disengaged and/or operably engaged with the first connector side 620 of the cable connector 600 that plugs directly into the actuator unit 110.

Figures 15A, 15B, 15C:
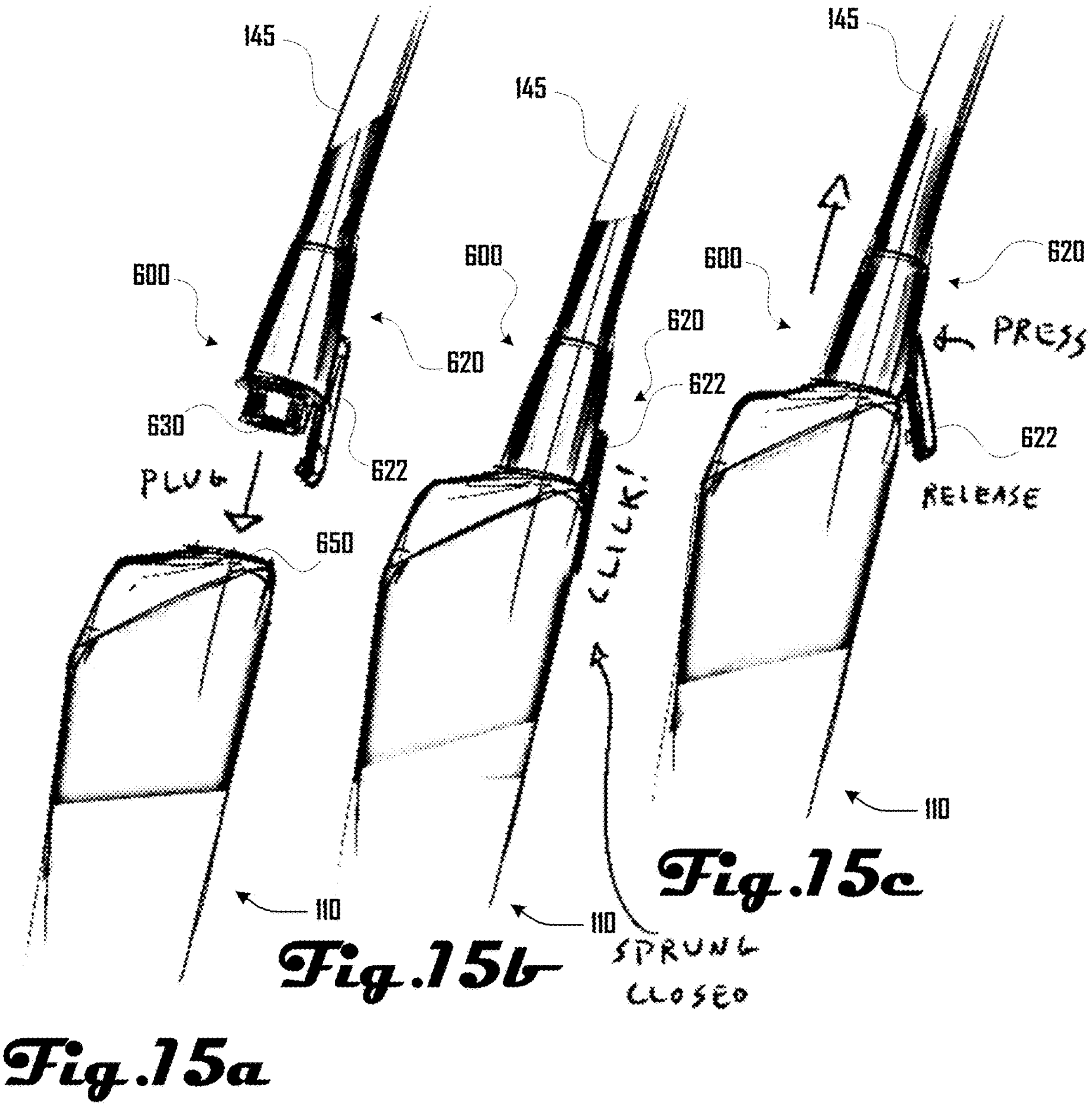
FIGS. 15*a*, 15*b* and 15*c* illustrate another embodiment of a cable connector that plugs directly into the actuator unit and comprises a release button that allows the first connector side to be operably disengaged and/or operably engaged with the first connector side of the cable connector that plugs directly into the actuator unit.
Figure 16B:
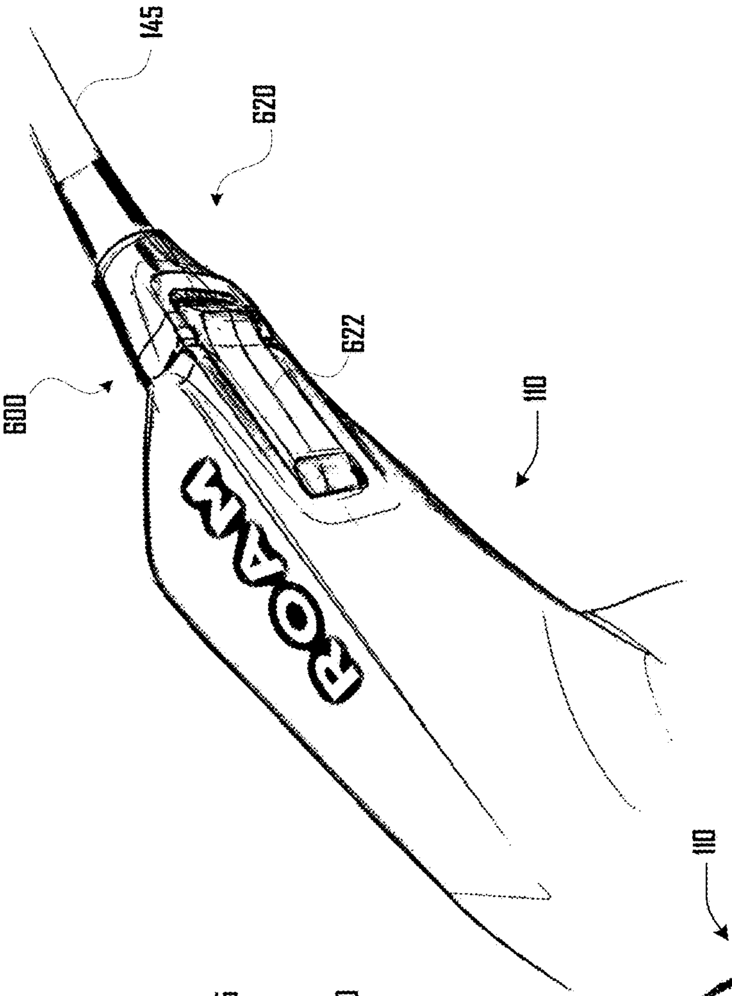
FIGS. 16*a*, 16*b*, 17*a*, 17*b* and 17*c* illustrate another embodiment of a cable connector that plugs directly into the actuator unit and comprises a release button that allows the first connector side to be operably disengaged and/or operably engaged with the first connector side of the cable connector that plugs directly into the actuator unit.
Figure 16A:
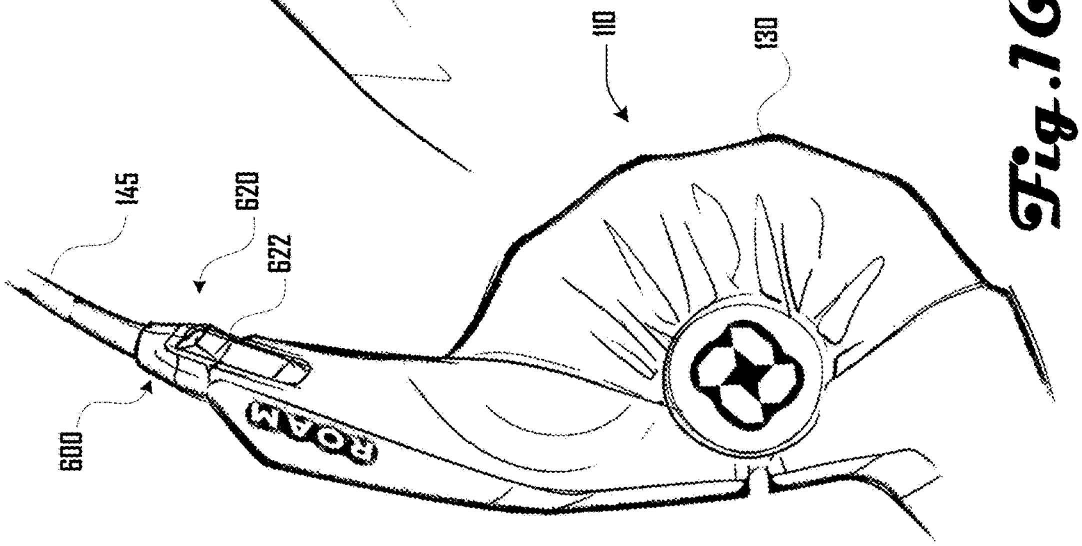
Figures 17A, 17B, 17C:
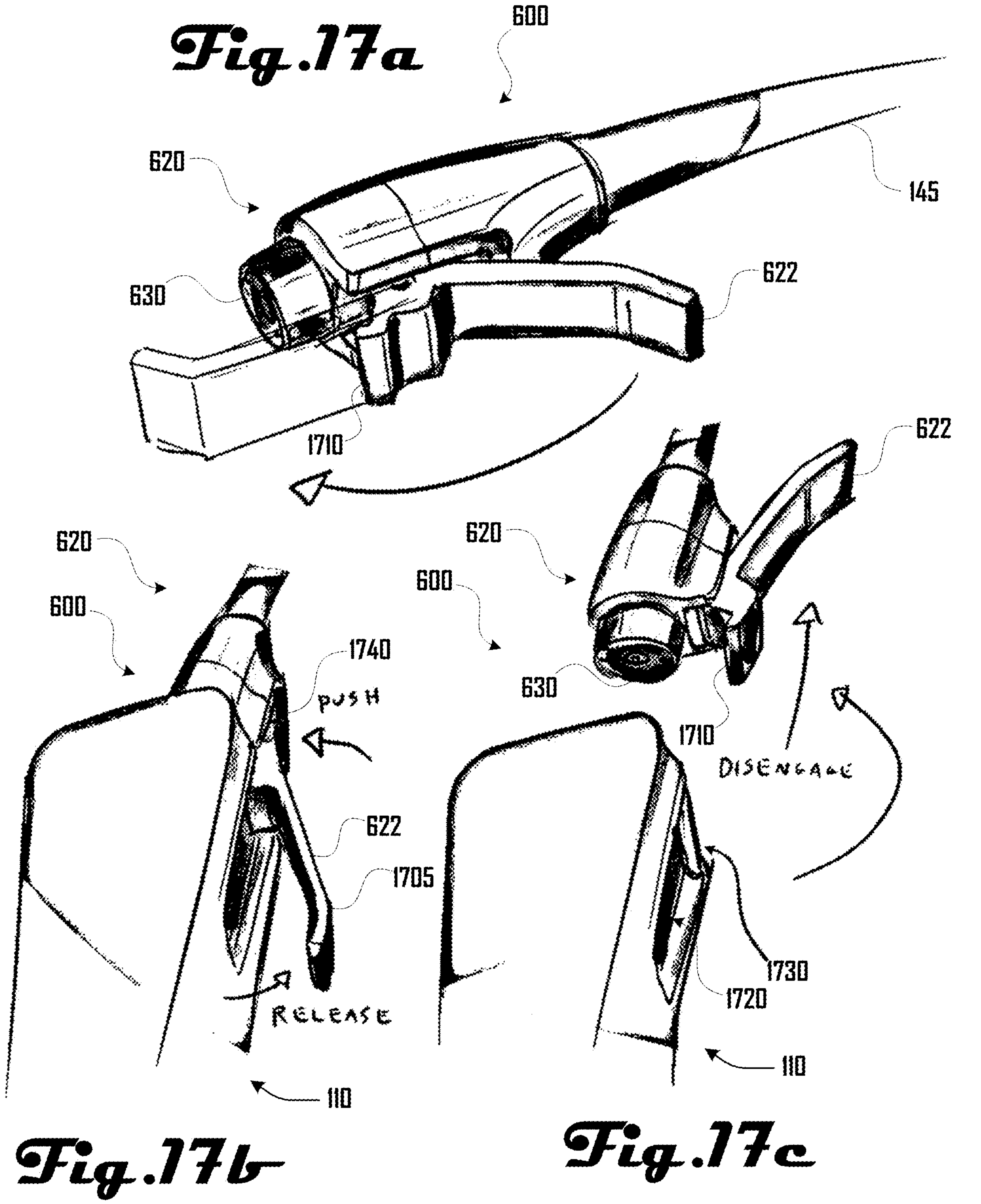
Figures 18A, 18B, 18C:
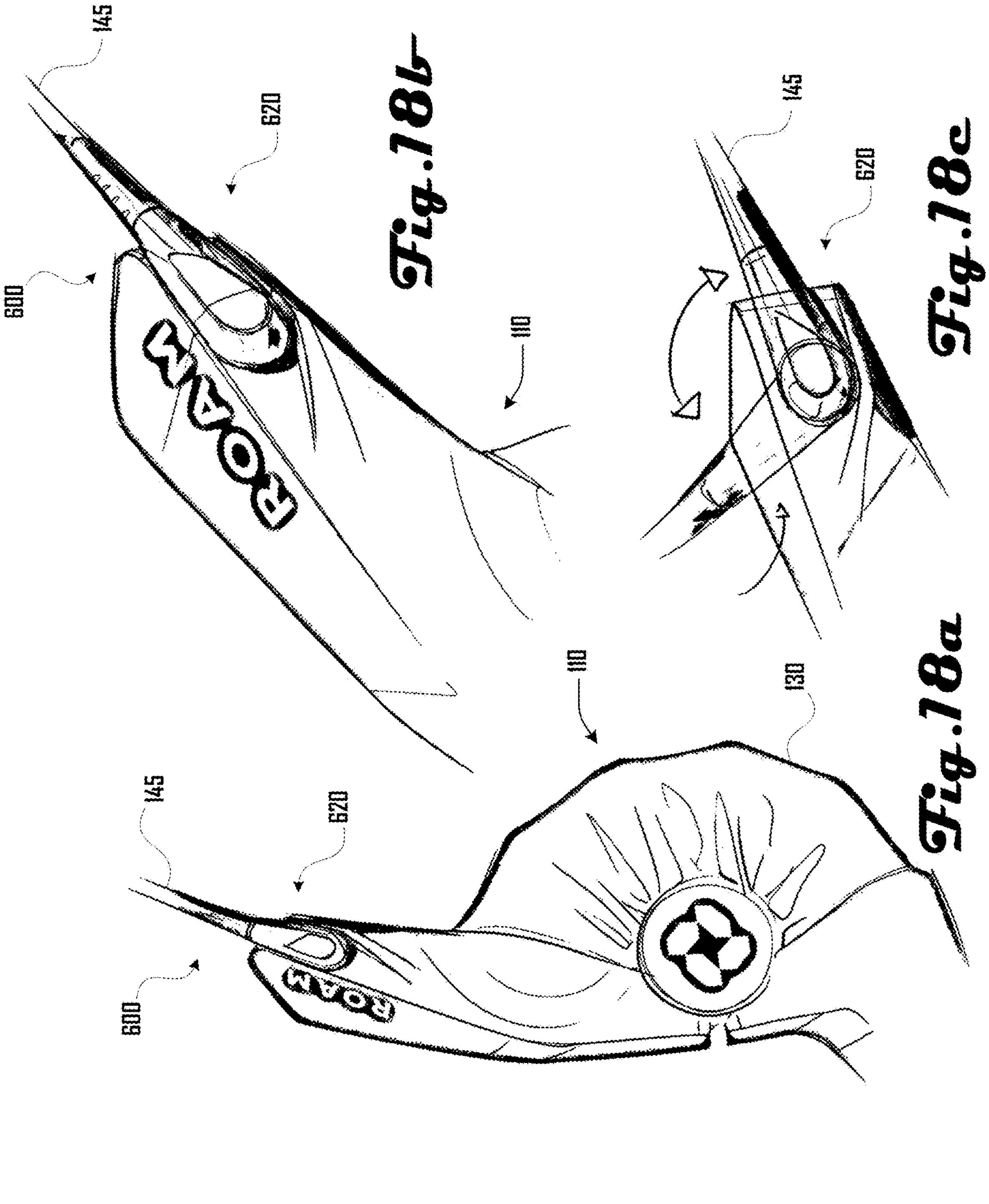
FIGS. 18*a*, 18*b*, 18*c*, 19*a* and 19*b* illustrate an example embodiment of a cable connector that plugs directly into the actuator unit with the first connector side having a rotatable coupling with the actuator unit.

FIGS. 15*a*, 15*b* and 15*c* illustrate another embodiment of a cable connector 600 that plugs directly into the actuator unit 110 and comprises a release button 622 that allows the first connector side 620 to be operably disengaged and/or operably engaged with the first connector side 620 of the cable connector 600 that plugs directly into the actuator unit 110. In this example, a first coupling face 630 of the first connector side 620 can couple with the actuator unit 110, and the release button 622 can be configured to click into place (e.g., via a latch) that can secure the first connector side 620 to the actuator unit 110 as shown in FIG. 15*b*. As shown in FIG. 15*c*, the release button 622 can be pressed to allow for the release of the first connector side 620 from the actuator unit 110. Such a release button 622 can be a snap-hook latch in various embodiments.

FIGS. 16*a*, 16*b*, 17*a*, 17*b* and 17*c* illustrate another embodiment of a cable connector 600 that plugs directly into the actuator unit 110 and comprises a release button 622 that allows the first connector side 620 to be operably disengaged and/or operably engaged with the first connector side 620 of the cable connector 600 that plugs directly into the actuator unit 110. In this example, a first coupling face 630 of the first connector side 620 can couple with the actuator unit 110 and the release button 622 can be configured to rotate via actuation of an arm 1705 such that a flange 1710 of the release button 622 rotates into a slot 1720 of the actuator unit 110 and couples with a lip 1730 to couple the first connector side 620 to the actuator unit 110. To disengage the first connector side 620, a user can press a top portion 1740 and/or pull the arm 1705 to rotate the flange 1710 of the release button 622 out of the slot 1720 and decoupling the flange 1710 from the lip 1730. In various embodiments, such a release button can comprise an over-center latch.

FIGS. 18*a*, 18*b*, 18*c*, 19*a* and 19*b* illustrate an example embodiment of a cable connector 600 that plugs directly into the actuator unit 110 with the first connector side 620 having a rotatable coupling with the actuator unit 110. In some embodiments, electrical contacts of the cable connector 600 can mate with concentric rings, such that a coupling 660 between first and second connector sides 620, 640 can freely rotate without losing connection.

Figure 19A:
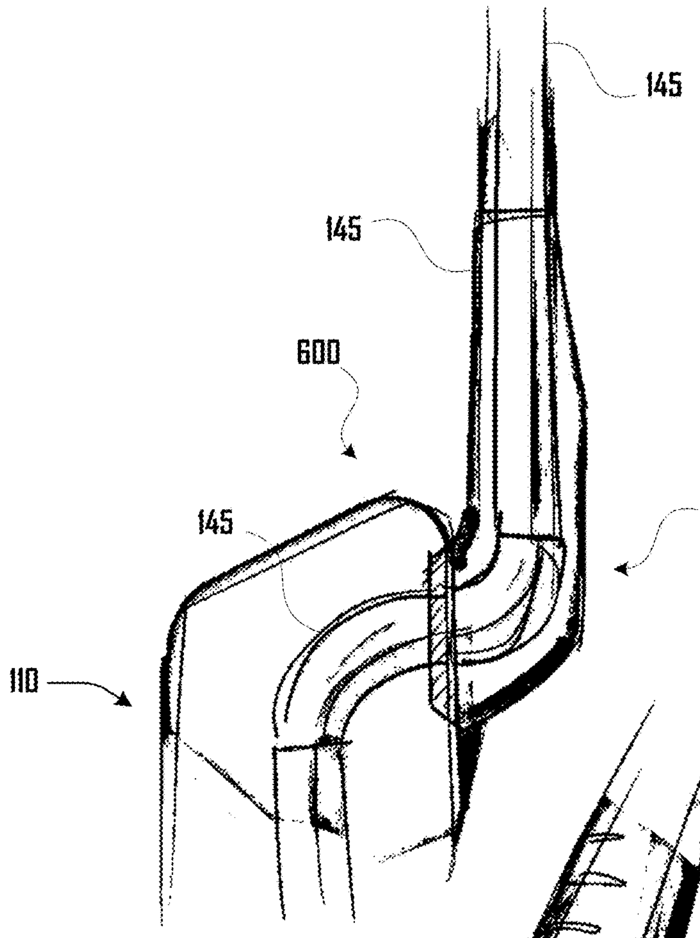

FIG. 19*a* illustrates a see-through view of the first connector side 620 coupled to the actuator unit 110 showing portions of cable 145 extending within the first connector side 620 and the actuator unit 110. In various embodiments, one or more electrical power lines, one or more fluid lines, and/or one or more communication lines can be unified within a cable 145 that extends within at least a portion of the actuator unit 110; however, one or more electrical power lines, one or more fluid lines, and/or one or more communication lines can be separately routed as necessary outside of a unified cable 145 structure to provide fluid to an actuator 130, to provide power to the actuator unit 110, to send or receive communications from the actuator unit 110, and the like.

Figure 19B:
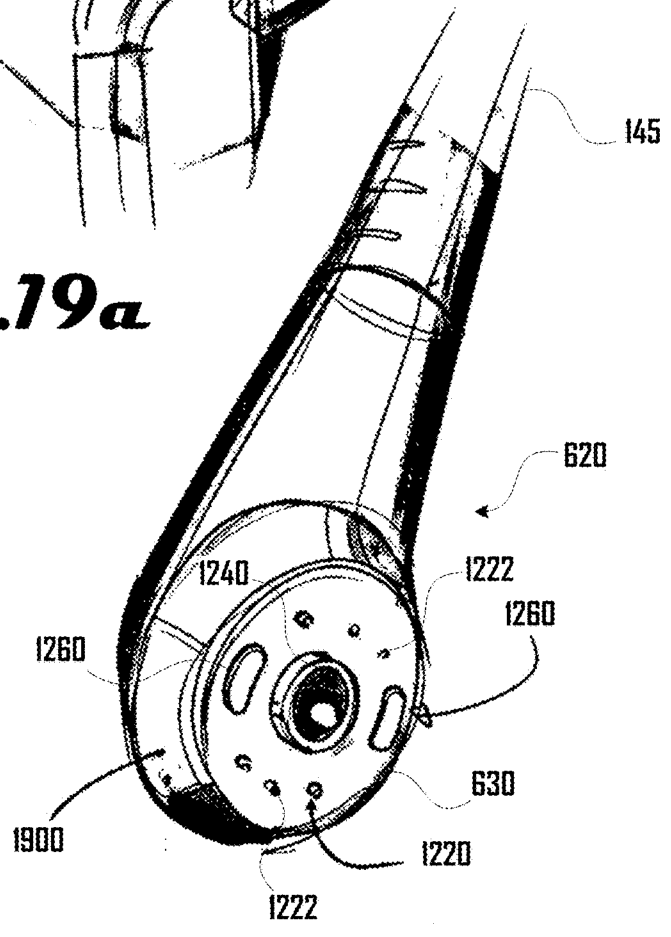

FIG. 19*b* illustrates an example embodiment of a circular first coupling face 630 of the first connector side 620, including a pair of magnets 1260 on opposing sides of a central fluidic connector 1240 with a plurality of pins 1222 (e.g., spring loaded pogo pins) disposed radially from the central fluidic connector 1240. A periphery of the circular first coupling face 630 can comprise registers in a circular detent 1900.

Figure 20B:
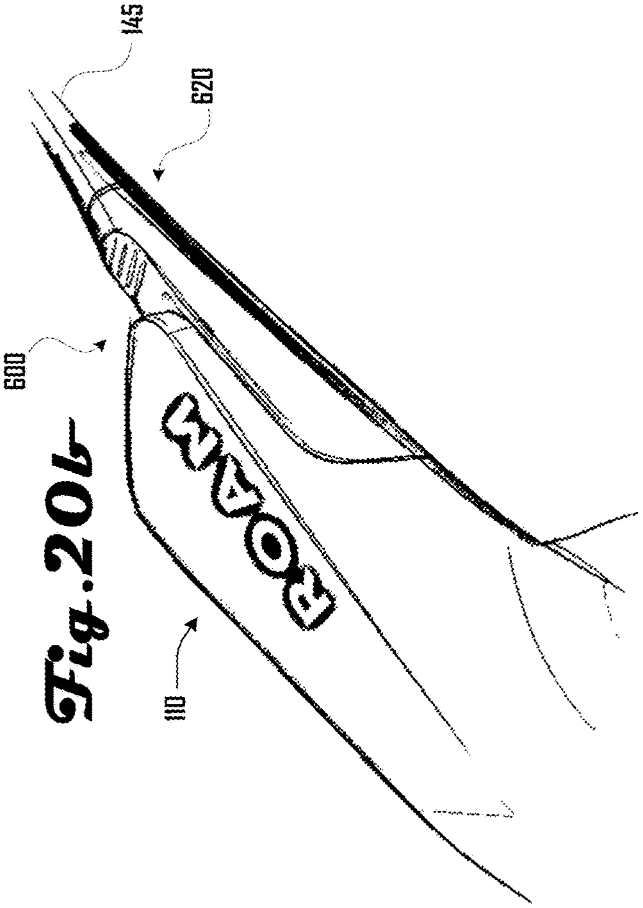
FIGS. 20*a* and 20*b* illustrate another example of a cable connector with a first connector side that plugs directly into an actuator unit.
Figure 20A:
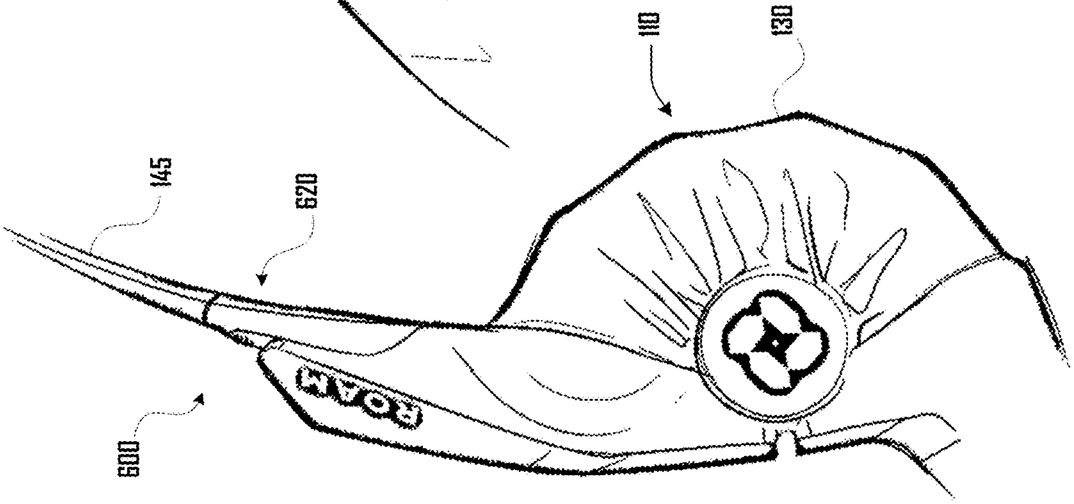

FIGS. 20*a* and 20*b* illustrate another example of a cable connector 600 with a first connector side 620 that plugs directly into an actuator unit 110. FIGS. 21*a*, 21*b* and 21*c* illustrate another example of a cable connector 600 with a first connector side 620 that plugs directly into a second connector side 640 of actuator unit 110. In this example, the first connector side 620 can comprise a pair of coupling arms 2105 that define a coupling slot 2110, which can be configured to couple with a coupling tab 2115 at the second coupling face 650 of the second connector side 640 of the actuator unit 110. In such an embodiment, electrical contacts (e.g., pins 1222) and a fluidic contact 1240 can be located on different faces of the first connector side 620 with the fluidic contact 1240 disposed at an end of a first of the coupling arms 2105 and one or more electrical contacts (e.g., pins 1222) disposed within the coupling slot 2110 such as on one or both of the coupling arms 2105.

There are various features that may be used to help make the cable connector 600 easier to operate for the user in various embodiments. In one embodiment, coupling faces 630, 650 of the cable connector 600 can be asymmetric shapes. Such shapes may be designed to fit in a certain way which will facilitate rotational alignment. In another embodiment, multiple magnets 1260 are placed in specific locations with their poles oriented to assist with alignment. In another embodiment, a grip of one or both of the first and second connector sides 620, 640 may be large and ergonomic, which in some examples can help users with weaker hands. Various other methods may be used to help the user operate the connection.

Figure 22A:
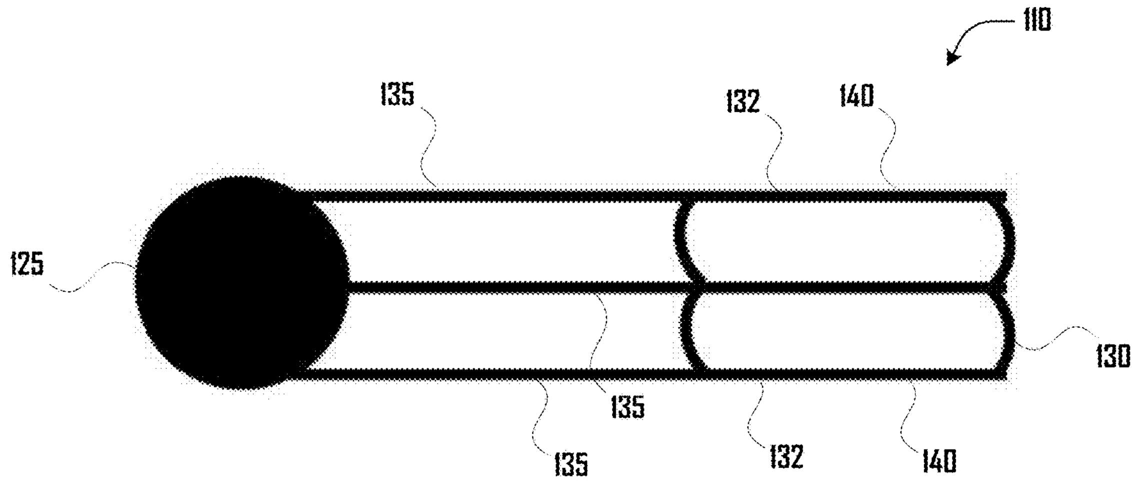
FIG. 22*a* illustrates a side view of a pneumatic actuator in a compressed configuration in accordance with one embodiment.
Figure 22B:
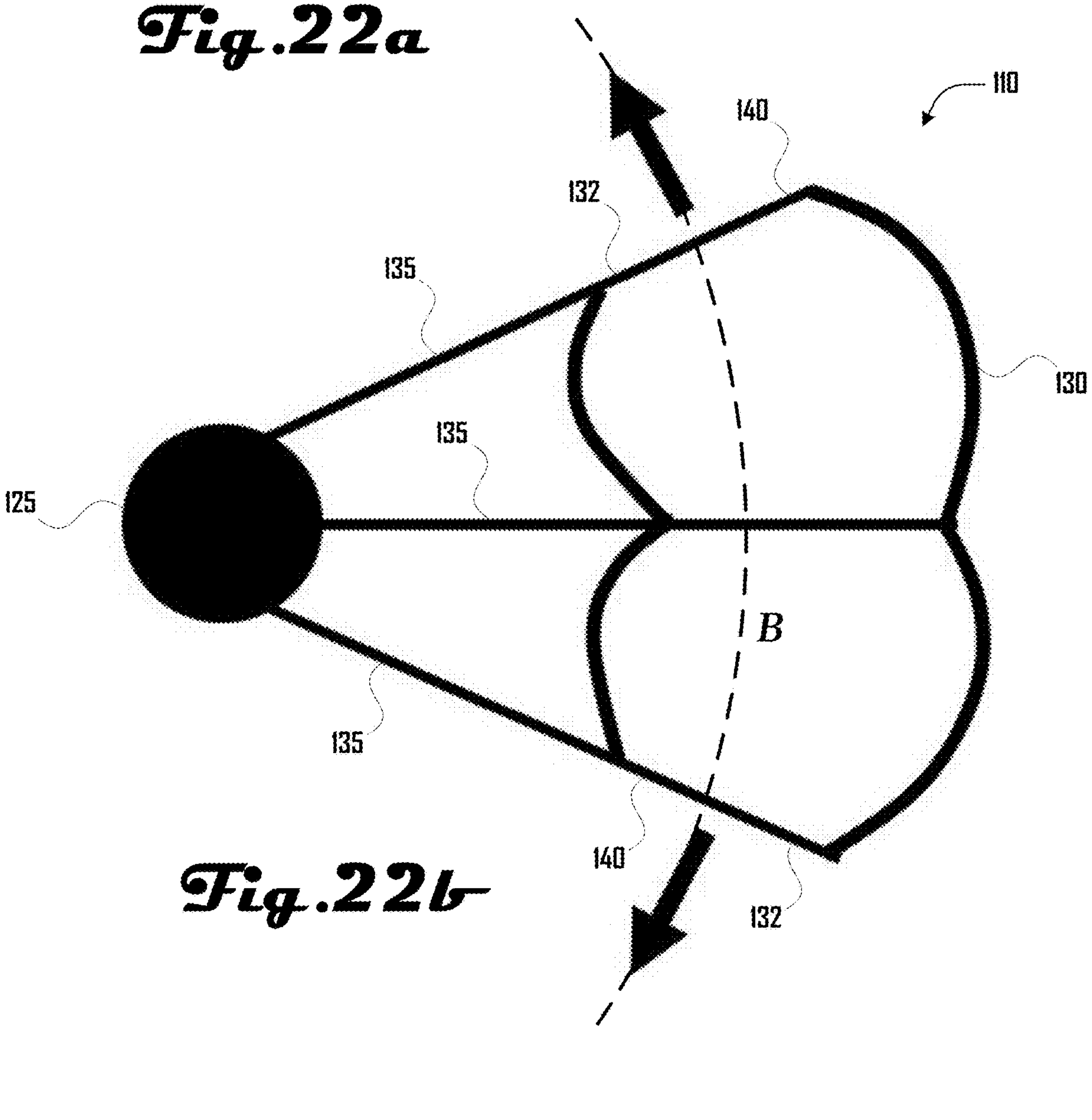
FIG. 22*b* illustrates a side view of the pneumatic actuator of FIG. 22*a* in an expanded configuration.
Figure 23A:
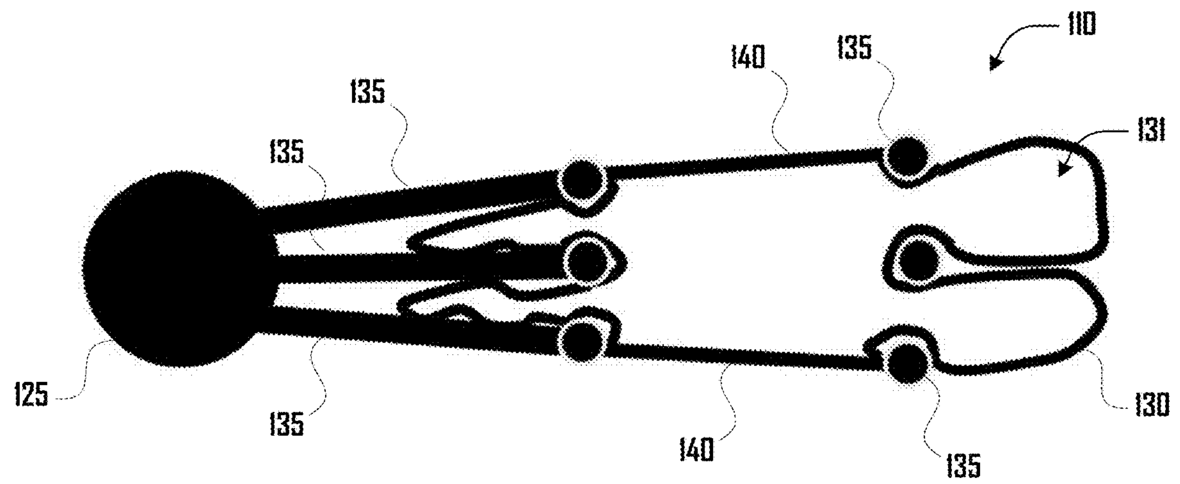
FIG. 23*a* illustrates a cross-sectional side view of a pneumatic actuator in a compressed configuration in accordance with another embodiment.
Figure 23B:
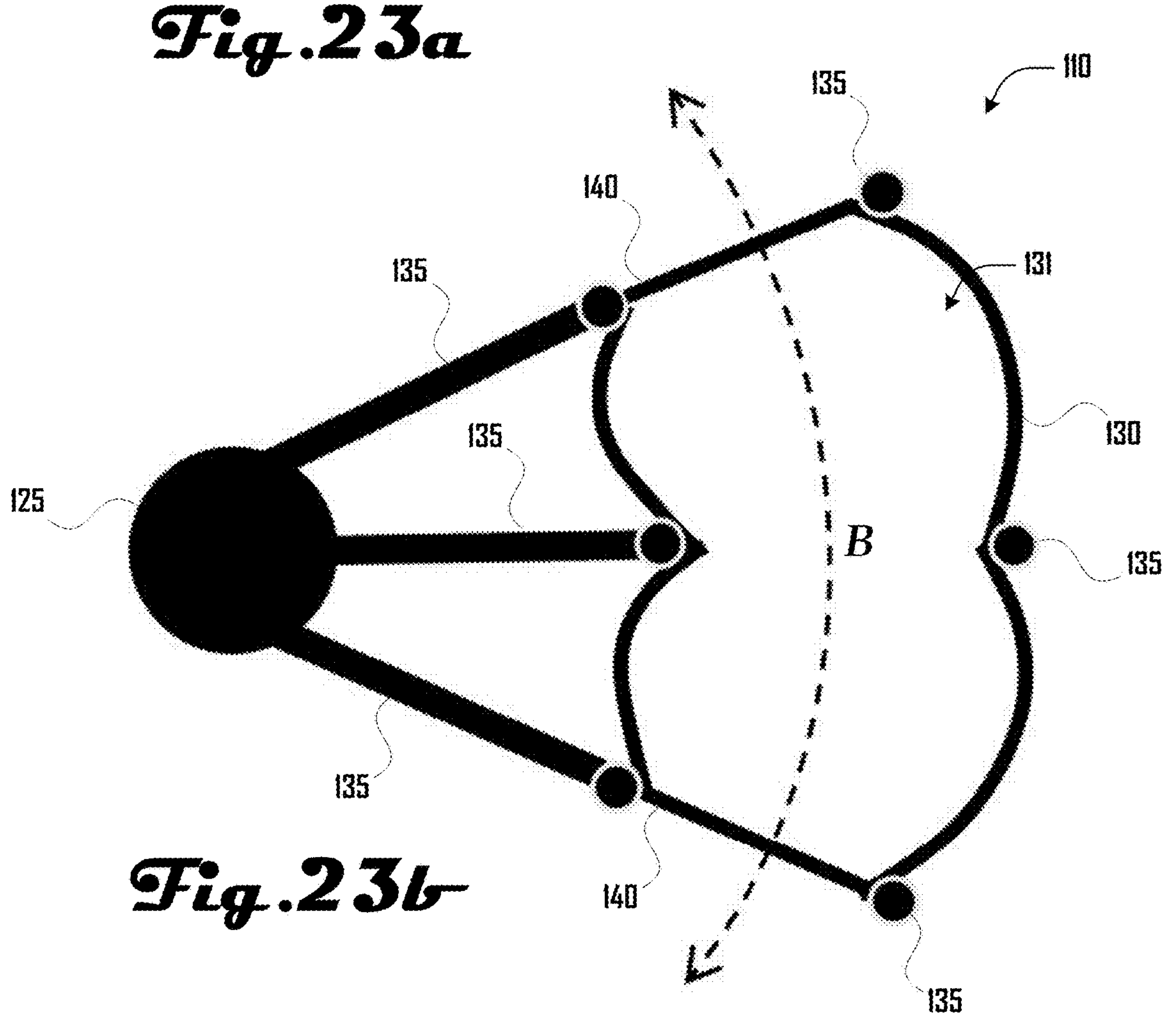
FIG. 23*b* illustrates a cross-sectional side view of the pneumatic actuator of FIG. 23*a* in an expanded configuration.

Turning to FIGS. 22*a*, 22*b*, 23*a* and 23*b*, examples of a leg actuator unit 110 can include the joint 125, bellows actuator 130, constraint ribs 135, and base plates 140. More specifically, FIG. 22*a* illustrates a side view of a leg actuator unit 110 in a compressed configuration and FIG. 22*b* illustrates a side view of the leg actuator unit 110 of FIG. 22*a* in an expanded configuration. FIG. 23*a* illustrates a cross-sectional side view of a leg actuator unit 110 in a compressed configuration and FIG. 23*b* illustrates a cross-sectional side view of the leg actuator unit 110 of FIG. 23*a* in an expanded configuration.

As shown in FIGS. 22*a*, 22*b*, 23*a* and 23*b*, the joint 125 can have a plurality of constraint ribs 135 extending from and coupled to the joint 125, which surround or abut a portion of the bellows actuator 130. For example, in some embodiments, constraint ribs 135 can abut the ends 132 of the bellows actuator 130 and can define some or all of the base plates 140 that the ends 132 of the bellows actuator 130 can push against. However, in some examples, the base plates 140 can be separate and/or different elements than the constraint ribs 135 (e.g., as shown in FIG. 1). Additionally, one or more constraint ribs 135 can be disposed between ends 132 of the bellows actuator 130. For example, FIGS. 22*a*, 22*b*, 23*a* and 23*b* illustrate one constraint rib 135 disposed between ends 132 of the bellows actuator 130; however, further embodiments can include any suitable number of constraint ribs 135 disposed between ends of the bellows actuator 130, including 1, 2, 3, 4, 5, 6, 7, 8, 9, 10, 15, 20, 25, 30, 50, 100 and the like. In some embodiments, constraint ribs can be absent.

As shown in cross sections of FIGS. 23*a* and 23*b*, the bellows actuator 130 can define a cavity 131 that can be filled with fluid (e.g., air), to expand the bellows actuator

130, which can cause the bellows to elongate along axis B as shown in FIGS. 22*b* and 23*b*. For example, increasing a pressure and/or volume of fluid in the bellows actuator 130 shown in FIG. 22*a* can cause the bellows actuator 130 to expand to the configuration shown in FIG. 22*b*. Similarly, increasing a pressure and/or volume of fluid in the bellows actuator 130 shown in FIG. 23*a* can cause the bellows actuator 130 to expand to the configuration shown in FIG. 23*b*. For clarity, the use of the term "bellows" is to describe a component in the described actuator unit 110 and is not intended to limit the geometry of the component. The bellows actuator 130 can be constructed with a variety of geometries including but not limited to a constant cylindrical tube, a cylinder of varying cross-sectional area, a 3-D woven geometry that inflates to a defined arc shape, and the like. The term "bellows" should not be construed to necessarily include a structure having convolutions.

Alternatively, decreasing a pressure and/or volume of fluid in the bellows actuator 130 shown in FIG. 22*b* can cause the bellows actuator 130 to contract to the configuration shown in FIG. 22*a*. Similarly, decreasing a pressure and/or volume of fluid in the bellows actuator 130 shown in FIG. 23*b* can cause the bellows actuator 130 to contract to the configuration shown in FIG. 23*a*. Such increasing or decreasing of a pressure or volume of fluid in the bellows actuator 130 can be performed by pneumatic system 520 and cables 145 of the exoskeleton system 100, which can be controlled by the exoskeleton device 510 (see FIG. 5).

In one preferred embodiment, the bellows actuator 130 can be inflated with air; however, in further embodiments, any suitable fluid can be used to inflate the bellows actuator 130. For example, gasses including oxygen, helium, nitrogen, and/or argon, or the like can be used to inflate and/or deflate the bellows actuator 130. In further embodiments, a liquid such as water, an oil, or the like can be used to inflate the bellows actuator 130. Additionally, while some examples discussed herein relate to introducing and removing fluid from a bellows actuator 130 to change the pressure within the bellows actuator 130, further examples can include heating and/or cooling a fluid to modify a pressure within the bellows actuator 130.

As shown in FIGS. 22*a*, 22*b*, 23*a* and 23*b*, the constraint ribs 135 can support and constrain the bellows actuator 130. For example, inflating the bellows actuator 130 causes the bellows actuator 130 to expand along a length of the bellows actuator 130 and also causes the bellows actuator 130 to expand radially. The constraint ribs 135 can constrain radial expansion of a portion of the bellows actuator 130. Additionally, as discussed herein, the bellows actuator 130 comprises a material that is flexible in one or more directions and the constraint ribs 135 can control the direction of linear expansion of the bellows actuator 130. For example, in some embodiments, without constraint ribs 135 or other constraint structures the bellows actuator 130 would herniate or bend out of axis uncontrollably such that suitable force would not be applied to the base plates 140 such that the arms 115, 120 would not be suitably or controllably actuated. Accordingly, in various embodiments, the constraint ribs 135 can be desirable to generate a consistent and controllable axis of expansion B for the bellows actuator 130 as they are inflated and/or deflated.

In some examples, the bellows actuator 130 in a deflated configuration can substantially extend past a radial edge of the constraint ribs 135 and can retract during inflation to extend less past the radial edge of the constraint ribs 135, to extend to the radial edge of the constraint ribs 135, or not to extend less past the radial edge of the constraint ribs 135. For example, FIG. 23*a* illustrates a compressed configuration of the bellows actuator 130 where the bellows actuator 130 substantially extends past a radial edge of the constraint ribs 135, and FIG. 23*b* illustrates the bellows actuator 130 retracting during inflation to extend less past the radial edge of the constraint ribs 135 in an inflated configuration of the bellows actuator 130.

Figure 24A:
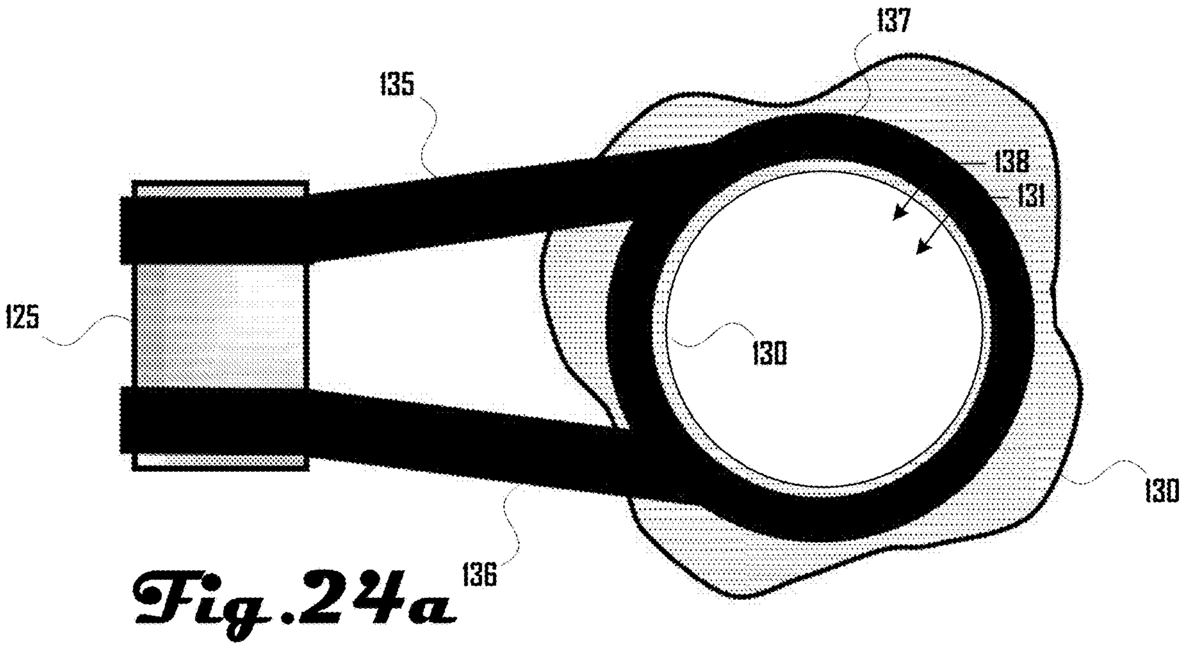
FIG. 24*a* illustrates a top view of a pneumatic actuator in a compressed configuration in accordance with another embodiment.
Figure 24B:
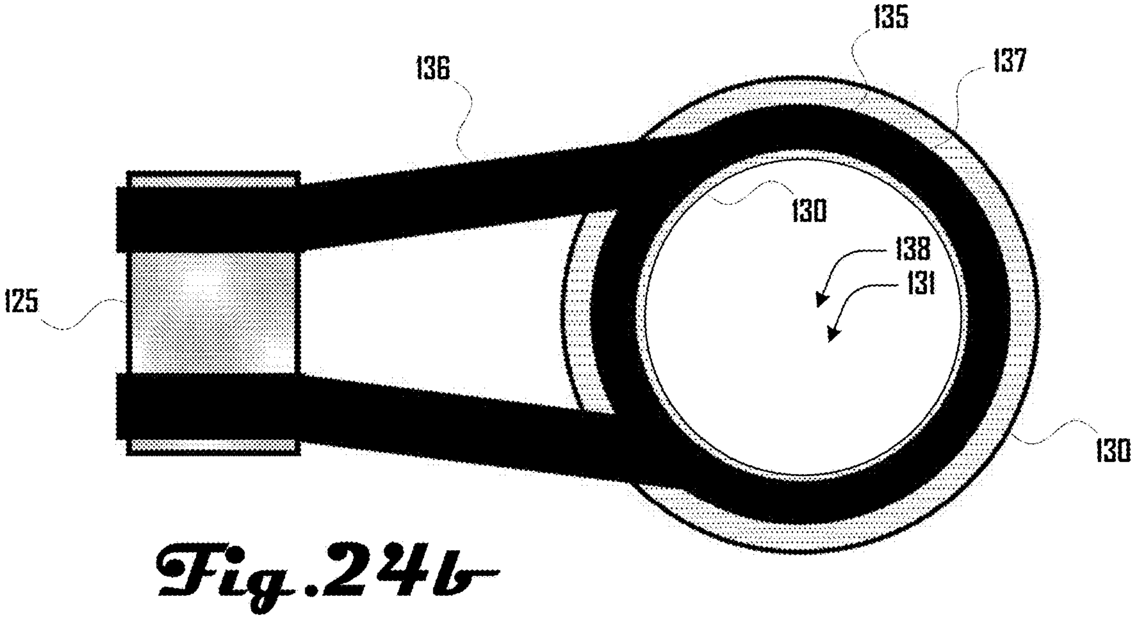
FIG. 24*b* illustrates a top view of the pneumatic actuator of FIG. 24*a* in an expanded configuration.

Similarly, FIG. 24*a* illustrates a top view of a compressed configuration of bellows actuator 130 where the bellows actuator 130 substantially extends past a radial edge of constraint ribs 135, and FIG. 24*b* illustrates a top view where the bellows actuator 130 retracts during inflation to extend less past the radial edge of the constraint ribs 135 in an inflated configuration of the bellows actuator 130.

Figure 25:
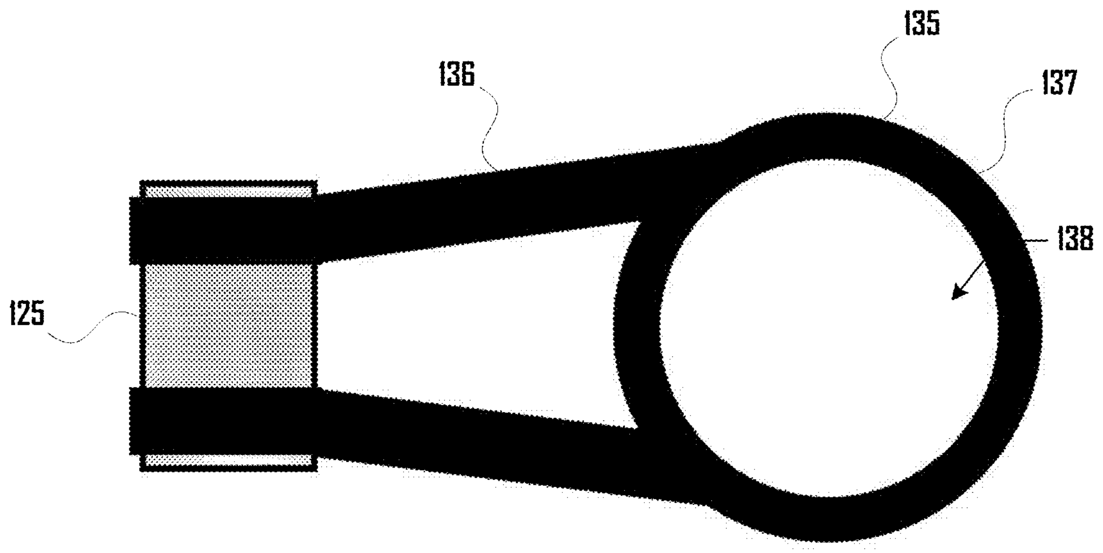
FIG. 25 illustrates a top view of a pneumatic actuator constraint rib in accordance with an embodiment.

Constraint ribs 135 can be configured in various suitable ways. For example, FIGS. 24*a*, 24*b* and 25 illustrate a top view of an example embodiment of a constraint rib 135 having a pair of rib arms 136 that extend from the joint structure 125 and couple with a circular rib ring 137 that defines a rib cavity 138 through which a portion of the bellows actuator 130 can extend (e.g., as shown in FIGS. 23*a*, 23*b*, 24*a* and 24*b*). In various examples, the one or more constraint ribs 135 can be a substantially planar element with the rib arms 136 and rib ring 137 being disposed within a common plane.

In further embodiments, the one or more constraint ribs 135 can have any other suitable configuration. For example, some embodiments can have any suitable number of rib arms 136, including one, two, three, four, five, or the like. Additionally, the rib ring 137 can have various suitable shapes and need not be circular, including one or both of an inner edge that defines the rib cavity 138 or an outer edge of the rib ring 137.

In various embodiments, the constraining ribs 135 can be configured to direct the motion of the bellows actuator 130 through a swept path about some instantaneous center (which may or may not be fixed in space) and/or to prevent motion of the bellows actuator 130 in undesired directions, such as out-of-plane buckling. As a result, the number of constraining ribs 135 included in some embodiments can vary depending on the specific geometry and loading of the leg actuator unit 110. Examples can range from one constraining rib 135 up to any suitable number of constraining ribs 135; accordingly, the number of constraining ribs 135 should not be taken to limit the applicability of the invention. Additionally, constraining ribs 135 can be absent in some embodiments.

The one or more constraining ribs 135 can be constructed in a variety of ways. For example, the one or more constraining ribs 135 can vary in construction on a given leg actuator unit 110, and/or may or may not require attachment to the joint structure 125. In various embodiments, the constraining ribs 135 can be constructed as an integral component of a central rotary joint structure 125. An example embodiment of such a structure can include a mechanical rotary pin joint, where the constraining ribs 135 are connected to and can pivot about the joint 125 at one end of the joint structure 125, and are attached to an inextensible outer layer of the bellows actuator 130 at the other end. In another set of embodiments, the constraining ribs 135 can be constructed in the form of a single flexural structure that directs the motion of the bellows actuator 130 throughout the range of motion for the leg actuator unit 110. Another example embodiment uses a flexural constraining rib 135 that is not connected integrally to the joint structure 125 but is instead attached externally to a previously assembled joint structure 125. Another example embodiment can comprise the constraint ribs 135 being composed of pieces of fabric wrapped around the bellows actuator 130 and attached to the joint structure 125, acting like a hammock to restrict and/or guide the motion of the bellows actuator 130. There are additional methods available for constructing the constraining ribs 135 that can be used in additional embodiments that include but are not limited to a linkage, a rotational flexure connected around the joint structure 125, and the like.

In some examples, a design consideration for constraining ribs 135 can be how the one or more constraining ribs 135 interact with the bellows actuator 130 to guide the path of the bellows actuator 130. In various embodiments, the constraining ribs 135 can be fixed to the bellows actuator 130 at predefined locations along the length of the bellows actuator 130. One or more constraining ribs 135 can be coupled to the bellows actuator 130 in various suitable ways, including but not limited to sewing, mechanical clamps, geometric interference, direct integration, and the like. In other embodiments, the constraining ribs 135 can be configured such that the constraining ribs 135 float along the length of the bellows actuator 130 and are not fixed to the bellows actuator 130 at predetermined connection points. In some embodiments, the constraining ribs 135 can be configured to restrict a cross sectional area of the bellows actuator 130. An example embodiment can include a tubular bellows actuator 130 attached to a constraining rib 135 that has an oval cross section, which in some examples can be a configuration to reduce the width of the bellows actuator 130 at that location when the bellows actuator 130 is inflated.

The bellows actuator 130 can have various functions in some embodiments, including containing operating fluid of the leg actuator unit 110, resisting forces associated with operating pressure of the leg actuator unit 110, and the like. In various examples, the leg actuator unit 110 can operate at a fluid pressure above, below or at about ambient pressure. In various embodiments, the bellows actuator 130 can comprise one or more flexible yet inextensible or practically inextensible materials in order to resist expansion (e.g., beyond what is desired in directions other than an intended direction of force application or motion) of the bellows actuator 130 beyond what is desired when pressurized above ambient pressure. Additionally, the bellows actuator 130 can comprise an impermeable or semi-impermeable material in order to contain the actuator fluid.

Figure 27:
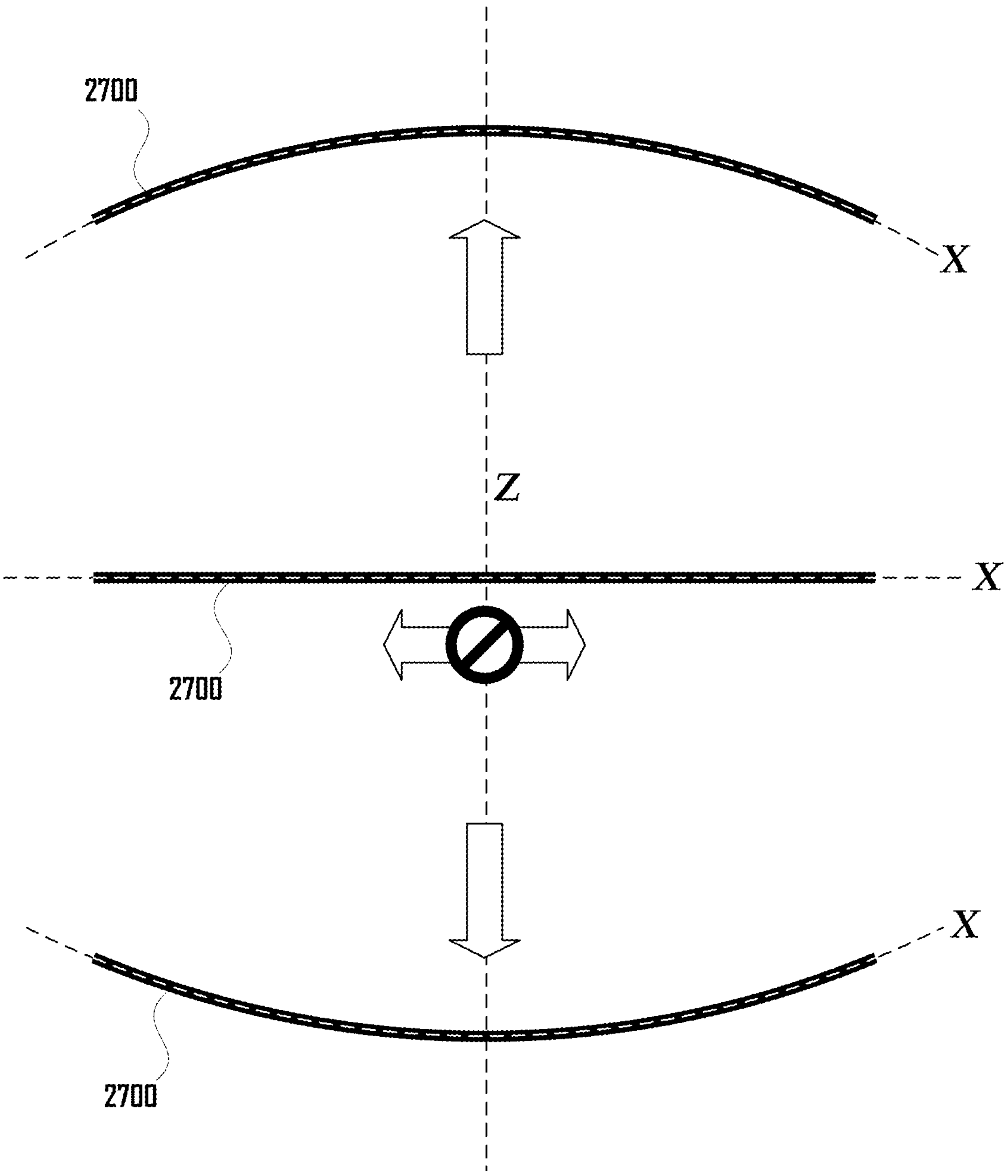
FIG. 27 illustrates an example planar material that is substantially inextensible along one or more plane axes of the planar material while being flexible in other directions.

For example, in some embodiments, the bellows actuator 130 can comprise a flexible sheet material such as woven nylon, rubber, polychloroprene, a plastic, latex, a fabric, or the like. Accordingly, in some embodiments, the bellows actuator 130 can be made of a planar material that is substantially inextensible along one or more plane axes of the planar material while being flexible in other directions. For example, FIG. 27 illustrates a side view of a planar material 2700 (e.g., a fabric) that is substantially inextensible along axis X that is coincident with the plane of the material 2700, yet flexible in other directions, including axis Z. In the example of FIG. 27, the material 2700 is shown flexing upward and downward along axis Z while being inextensible along axis X. In various embodiments, the material 2700 can also be inextensible along an axis Y (not shown) that is also coincident with the plane of the material 2700 like axis X and perpendicular to axis X.

In some embodiments, the bellows actuator 130 can be made of a non-planar woven material that is inextensible along one or more axes of the material. For example, in one embodiment the bellows actuator 130 can comprise a woven fabric tube. Woven fabric material can provide inextensibility along the length of the bellows actuator 130 and in the circumferential direction. Such embodiments can still be able to be configured along the body of the user 101 to align with the axis of a desired joint on the body 101 (e.g., the knee 103).

In various embodiments, the bellows actuator 130 can develop its resulting force by using a constrained internal surface length and/or external surface length that are a constrained a distance away from each other (e.g., due to an inextensible material as discussed above). In some examples, such a design can allow the bellows actuator 130 to contract, but when pressurized to a certain threshold, the bellows actuator 130 can direct the forces axially by pressing on the plates 140 of the leg actuator unit 110 because there is no ability for the bellows actuator 130 to expand further in volume otherwise due to being unable to extend its length past a maximum length defined by the body of the bellows actuator 130.

In other words, the bellows actuator 130 can comprise a substantially inextensible textile envelope that defines a chamber that is made fluid-impermeable by a fluid-impermeable bladder contained in the substantially inextensible textile envelope and/or a fluid-impermeable structure incorporated into the substantially inextensible textile envelope. The substantially inextensible textile envelope can have a predetermined geometry and a non-linear equilibrium state at a displacement that provides a mechanical stop upon pressurization of the chamber to prevent excessive displacement of the substantially inextensible textile actuator.

In some embodiments, the bellows actuator 130 can include an envelope that consists or consists essentially of inextensible textiles (e.g., inextensible knits, woven, nonwoven, etc.) that can prescribe various suitable movements as discussed herein. Inextensible textile bellows actuator 130 can be designed with specific equilibrium states (e.g., end states or shapes where they are stable despite increasing pressure), pressure/stiffness ratios, and motion paths. Inextensible textile bellows actuator 130 in some examples can be configured accurately delivering high forces because inextensible materials can allow greater control over directionality of the forces.

Accordingly, some embodiments of inextensible textile bellows actuator 130 can have a pre-determined geometry that produces displacement mostly via a change in the geometry between the uninflated shape and the pre-determined geometry of its equilibrium state (e.g., fully inflated shape) due to displacement of the textile envelope rather than via stretching of the textile envelope during a relative increase in pressure inside the chamber; in various embodiments, this can be achieved by using inextensible materials in the construction of the envelope of the bellows actuator 130. As discussed herein, in some examples "inextensible" or "substantially inextensible" can be defined as expansion by no more than 10%, no more than 5%, or no more than 1% in one or more direction.

Figure 26A:
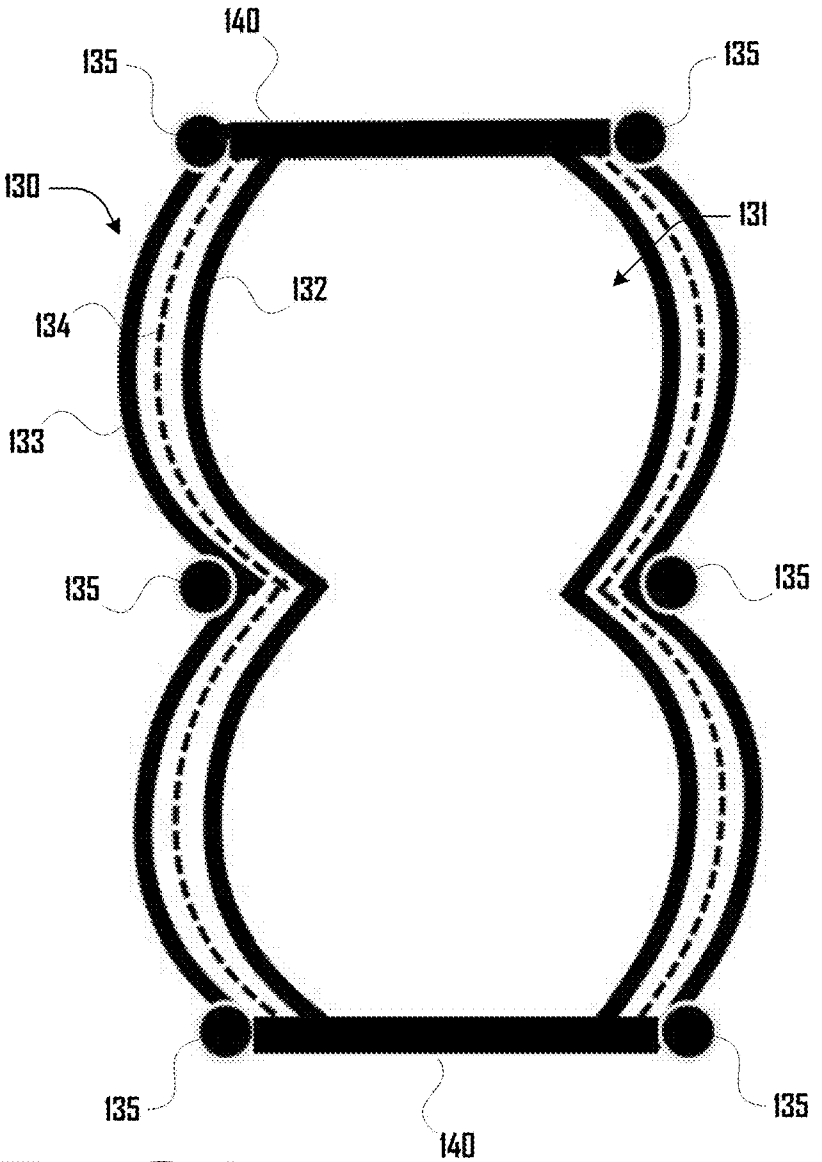
FIG. 26*a* illustrates a cross-sectional view of a pneumatic actuator bellows in accordance with another embodiment.
Figure 26B:
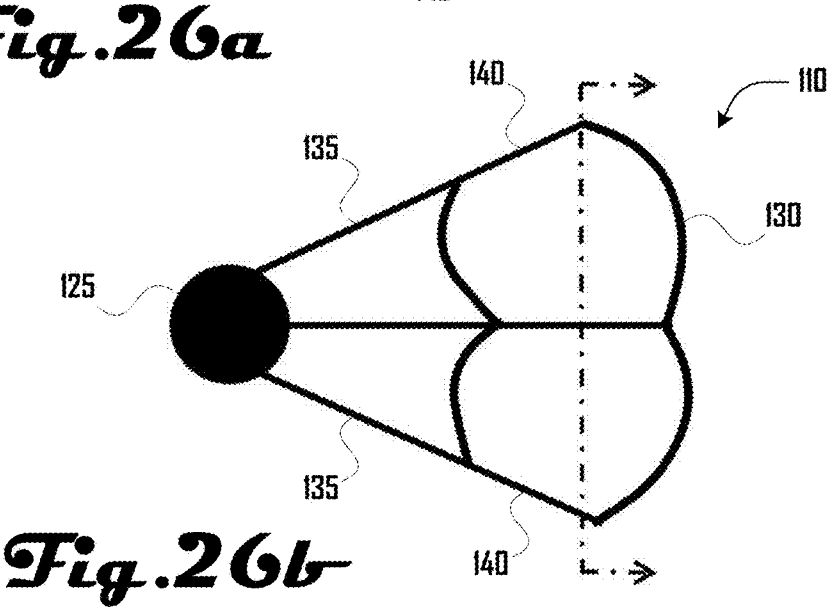
FIG. 26*b* illustrates a side view of the pneumatic actuator of FIG. 26*a* in an expanded configuration showing the cross section of FIG. 26*a*.

FIG. 26*a* illustrates a cross-sectional view of a pneumatic actuator unit 110 including bellows actuator 130 in accordance with another embodiment, and FIG. 26*b* illustrates a side view of the pneumatic actuator unit 110 of FIG. 26*a* in an expanded configuration showing the cross section of FIG. 26*a*. As shown in FIG. 26*a*, the bellows actuator 130 can comprise an internal first layer 132 that defines the bellows cavity 131 and can comprise an outer second layer 133 with a third layer 134 disposed between the first and second layers 132, 133. Throughout this description, the use of the term "layer" to describe the construction of the bellows actuator 130 should not be viewed as limiting to the design. The use of 'layer' can refer to a variety of designs including a planar material sheet, a wet film, a dry film, a rubberized coating, a co-molded structure, and the like.

In some examples, the internal first layer 132 can comprise a material that is impermeable or semi-permeable to the actuator fluid (e.g., air), and the external second layer 133 can comprise an inextensible material as discussed herein. For example, as discussed herein, an impermeable layer can refer to an impermeable or semi-permeable layer, and an inextensible layer can refer to an inextensible or a practically inextensible layer.

In some embodiments comprising two or more layers, the internal layer 132 can be slightly oversized compared to an inextensible outer second layer 133 such that the internal forces can be transferred to the high-strength inextensible outer second layer 133. One embodiment comprises a bellows actuator 130 with an impermeable polyurethane polymer film inner first layer 132 and a woven nylon braid as the outer second layer 133.

The bellows actuator 130 can be constructed in various suitable ways in further embodiments, which can include a single-layer design that is constructed of a material that provides both fluid impermeability and that is sufficiently inextensible. Other examples can include a complex bellows assembly that comprises multiple laminated layers that are fixed together into a single structure. In some examples, it can be necessary to limit the deflated stack height of the bellows actuator 130 to maximize the range of motion of the leg actuator unit 110. In such an example, it can be desirable to select a low-thickness fabric that meets the other performance needs of the bellows actuator 130.

In yet another embodiment, it can be desirable to reduce friction between the various layers of the bellows actuator 130. In one embodiment, this can include the integration of a third layer 134 that acts as an anti-abrasive and/or low friction intermediate layer between the first and second layers 132, 133. Other embodiments can reduce the friction between the first and second layers 132, 133 in alternative or additional ways, including but not limited to the use of a wet lubricant, a dry lubricant, or multiple layers of low friction material. Accordingly, while the example of FIG. 24*a* illustrates an example of a bellows actuator 130 comprising three layers 132, 133, 134, further embodiments can include a bellows actuator 130 having any suitable number of layers, including one, two, three, four, five, ten, fifteen, twenty-five, and the like. Such one or more layers can be coupled along adjoining faces in part or in whole, with some examples defining one or more cavities between layers. In such examples, material such as lubricants or other suitable fluids can be disposed in such cavities, or such cavities can be effectively empty. Additionally, as described herein, one or more layers (e.g., the third layer 134) need not be a sheet or planar material layer as shown in some examples and can instead comprise a layer defined by a fluid. For example, in some embodiments, the third layer 134 can be defined by a wet lubricant, a dry lubricant, or the like.

The inflated shape of the bellows actuator 130 can be important to the operation of the bellows actuator 130 and/or leg actuator unit 110 in some embodiments. For example, the inflated shape of the bellows actuator 130 can be affected through the design of both an impermeable and inextensible portion of the bellows actuator 130 (e.g., the first and second layer 132, 133). In various embodiments, it can be desirable to construct one or more of the layers 132, 133, 134 of the bellows actuator 130 out of various two-dimensional panels that may not be intuitive in a deflated configuration.

In some embodiments, one or more impermeable layers can be disposed within the bellows cavity 131, and/or the bellows actuator 130 can comprise a material that is capable of holding a desired fluid (e.g., a fluid impermeable first internal layer 132 as discussed herein). The bellows actuator 130 can comprise a flexible, elastic, or deformable material that is operable to expand and contract when the bellows actuators 130 are inflated or deflated as described herein. In some embodiments, the bellows actuator 130 can be biased toward a deflated configuration such that the bellows actuator 130 is elastic and tends to return to the deflated configuration when not inflated. Additionally, although bellows actuator 130 shown herein are configured to expand and/or extend when inflated with fluid, in some embodiments, bellows actuator 130 can be configured to shorten and/or retract when inflated with fluid in some examples. Also, the term "bellows" as used herein should not be construed to be limiting in any way. For example, the term "bellows" as used herein should not be construed to require elements such as convolutions or other such features (although convoluted bellows actuator 130 can be present in some embodiments). As discussed herein, bellows actuator 130 can take on various suitable shapes, sizes, proportions and the like.

The bellows actuator 130 can vary significantly across various embodiments, so the present examples should not be construed to be limiting. One preferred embodiment of a bellows actuator 130 includes fabric-based pneumatic actuator configured such that it provides knee extension torque as discussed herein. Variants of this embodiment can exist to tailor the actuator to provide the desired performance characteristics of the actuators such as a fabric actuator that is not of a uniform cross-section. Other embodiments can use an electro-mechanical actuator configured to provide flexion and extension torques at the knee instead of or in addition to a fluidic bellows actuator 130. Various embodiments can include but are not limited to designs that incorporate combinations of electromechanical, hydraulic, pneumatic, electro-magnetic, or electro-static for positive power or negative power assistance of extension or flexion of a lower extremity joint.

The bellows actuator 130 can also be located in a variety of locations as required by the specific design. One embodiment places the bellows actuator 130 of a powered knee brace component located in line with the axis of the knee joint and positioned parallel to the joint itself. Various embodiments include but are not limited to actuators configured in series with the joint, actuators configured anterior to the joint, and actuators configured to rest around the joint.

Various embodiments of the bellows actuator 130 can include secondary features that augment the operation of the actuation. One such embodiment is the inclusion of user-adjustable mechanical hard end stops to limit the allowable range of motion to the bellows actuator 130. Various embodiments can include but are not limited to the following extension features: the inclusion of flexible end stops, the inclusion of an electromechanical brake, the inclusion of an electro-magnetic brake, the inclusion of a magnetic brake, the inclusion of a mechanical disengage switch to mechanically decouple the joint from the actuator, or the inclusion of a quick release to allow for quick changing of actuator components.

In various embodiments, the bellows actuator 130 can comprise a bellows and/or bellows system as described in related U.S. patent application Ser. No. 14/064,071 filed Oct. 25, 2013, which issued as U.S. Pat. No. 9,821,475; as described in U.S. patent application Ser. No. 14/064,072 filed Oct. 25, 2013; as described in U.S. patent application Ser. No. 15/823,523 filed Nov. 27, 2017; or as described in U.S. patent application Ser. No. 15/472,740 filed Mar. 29, 2017.

In some applications, the design of the fluidic actuator unit 110 can be adjusted to expand its capabilities. One example of such a modification can be made to tailor the torque profile of a rotary configuration of the fluidic actuator unit 110 such that the torque changes as a function of the angle of the joint structure 125. To accomplish this in some examples, the cross-section of the bellows actuator 130 can be manipulated to enforce a desired torque profile of the overall fluidic actuator unit 110. In one embodiment, the diameter of the bellows actuator 130 can be reduced at a longitudinal center of the bellows actuator 130 to reduce the overall force capabilities at the full extension of the bellows actuator 130. In yet another embodiment, the cross-sectional areas of the bellows actuator 130 can be modified to induce a desired buckling behavior such that the bellows actuator 130 does not get into an undesirable configuration. In an example embodiment, the end configurations of the bellows actuator 130 of a rotary configuration can have the area of the ends reduced slightly from the nominal diameter to provide for the end portions of the bellows actuator 130 to buckle under loading until the actuator unit 110 extends beyond a predetermined joint angle, at which point the smaller diameter end portion of the bellows actuator 130 would begin to inflate.

In other embodiments, this same capability can be developed by modifying the behavior of the constraining ribs 135. As an example embodiment, using the same example bellows actuator 130 as discussed in the previous embodiment, two constraining ribs 135 can fixed to such bellows actuator 130 at evenly distributed locations along the length of the bellows actuator 130. In some examples, a goal of resisting a partially inflated buckling can be combated by allowing the bellows actuator 130 to close in a controlled manner as the actuator unit 110 closes. The constraining ribs 135 can be allowed to get closer to the joint structure 125 but not closer to each other until they have bottomed out against the joint structure 125. This can allow the center portion of the bellows actuator 130 to remain in a fully inflated state which can be the strongest configuration of the bellows actuator 130 in some examples.

In further embodiments, it can be desirable to optimize the fiber angle of the individual braid or weave of the bellows actuator 130 in order to tailor specific performance characteristics of the bellows actuator 130 (e.g., in an example where a bellows actuator 130 includes inextensibility provided by a braided or woven fabric). In other embodiments, the geometry of the bellows actuator 130 of the actuator unit 110 can be manipulated to allow the robotic exoskeleton system 100 to operate with different characteristics. Example methods for such modification can include but are not limited to the following: the use of smart materials on the bellows actuator 130 to manipulate the mechanical behavior of the bellows actuator 130 on command; or the mechanical modification of the geometry of the bellows actuator 130 through means such as shortening the operating length and/or reducing the cross-sectional area of the bellows actuator 130.

In further examples, a fluidic actuator unit 110 can comprise a single bellows actuator 130 or a combination of multiple bellows actuator 130, each with its own composition, structure, and geometry. For example, some embodiments can include multiple bellows actuator 130 disposed in parallel or concentrically on the same joint assembly 125 that can be engaged as needed. In one example embodiment, a joint assembly 125 can be configured to have two bellows actuator 130 disposed in parallel directly next to each other. The exoskeleton system 100 can selectively choose to engage each bellows actuator 130 as needed to allow for various amounts of force to be output by the same fluidic actuator unit 110 in a desirable mechanical configuration.

In further embodiments, a fluidic actuator unit 110 can include various suitable sensors to measure mechanical properties of the bellows actuator 130 or other portions of the fluidic actuator unit 110 that can be used to directly or indirectly estimate pressure, force, or strain in the bellows actuator 130 or other portions of the fluidic actuator unit 110. In some examples, sensors located at the fluidic actuator unit 110 can be desirable due to the difficulty in some embodiments associated with the integration of certain sensors into a desirable mechanical configuration while others may be more suitable. Such sensors at the fluidic actuator unit 110 can be operably connected to the exoskeleton device 1210 (see FIG. 12) and the exoskeleton device 1210 can use data from such sensors at the fluidic actuator unit 110 to control the exoskeleton system 100.

As discussed herein, various suitable exoskeleton systems 100 can be used in various suitable ways and for various suitable applications. However, such examples should not be construed to be limiting on the wide variety of exoskeleton systems 100 or portions thereof that are within the scope and spirit of the present disclosure. Accordingly, exoskeleton systems 100 that are more or less complex than the examples of FIGS. 1-5 are within the scope of the present disclosure.

Additionally, while various examples relate to an exoskeleton system 100 associated with the legs or lower body of a user, further examples can be related to any suitable portion of a user body including the torso, arms, head, legs, or the like. Also, while various examples relate to exoskeletons, it should be clear that the present disclosure can be applied to other similar types of technology, including prosthetics, body implants, robots, or the like. Further, while some examples can relate to human users, other examples can relate to animal users, robot users, various forms of machinery, or the like.

The described embodiments are susceptible to various modifications and alternative forms, and specific examples thereof have been shown by way of example in the drawings and are herein described in detail. It should be understood, however, that the described embodiments are not to be limited to the particular forms or methods disclosed, but to the contrary, the present disclosure is to cover all modifications, equivalents, and alternatives. Additionally, elements of a given embodiment should not be construed to be applicable to only that example embodiment and therefore elements of one example embodiment can be applicable to other embodiments. Additionally, elements that are specifically shown in example embodiments should be construed to cover embodiments that comprise, consist essentially of, or consist of such elements, or such elements can be explicitly absent from further embodiments. Accordingly, the recitation of an element being present in one example should be construed to support some embodiments where such an element is explicitly absent.

What is claimed is:

1. An exoskeleton system comprising:

a left and right leg actuator unit configured to be respectively coupled to a left and right leg of a user, the left and right leg actuator units each including:

an upper arm and a lower arm that are rotatably coupled via a joint, the joint adapted to a knee of the user with the upper arm adapted to an upper leg portion of the user above the knee and with the lower arm adapted to a lower leg portion of the user below the knee, and a fluidic bellows actuator that extends between the upper arm and lower arm; and an exoskeleton device that includes:

a fluidic system, and a processor and memory, the memory storing instructions, that when executed by the processor, are configured to control the fluidic system to introduce fluid to the bellows actuators of the left and right leg actuator units; and a plurality of unitary cables, comprising a first unitary cable extending from the exoskeleton device to the right leg actuator unit and a second unitary cable extending from the exoskeleton device to the left leg actuator unit, the first and second unitary cables each comprising:

one or more electrical power lines configured to convey electrical power from the exoskeleton device to the left or right leg actuator unit, one or more fluid lines configured to convey the fluid from the exoskeleton device to the respective bellows actuators of the left or right leg actuator unit, one or more communication lines configured to convey communication signals from the exoskeleton device to the left or right leg actuator unit, a sheath that surrounds and encloses the one or more electrical power lines, the one or more fluid lines, and the one or more communication lines, and a cable connector comprising:

a first connector side having a release button and a first coupling face that includes a first pin array and a fluidic connector surrounded by a first cylindrical magnet, a second connector side having a second coupling face that includes a second pin array configured to operably couple and de-couple with the first pin array, a fluid stem surrounded by a second cylindrical magnet, the fluid stem configured to operably couple and de-couple with the fluidic connector of the first connector side, the second cylindrical magnet configured to couple and de-couple with the first cylindrical magnet of the first connector side, and a first and a second cable portion extending respectively from the first and second connector sides, wherein actuating the release button causes the first and second coupling faces to disengage, including causing the first and second cylindrical magnets to decouple, causing the first and second pin arrays to de-couple, and causing the fluid stem and fluidic connector to de-couple.

2. The exoskeleton system of claim 1, wherein the fluid comprises air and wherein the one or more fluid lines comprise one or more tubes configured to convey the air from an air source at the exoskeleton device to the respective bellows actuators of the left or right leg actuator units to cause selective inflation of the respective bellows actuators of the left or right leg actuator units.

3. The exoskeleton system of claim 1, wherein the first and second cable portions consist essentially of:

a single fluid line defined by a tube configured to convey air from an air source at the exoskeleton device;

a single power line configured to convey the electrical power; and a plurality of communication lines, including at least five communication lines.

4. The exoskeleton system of claim 1, wherein the cable connectors are configured for a safety disconnect function that allows the cable connectors to disengage when the cable connectors experience a sufficient pulling force to cause, without the actuation of the release button, the first and second coupling faces to disengage, including causing the first and second cylindrical magnets to decouple, causing the first and second pin arrays to de-couple, and causing the fluid stem and the fluidic connector to de-couple.

5. An exoskeleton system comprising:

one or more actuator units that comprise one or more fluidic actuators;

an exoskeleton device that includes:

a fluidic system, and a device configured to control the fluidic system to introduce fluid to the one or more fluidic actuators of the one or more actuator units; and one or more unitary cables, comprising at least a first unitary cable extending from the exoskeleton device to a first actuator unit, the first unitary cable comprising:

one or more electrical power lines configured to convey electrical power from the exoskeleton device to the first actuator unit, one or more fluid lines configured to convey the fluid from the exoskeleton device to a first fluidic actuator of the first actuator unit, one or more communication lines configured to convey communication signals from the exoskeleton device to the first actuator unit, and a cable connector comprising:

a first connector side having a first coupling face that includes a first pin array, a fluidic connector, and a first magnet, and a second connector side having a second coupling face that includes a second pin array configured to operably couple and de-couple with the first pin array, a fluid stem configured to operably couple and de-couple with the fluidic connector of the first connector side, and a second magnet configured to couple and de-couple with the first magnet of the first connector side.

6. The exoskeleton system of claim 5, wherein the one or more actuator units are configured to be coupled to one or more of a left and right leg of a user.

7. The exoskeleton system of claim 5, wherein the first unitary cable comprises a sheath that surrounds and encloses the one or more electrical power lines, the one or more fluid lines, and the one or more communication lines.

8. The exoskeleton system of claim 5, wherein the first connector side comprises a release button and wherein actuating the release button causes the first and second coupling faces to disengage, including causing the first and second magnets to decouple, causing the first and second pin arrays to de-couple, and causing the fluid stem and fluidic connector to de-couple.

9. The exoskeleton system of claim 5, wherein the first magnet comprises a first cylindrical magnet that surrounds the fluidic connector, and wherein the second magnet comprises a second cylindrical magnet that surrounds the fluid stem.

10. The exoskeleton system of claim 5, wherein the cable connector is configured for a safety disconnect function that allows the cable connector to disengage when the cable connector experiences a sufficient pulling force to cause, without the actuation of a release button, the first and second coupling faces to disengage, including causing the first and second magnets to decouple, causing the first and second pin arrays to de-couple, and causing the fluid stem and the fluidic connector to de-couple.

11. An exoskeleton system comprising:

an exoskeleton device;

a first actuator unit; and one or more unitary cables comprising at least a first unitary cable configured to extend from the exoskeleton device to the first actuator unit, the first unitary cable comprising:

one or more power lines, one or more fluid lines, one or more communication lines, and a cable connector comprising:

a first connector side having a first coupling face that includes a first pin array, a first fluidic connector, and a first magnet, and a second connector side having a second coupling face that includes a second pin array configured to operably couple and decouple with the first pin array, a second fluid connector configured to operably couple and decouple with the first fluidic connector of the first connector side, and a second magnet configured to couple and decouple with the first magnet of the first connector side.

12. The exoskeleton system of claim 11, wherein the first actuator unit comprises a fluidic actuator.

13. The exoskeleton system of claim 11, wherein the exoskeleton device includes:

a fluidic system, and a device configured to control the fluidic system to introduce fluid to a fluidic actuator of the first actuator unit via the one or more fluid lines.

14. The exoskeleton system of claim 11, wherein:

the one or more power lines are configured to convey electrical power from the exoskeleton device to the first actuator unit, the one or more fluid lines are configured to convey a fluid from the exoskeleton device to a fluidic actuator of the first actuator unit, and at least one of the one or more communication lines are configured to convey a communication signal from the exoskeleton device to the first actuator unit.

15. The exoskeleton system of claim 11, wherein the second fluid connector is a fluid stem.

16. The exoskeleton system of claim 15, wherein:

the first unitary cable further comprises a sheath that surrounds and encloses the one or more power lines, the one or more fluid lines, and the one or more communication lines;

the first magnet comprises a first cylindrical magnet that surrounds the first fluidic connector;

the second magnet comprises a second cylindrical magnet that surrounds the fluid stem; and the cable connector further comprises first and second cable portions extending respectively from the first and second connector sides.

17. The exoskeleton system of claim 11, wherein the first connector side comprises a release button and wherein actuating the release button causes the first and second connector sides to disengage.

18. The exoskeleton system of claim 17, wherein causing the first and second connector sides to disengage includes causing the first and second magnets to decouple, causing the first and second pin arrays to decouple, and causing the first fluidic connector and the second fluid connector to decouple.

19. The exoskeleton system of claim 11, wherein the cable connector is configured for a safety disconnect function that allows the cable connector to disengage when the cable connector experiences a sufficient pulling force to cause the first and second connector sides to disengage.

20. The exoskeleton system of claim 11, wherein the first actuator unit is configured to be coupled to one or more of a left and right leg of a user.

* * * * *